(12) United States Patent
Wang et al.

(10) Patent No.: US 11,672,426 B2
(45) Date of Patent: Jun. 13, 2023

(54) SNAPSHOT PHOTOACOUSTIC PHOTOGRAPHY USING AN ERGODIC RELAY

(71) Applicant: California Institute of Technology, Pasadena, CA (US)

(72) Inventors: Lihong Wang, Arcadia, CA (US); Yang Li, Temple City, CA (US); Lei Li, Arcadia, CA (US)

(73) Assignee: California Institute of Technology, Pasadena, CA (US)

( * ) Notice: Subject to any disclaimer, the term of this patent is extended or adjusted under 35 U.S.C. 154(b) by 346 days.

(21) Appl. No.: 16/611,939

(22) PCT Filed: May 10, 2018

(86) PCT No.: PCT/US2018/032007
§ 371 (c)(1),
(2) Date: Nov. 8, 2019

(87) PCT Pub. No.: WO2018/209046
PCT Pub. Date: Nov. 15, 2018

(65) Prior Publication Data
US 2021/0010976 A1 Jan. 14, 2021

Related U.S. Application Data
(60) Provisional application No. 62/503,997, filed on May 10, 2017.

(51) Int. Cl.
*A61B 5/00* (2006.01)
(52) U.S. Cl.
CPC .................. *A61B 5/0095* (2013.01)

(58) Field of Classification Search
CPC .................................................... A61B 5/0095
(Continued)

(56) References Cited

U.S. PATENT DOCUMENTS

| 4,029,756 A | 6/1977 | Gaafar |
| 4,127,318 A | 11/1978 | Determann et al. |

(Continued)

FOREIGN PATENT DOCUMENTS

| CN | 1883379 A | 12/2006 |
| CN | 106338473 A | 1/2017 |

(Continued)

OTHER PUBLICATIONS

Office Action from related U.S. Appl. No. 11/625,099, dated Nov. 1, 2010.
(Continued)

*Primary Examiner* — Lisa M Caputo
*Assistant Examiner* — Rose M Miller
(74) *Attorney, Agent, or Firm* — Sheila Martinez-Lemke; Weaver Austin Villeneuve & Sampson LLP

(57) ABSTRACT

A photoacoustic imaging system is disclosed that includes an ergodic relay coupled optically to a light source configured to produce a light pulse and further coupled acoustically to a transducer. The ergodic relay is further configured to direct at least two PA signals to the transducer. Each of the at least two PA signals are produced at different positions within the field of view of the object to be imaged in response to illumination by a single light pulse. The transducer detects each of the at least two PA signals after each of at least two delays that correspond to the position at which each PA signal was produced.

21 Claims, 25 Drawing Sheets

(58) Field of Classification Search
USPC .......................................... 600/407; 73/643
See application file for complete search history.

(56) References Cited

U.S. PATENT DOCUMENTS

| | | | |
|---|---|---|---|
| 4,255,971 A | 3/1981 | Rosencwaig | |
| 4,267,732 A | 5/1981 | Quate | |
| 4,284,324 A | 8/1981 | Huignard et al. | |
| 4,375,818 A | 3/1983 | Suwaki et al. | |
| 4,385,634 A | 5/1983 | Bowen | |
| 4,430,897 A | 2/1984 | Quate | |
| 4,430,987 A | 2/1984 | Heller | |
| 4,462,255 A | 7/1984 | Guess et al. | |
| 4,468,136 A | 8/1984 | Murphy et al. | |
| 4,489,727 A | 12/1984 | Matsuo et al. | |
| 4,546,771 A | 10/1985 | Eggleton et al. | |
| 4,596,254 A | 6/1986 | Adrian et al. | |
| 4,687,304 A | 8/1987 | Piller et al. | |
| 4,740,081 A | 4/1988 | Martens et al. | |
| 4,802,461 A | 2/1989 | Cho | |
| 4,802,487 A | 2/1989 | Martin et al. | |
| 4,809,703 A | 3/1989 | Ishikawa et al. | |
| 4,850,363 A | 7/1989 | Yanagawa | |
| 4,860,758 A | 8/1989 | Yanagawa et al. | |
| 4,869,256 A | 9/1989 | Kanno et al. | |
| 4,872,758 A | 10/1989 | Miyazaki et al. | |
| 4,921,333 A | 5/1990 | Brody et al. | |
| 4,929,951 A | 5/1990 | Small | |
| 4,995,396 A | 2/1991 | Inaba et al. | |
| 5,070,455 A | 12/1991 | Singer et al. | |
| 5,083,549 A | 1/1992 | Cho et al. | |
| 5,107,844 A | 4/1992 | Kami et al. | |
| 5,115,814 A | 5/1992 | Griffith et al. | |
| 5,125,410 A | 6/1992 | Misono et al. | |
| 5,140,463 A | 8/1992 | Yoo et al. | |
| 5,170,793 A | 12/1992 | Takano et al. | |
| 5,194,723 A | 3/1993 | Cates et al. | |
| 5,207,672 A | 5/1993 | Roth et al. | |
| 5,227,912 A | 7/1993 | Ho et al. | |
| 5,305,759 A | 4/1994 | Kaneko et al. | |
| 5,321,501 A | 6/1994 | Swanson et al. | |
| 5,329,817 A | 7/1994 | Garlick et al. | |
| 5,331,466 A | 7/1994 | Van Saarloos | |
| 5,345,938 A | 9/1994 | Nishiki et al. | |
| 5,373,845 A | 12/1994 | Gardineer et al. | |
| 5,414,623 A | 5/1995 | Lu et al. | |
| 5,445,155 A | 8/1995 | Sieben | |
| 5,465,722 A | 11/1995 | Fort et al. | |
| 5,546,187 A | 8/1996 | Pepper et al. | |
| 5,546,947 A | 8/1996 | Yagami et al. | |
| 5,546,948 A | 8/1996 | Hamm et al. | |
| 5,606,975 A | 3/1997 | Liang et al. | |
| 5,615,675 A | 4/1997 | O'Donnell et al. | |
| 5,635,784 A | 6/1997 | Seale | |
| 5,651,366 A | 7/1997 | Liang et al. | |
| 5,713,356 A | 2/1998 | Kruger | |
| 5,718,231 A | 2/1998 | Dewhurst et al. | |
| 5,781,294 A | 7/1998 | Nakato et al. | |
| 5,836,872 A | 11/1998 | Kenet et al. | |
| 5,840,023 A | 11/1998 | Oraevsky et al. | |
| 5,860,934 A | 1/1999 | Sarvazyan | |
| 5,913,234 A | 6/1999 | Julliard et al. | |
| 5,971,998 A | 10/1999 | Russell et al. | |
| 5,977,538 A | 11/1999 | Unger et al. | |
| 5,991,697 A | 11/1999 | Nelson et al. | |
| 6,055,097 A | 4/2000 | Lanni et al. | |
| 6,102,857 A | 8/2000 | Kruger | |
| 6,104,942 A | 8/2000 | Kruger | |
| 6,108,576 A | 8/2000 | Alfano et al. | |
| 6,111,645 A | 8/2000 | Tearney et al. | |
| 6,134,003 A | 10/2000 | Tearney et al. | |
| 6,216,025 B1 | 4/2001 | Kruger | |
| 6,233,055 B1 | 5/2001 | Mandella et al. | |
| 6,282,011 B1 | 8/2001 | Tearney et al. | |
| 6,292,682 B1 | 9/2001 | Kruger | |
| 6,309,352 B1 | 10/2001 | Oraevsky et al. | |
| 6,341,036 B1 | 1/2002 | Tearney et al. | |
| 6,379,325 B1 | 4/2002 | William et al. | |
| 6,405,069 B1 | 6/2002 | Oraevsky et al. | |
| 6,413,228 B1 | 7/2002 | Hung et al. | |
| 6,421,164 B2 | 7/2002 | Tearney et al. | |
| 6,432,067 B1 | 8/2002 | Martin et al. | |
| 6,466,806 B1 | 10/2002 | Geva et al. | |
| 6,485,413 B1 | 11/2002 | Boppart et al. | |
| 6,490,470 B1 | 12/2002 | Kruger | |
| 6,498,942 B1 | 12/2002 | Esenaliev et al. | |
| 6,498,945 B1 | 12/2002 | Alfheim et al. | |
| 6,501,551 B1 | 12/2002 | Tearney et al. | |
| 6,545,264 B1 | 4/2003 | Stern | |
| 6,564,087 B1 | 5/2003 | Pitris et al. | |
| 6,567,688 B1 | 5/2003 | Wang | |
| 6,590,830 B1 | 7/2003 | Garlick et al. | |
| 6,626,834 B2 | 9/2003 | Dunnie et al. | |
| 6,628,404 B1 | 9/2003 | Kelley et al. | |
| 6,633,774 B2 | 10/2003 | Kruger | |
| 6,654,630 B2 | 11/2003 | Zuluaga et al. | |
| 6,658,279 B2 | 12/2003 | Swanson et al. | |
| 6,694,173 B1 | 2/2004 | Bende et al. | |
| 6,701,181 B2 | 3/2004 | Tang et al. | |
| 6,751,490 B2 | 6/2004 | Esenaliev et al. | |
| 6,764,450 B2 | 7/2004 | Yock | |
| 6,831,781 B2 | 12/2004 | Tearney et al. | |
| 6,833,540 B2 | 12/2004 | MacKenzie et al. | |
| 6,839,496 B1 | 1/2005 | Mills et al. | |
| 6,846,288 B2 | 1/2005 | Nagar et al. | |
| 6,853,446 B1 | 2/2005 | Almogy et al. | |
| 6,877,894 B2 | 4/2005 | Vona et al. | |
| 6,937,886 B2 | 8/2005 | Zavislan | |
| 6,956,650 B2 | 10/2005 | Boas et al. | |
| 7,072,045 B2 | 7/2006 | Chen et al. | |
| 7,198,778 B2 | 4/2007 | Achilefu et al. | |
| 7,231,243 B2 | 6/2007 | Tearney et al. | |
| 7,245,789 B2 | 7/2007 | Bates et al. | |
| 7,266,407 B2 | 9/2007 | Li et al. | |
| 7,322,972 B2 | 1/2008 | Viator et al. | |
| 7,357,029 B2 | 4/2008 | Falk | |
| 7,382,949 B2 | 6/2008 | Bouma et al. | |
| 7,541,602 B2 | 6/2009 | Metzger et al. | |
| 7,610,080 B1 | 10/2009 | Winchester, Jr. et al. | |
| 7,917,312 B2 | 3/2011 | Wang et al. | |
| 8,016,419 B2 | 9/2011 | Zhang et al. | |
| 8,025,406 B2 | 9/2011 | Zhang et al. | |
| 8,143,605 B2 | 3/2012 | Metzger et al. | |
| 8,397,573 B2 | 3/2013 | Kobayashi | |
| 8,416,421 B2 | 4/2013 | Wang et al. | |
| 8,454,512 B2 | 6/2013 | Wang et al. | |
| 8,891,088 B2 | 11/2014 | Goldschmidt et al. | |
| 8,997,572 B2 | 4/2015 | Wang et al. | |
| 9,086,365 B2 | 7/2015 | Wang et al. | |
| 9,096,365 B2 | 8/2015 | Kim | |
| 9,220,415 B2 | 12/2015 | Mandelis et al. | |
| 9,226,666 B2 | 1/2016 | Wang et al. | |
| 9,234,841 B2 | 1/2016 | Wang et al. | |
| 9,335,605 B2 | 5/2016 | Wang et al. | |
| 9,528,966 B2 | 12/2016 | Wang et al. | |
| 9,618,445 B2 | 4/2017 | Sun et al. | |
| 10,285,595 B2 | 5/2019 | Zalev et al. | |
| 10,359,400 B2 | 7/2019 | Wang et al. | |
| 10,433,733 B2 | 10/2019 | Wang et al. | |
| 10,448,850 B2 | 10/2019 | Wang et al. | |
| 11,020,006 B2 | 6/2021 | Wang et al. | |
| 11,029,287 B2 | 6/2021 | Wang et al. | |
| 11,135,375 B2 | 10/2021 | Brady et al. | |
| 11,137,375 B2 | 10/2021 | Wang et al. | |
| 11,369,280 B2 | 6/2022 | Wang et al. | |
| 2001/0052979 A1 | 12/2001 | Treado et al. | |
| 2002/0093637 A1 | 7/2002 | Yuan et al. | |
| 2002/0173780 A1 | 11/2002 | Altshuler et al. | |
| 2002/0176092 A1 | 11/2002 | Deck | |
| 2003/0097066 A1 | 5/2003 | Shelby et al. | |
| 2003/0160957 A1 | 8/2003 | Oldham et al. | |
| 2003/0160967 A1 | 8/2003 | Houston et al. | |
| 2004/0030255 A1 | 2/2004 | Alfano et al. | |
| 2004/0039379 A1 | 2/2004 | Viator et al. | |

(56) References Cited

U.S. PATENT DOCUMENTS

| | | |
|---|---|---|
| 2004/0082070 A1 | 4/2004 | Jones et al. |
| 2004/0254474 A1 | 12/2004 | Seibel et al. |
| 2005/0015002 A1 | 1/2005 | Dixon et al. |
| 2005/0028482 A1 | 2/2005 | Cable et al. |
| 2005/0085725 A1 | 4/2005 | Nagar et al. |
| 2005/0143664 A1 | 6/2005 | Chen et al. |
| 2005/0154313 A1 | 7/2005 | Desilets et al. |
| 2005/0168749 A1 | 8/2005 | Ye et al. |
| 2005/0217381 A1 | 10/2005 | Falk |
| 2005/0234315 A1 | 10/2005 | Mayevsky et al. |
| 2005/0277824 A1 | 12/2005 | Aubry et al. |
| 2006/0055936 A1 | 3/2006 | Yun et al. |
| 2006/0058614 A1 | 3/2006 | Tsujita |
| 2006/0122516 A1 | 6/2006 | Schmidt et al. |
| 2006/0181791 A1 | 8/2006 | Van Beek et al. |
| 2006/0184042 A1 | 8/2006 | Wang et al. |
| 2006/0235299 A1 | 10/2006 | Martinelli |
| 2006/0247510 A1 | 11/2006 | Wiemker et al. |
| 2006/0264717 A1 | 11/2006 | Pesach et al. |
| 2007/0075063 A1 | 4/2007 | Wilbanks et al. |
| 2007/0088206 A1 | 4/2007 | Peyman et al. |
| 2007/0093702 A1 | 4/2007 | Yu et al. |
| 2007/0213590 A1 | 9/2007 | Squicciarini |
| 2007/0213618 A1 | 9/2007 | Li et al. |
| 2007/0213693 A1 | 9/2007 | Plunkett |
| 2007/0282200 A1 | 12/2007 | Johnson et al. |
| 2007/0299341 A1 | 12/2007 | Wang et al. |
| 2008/0029711 A1 | 2/2008 | Viellerobe et al. |
| 2008/0037367 A1 | 2/2008 | Gross et al. |
| 2008/0088838 A1 | 4/2008 | Raicu et al. |
| 2008/0123083 A1 | 5/2008 | Wang et al. |
| 2008/0173093 A1 | 7/2008 | Wang et al. |
| 2008/0230717 A1 | 9/2008 | Ashkenazi et al. |
| 2009/0051900 A1 | 2/2009 | Moon et al. |
| 2009/0054763 A1 | 2/2009 | Wang et al. |
| 2009/0088631 A1 | 4/2009 | Dietz et al. |
| 2009/0116518 A1 | 5/2009 | Patel et al. |
| 2009/0138215 A1 | 5/2009 | Wang et al. |
| 2009/0185191 A1 | 7/2009 | Boppart et al. |
| 2009/0227997 A1 | 9/2009 | Wang et al. |
| 2010/0079768 A1 | 4/2010 | Wang et al. |
| 2010/0134793 A1 | 6/2010 | Krishnamachari et al. |
| 2010/0245766 A1 | 9/2010 | Zhang et al. |
| 2010/0245769 A1 | 9/2010 | Zhang et al. |
| 2010/0245770 A1 | 9/2010 | Zhang et al. |
| 2010/0249562 A1 | 9/2010 | Zhang et al. |
| 2010/0268042 A1 | 10/2010 | Wang et al. |
| 2010/0285518 A1 | 11/2010 | Viator et al. |
| 2010/0309466 A1 | 12/2010 | Lucassen et al. |
| 2010/0322497 A1 | 12/2010 | Dempsey et al. |
| 2011/0071402 A1 | 3/2011 | Masumura |
| 2011/0122416 A1 | 5/2011 | Yang et al. |
| 2011/0201914 A1 | 8/2011 | Wang et al. |
| 2011/0251515 A1 | 10/2011 | Leuthardt et al. |
| 2011/0275890 A1 | 11/2011 | Wang et al. |
| 2011/0282181 A1 | 11/2011 | Wang et al. |
| 2011/0282192 A1 | 11/2011 | Axelrod et al. |
| 2012/0065490 A1 | 3/2012 | Zharov et al. |
| 2012/0070817 A1 | 3/2012 | Wang et al. |
| 2012/0074294 A1 | 3/2012 | Streuber et al. |
| 2012/0118052 A1 | 5/2012 | O'Donnell et al. |
| 2012/0204648 A1 | 8/2012 | Wang et al. |
| 2012/0275262 A1 | 11/2012 | Song et al. |
| 2012/0307250 A1 | 12/2012 | Wang |
| 2013/0151188 A1 | 6/2013 | Rokni et al. |
| 2013/0199299 A1 | 8/2013 | Wang et al. |
| 2013/0218002 A1 | 8/2013 | Kiraly |
| 2013/0245406 A1 | 9/2013 | Wang et al. |
| 2014/0009808 A1 | 1/2014 | Wang et al. |
| 2014/0029829 A1 | 1/2014 | Jiang et al. |
| 2014/0142404 A1 | 5/2014 | Wang et al. |
| 2014/0356897 A1 | 12/2014 | Wang et al. |
| 2015/0005613 A1 | 1/2015 | Kim et al. |
| 2015/0178959 A1 | 6/2015 | Huang et al. |
| 2015/0185187 A1 | 7/2015 | Wang et al. |
| 2015/0245771 A1 | 9/2015 | Wang et al. |
| 2015/0272444 A1 | 10/2015 | Maslov et al. |
| 2015/0272446 A1 | 10/2015 | Wang et al. |
| 2015/0316510 A1 | 11/2015 | Fukushima et al. |
| 2016/0081558 A1 | 3/2016 | Wang et al. |
| 2016/0235305 A1 | 8/2016 | Wang et al. |
| 2016/0242651 A1 | 8/2016 | Wang et al. |
| 2016/0249812 A1 | 9/2016 | Wang et al. |
| 2016/0262628 A1 | 9/2016 | Wang et al. |
| 2016/0305914 A1 | 10/2016 | Wang et al. |
| 2016/0310083 A1 | 10/2016 | Wang et al. |
| 2016/0345886 A1 | 12/2016 | Wang et al. |
| 2017/0065182 A1 | 3/2017 | Wang et al. |
| 2017/0105636 A1 | 4/2017 | Wang et al. |
| 2017/0367586 A9 | 12/2017 | Wang et al. |
| 2018/0020920 A1 | 1/2018 | Ermilov et al. |
| 2018/0088041 A1 | 3/2018 | Zhang et al. |
| 2018/0132728 A1 | 5/2018 | Wang et al. |
| 2018/0177407 A1 | 6/2018 | Hashimoto et al. |
| 2019/0008444 A1 | 1/2019 | Wang et al. |
| 2019/0125583 A1 | 5/2019 | Wang et al. |
| 2019/0227038 A1 | 7/2019 | Wang et al. |
| 2019/0307334 A1 | 10/2019 | Wang et al. |
| 2020/0056986 A1 | 2/2020 | Wang et al. |
| 2020/0073103 A1 | 3/2020 | Wang et al. |
| 2020/0268253 A1 | 8/2020 | Wang et al. |
| 2020/0275846 A1 | 9/2020 | Wang et al. |
| 2020/0397523 A1 | 12/2020 | Gao et al. |
| 2021/0010976 A1 | 1/2021 | Wang et al. |
| 2021/0132005 A1 | 5/2021 | Wang et al. |
| 2021/0321874 A1 | 10/2021 | Wang et al. |
| 2021/0333241 A1 | 10/2021 | Wang et al. |

FOREIGN PATENT DOCUMENTS

| | | |
|---|---|---|
| EP | 0012262 A1 | 6/1980 |
| EP | 0919180 A1 | 6/1999 |
| EP | 1493380 A1 | 1/2005 |
| JP | 05-126725 A | 5/1993 |
| JP | 2000/292416 A | 10/2000 |
| JP | 2009/068977 A | 4/2009 |
| JP | 2010/017426 A | 1/2010 |
| JP | 2010/040161 A | 2/2010 |
| JP | 2012143384 A | 8/2012 |
| JP | 2013244122 A | 12/2013 |
| JP | 2014124242 A | 7/2014 |
| JP | 2014/224806 A | 12/2014 |
| JP | 2016-101260 A | 6/2016 |
| JP | 6086718 B2 | 3/2017 |
| KR | 100946550 B1 | 3/2010 |
| KR | 20160091059 A | 8/2016 |
| KR | 2017-0006470 A | 1/2017 |
| WO | WO2006/111929 A1 | 10/2006 |
| WO | WO2007/088709 A1 | 8/2007 |
| WO | WO2007/148239 A2 | 12/2007 |
| WO | WO2008/062354 A1 | 5/2008 |
| WO | WO2008/100386 A2 | 8/2008 |
| WO | WO2009/055705 A2 | 4/2009 |
| WO | WO2010/048258 A1 | 4/2010 |
| WO | WO2010/080991 A2 | 7/2010 |
| WO | WO2011/060101 A2 | 5/2011 |
| WO | WO2011/091360 A2 | 7/2011 |
| WO | WO2011/127428 A2 | 10/2011 |
| WO | WO2012/035472 A1 | 3/2012 |
| WO | WO2013/086293 A1 | 6/2013 |
| WO | 2015118881 A1 | 8/2015 |
| WO | WO2018/102446 A2 | 6/2018 |
| WO | WO-2018102467 A1 | 6/2018 |
| WO | WO2018/209046 A1 | 11/2018 |

OTHER PUBLICATIONS

Final Office Action from related U.S. Appl. No. 11/625,099, dated Apr. 20, 2010.

Office Action from related U.S. Appl. No. 12/254,643, dated Aug. 6, 2010.

Notice of Allowance from related U.S. Appl. No. 12/254,643, dated Nov. 22, 2010.

(56) References Cited

OTHER PUBLICATIONS

Office Action from related U.S. Appl. No. 12/568,069, dated Dec. 21, 2012.
Office Action from related U.S. Appl. No. 12/568,069, dated Mar. 29, 2012.
Final Office Action from related U.S. Appl. No. 12/568,069, dated Sep. 18, 2012.
Notice of Allowance from related U.S. Appl. No. 12/568,069, dated Feb. 22, 2013.
Office Action from related U.S. Appl. No. 12/739,589, dated Jul. 19, 2012.
Notice of Allowance from related U.S. Appl. No. 12/739,589, dated Feb. 5, 2013.
Office Action from related U.S. Appl. No. 13/125,522, dated Jan. 22, 2013.
Final Office Action from related U.S. Appl. No. 13/125,522, dated May 23, 2013.
Office Action from related U.S. Appl. No. 13/125,522, dated Jul. 17, 2014.
Final Office Action from related U.S. Appl. No. 13/125,522, dated Oct. 29, 2014.
Office Action dated Aug. 26, 2015 issued in U.S. Appl. No. 13/125,522.
Final Office Action dated Mar. 3, 2016 issued in U.S. Appl. No. 13/125,522.
Notice of Allowance dated Sep. 19, 2016 issued in U.S. Appl. No. 13/125,522.
Office Action from related U.S. Appl. No. 13/143,832, dated Apr. 18, 2014.
Office Action from related U.S. Appl. No. 13/450,793, dated Jun. 5, 2013.
Final Office Action from related U.S. Appl. No. 13/450,793, dated Nov. 22, 2013.
Office Action from related U.S. Appl. No. 13/450,793, dated Mar. 24, 2014.
Office Action from related U.S. Appl. No. 13/450,793, dated Aug. 1, 2014.
Office Action from related U.S. Appl. No. 13/574,994, dated Mar. 17, 2014.
Final Office Action from related U.S. Appl. No. 13/574,994, dated Aug. 26, 2014.
Notice of Allowance dated Nov. 17, 2015 from U.S. Appl. No. 13/574,994.
Office Action dated Jan. 20, 2015, from U.S. Appl. No. 14/026,577.
Final Office Action dated Sep. 30, 2015, from U.S. Appl. No. 14/026,577.
Notice of Allowance dated Jan. 5, 2016, from U.S. Appl. No. 14/026,577.
Office Action dated Nov. 13, 2017, from U.S. Appl. No. 15/148,685.
Final Office Action dated Sep. 24, 2018, from U.S. Appl. No. 15/148,685.
Notice of Allowance dated May 16, 2019, from U.S. Appl. No. 15/148,685.
Office Action from related U.S. Appl. No. 13/637,897, dated Aug. 1, 2014.
Office Action from related U.S. Appl. No. 14/164,117, dated Dec. 11, 2015.
Office Action dated Dec. 13, 2019 issued in U.S. Appl. No. 15/037,468.
Notice of Allowance dated Mar. 23, 2020 issued in U.S. Appl. No. 15/037,468.
Notice of Allowance dated Oct. 28, 2020 issued in U.S. Appl. No. 15/037,468.
Office Action dated Oct. 3, 2018 issued in U.S. Appl. No. 14/436,581.
Amendment and Request for Continued Examination dated Nov. 25, 2019 in U.S. Appl. No. 14/436,581.
Final Office Action dated May 24, 2019 issued in U.S. Appl. No. 14/436,581.
Office Action dated Apr. 3, 2020 issued in U.S. Appl. No. 14/436,581.
Office Action dated Jun. 20, 2014 issued in U.S. Appl. No. 13/369,558.
Notice of Allowance dated Jul. 29, 2014 issued in U.S. Appl. No. 13/369,558.
Notice of Allowance dated Dec. 5, 2014 issued in U.S. Appl. No. 13/369,558.
Office Action dated Apr. 21, 2017 issued in U.S. Appl. No. 14/639,676.
Final Office Action dated Nov. 15, 2017 issued in U.S. Appl. No. 14/639,676.
Office Action dated May 31, 2018 issued in U.S. Appl. No. 14/639,676.
Notice of Allowance dated Dec. 12, 2018 issued in U.S. Appl. No. 14/639,676.
Office Action dated Feb. 28, 2020 issued in U.S. Appl. No. 16/372,597.
Office Action dated Aug. 19, 2019 issued in U.S. Appl. No. 16/372,597.
Office Action dated Oct. 8, 2020 issued in U.S. Appl. No. 16/372,597.
The International Search Report and Written Opinion dated Mar. 27, 2014 issued in Application No. PCT/US2013/065594.
The International Search Report and the Written Opinion of the International Searching Authority, or the Declaration, for PCT/US2009/061435, dated Mar. 29, 2010, 6 pages.
The International Search Report and the Written Opinion of the International Searching Authority, dated Sep. 22, 2011, from related application No. PCT/US2011/022253, 6 pgs.
International Search Report of International Application No. PCT/US2014/066437, dated Feb. 26, 2015, 3 pages.
Partial European Search Report issued for European Application No. 17159220.7, dated Aug. 23, 2017 (9 pages).
International Search Report and Written Opinion dated Apr. 22, 2009, from Application No. PCT/US2008/081167 (7 pages).
International Search Report and Written Opinion from Application Serial No. PCT/US2010/020488, dated Aug. 31, 2010 (10 pages).
International Search Report and Written Opinion from Application Serial No. PCT/US2011/031823, dated Dec. 26, 2011 (8 pages).
International Search Report and Written Opinion from Application Serial No. PCTlUS2012/068403, dated Mar. 19, 2013 (10 pages).
Extended European Search Report from European Application Serial No. 08842292.8, dated Dec. 17, 2013 (8 pages).
Final Office Action from related Japanese Patent Application No. JP 2010-531281, dated Mar. 11, 2014, (5 pages).
International Search Report and Written Opinion dated Dec. 2, 2019, issued in Application No. PCT/US2019/046574.
International Search Report and Written Opinion dated Dec. 23, 2019, issued in Application No. PCT/US2019/049594.
International Search Report and Written Opinion dated Aug. 31, 2020, issued in Application No. PCT/US2020/019368.
International Search Report and Written Opinion dated Oct. 14, 2020, issued in Application No. PCT/US2020/07174.
International Preliminary Report on Patentability dated Nov. 12, 2019 issued in PCT/US2018/032007.
Abdelmohsen, et al., "Micro- and nano-motors for biomedical applications," J. Mater. Chem. B 2, (2014) pp. 2395-2408.
Al, et al., "Spectral-domain optical coherence tomography: Removal of autocorrelation using an optical switch," Applied Physics Letters, (Mar. 15, 2006), 88(11): pp. 111115-1-111115-3. <doi:10.1063/1.2186520>.
Allen, et al. "Pulsed Near-Infrared Laser Diode Excitation System for Biomedical Photoacoustic Imaging," Optics Letters, Optical Society of America, USA., vol. 31, No. 23, Dec. 1, 2006, pp. 3462-3464.
Alomair, et al., "In vivo high angular resolution diffusion-weighted imaging of mouse brain at 16.4 Tesla," PloS One 10, Jun. 25, 2015, e0130133, pp. 1-17.
Aubry J.-F., et al., "Experimental demonstration of noninvasive transskull adaptive focusing based on prior computed tomography scans," J. Acoust. Soc. Am. 113(1), 84-93 (2003). (Year: 2003).
Baheiraei, et al., "Investigation of magnesium incorporation within gelatin/calcium phosphate nanocomposite scaffold for bone tissue engineering," Int. J. Appl. Ceram. Technol. 12, (2015) pp. 245-253.
Baker, M. J. et al., "Using Fourier transform IR spectroscopy to analyze biological materials," Nat. Protoc. 9, 1771-1791 (2014).
Bansil, et al., "The biology of mucus: Composition, synthesis and organization" Adv. Drug Deliv. Rev. 124, (2018) pp. 3-15.

(56) References Cited

OTHER PUBLICATIONS

Beaven, G. H. & Holiday, E. R., "Ultraviolet absorption spectra of proteins and amino acids," Adv. Protein Chem 7, 319-386 (1952).
Bell, A.G., "On the Production and Reproduction of Sound by Light," American Journal of Sciences, Oct. 1880, pp. 305-324, Third Series, vol. XX, USA.
Bellinger, et al., "Oral, ultra-long-lasting drug delivery: Application toward malaria elimination goals" Sci Transl. Med. 8(365), Nov. 16, 2016, 365ra157, pp. 1-25. <doi:10.1126/scitranslmed.aag2374>.
Bioucas-Dias, J.M. And Figueiredo, M.A.T. "A new TwIST: two-step iterative shrinkage/thresholding algorithms for image restoration," IEEE Trans. Image Process. 16, 2992-3004 (Dec. 2007).
Brenner, et al., "Computed Tomography—An Increasing Source of Radiation Exposure" N. Engl. J. Med 357;22, Nov. 29, 2007, pp. 2277-2284.
Calasso et al., "Photoacoustic Point Source," Physical Review Letters, vol. 86, No. 16, Apr. 16, 2001, pp. 3550-3553.
Cannata et al., "Development of a 35-MHz Piezo-Composite Ultrasound Array for Medical Imaging," IEE Transactions on Ultrasonics, Ferroelectrics, and Frequency Control, 53(1): pp. 224-236 (2006).
Celli, J. P., et al., "Helicobacter pylori moves through mucus by reducing mucin viscoelasticity," Proc. Natl. Acad. Sci. U. S. A. 106, (2009) pp. 14321-14326.
Chan, et al., "New opportunities in micro- and macro-attenuated total reflection infrared spectroscopic imaging: spatial resolution and sampling versatility," Appl. Spectrosc. 57, 381-389 (2003).
Cheng, J.-X. Et al., "Vibrational spectroscopic imaging ofliving systems: an emerging platform for biology and medicine," Science, vol. 350 aaa8870, No. 6264, Nov. 27, 2015, pp. 1054-1063.
Cheong, et al., "A review of the optical properties of biological tissues," IEEE J. Quantum Electronics, 26(12): pp. 2166-2185 (1980).
Chourasia, et al., "Design and Development of Multiparticulate System for Targeted Drug Delivery to Colon," Drug Delivery, 11:3, (2004) pp. 201-207.
Cox, B., Beard, P., "Photoacoustic tomography with a single detector in a reverberant cavity" J. Acoust. Soc. Am. 125, 1426 (Mar. 2009).
Cui, Y., et al. "Transferring-conjugated magnetic silica PLGA nanoparticles loaded with doxorubicin and paclitaxel for brain glioma treatment," Biomaterials 34, (2013) pp. 8511-8520.
De Boer, et al., "Improved signal-to-noise ratio in spectral-domain compared with time-domain optical coherence tomography" Optics Letters, vol. 28, No. 21, Nov. 1, 2003, pp. 2067-2069.
D'Andrea, et al., "Time-resolved optical imaging through turbid media using a fast data acquisition system based on a gated CCD camera" Journal of Physics D: Applied Physics, vol. 36, No. 14, Jul. 1, 2003, pp. 1675-1681.
Danielli, et al., "Label-free photoacoustic nanoscopy," Journal of Biomedical Optics, vol. 19, No. 8, Aug. 2014, pp. 086006-1-086006-10.
Dazzi, A. et al., "AFM-IR: technology and applications in nanoscale infrared spectroscopy and chemical imaging," Chem. Rev. 117, 5146-5173 (2017).
Dazzi, A., et al., "Local infrared microspectroscopy with subwavelength spatial resolution with an atomic force microscope tip used as a photothermal sensor," Optics Letters, vol. 30, No. 18, Sep. 15, 2005, pp. 2388-2390.
De Avila, et al., "Micromotor-enabled active drug delivery for in vivo treatment of stomach infection" Nat. Commun. 8: 272, (2017) pp. 1-9.
De Zerda, et al., "Family of enhanced photoacoustic imaging agents for high-sensitivity and multiplexing studies in living mice," ACS Nano 6(6), Jun. 26, 2012, pp. 4694-4701.
Diebold, et al., "Photoacoustic Monopole Radiation in One, Two and Three Dimensions," Physical Review Letters, Figs. 1 and 2, vol. 67, No. 24, Dec. 9, 1991, pp. 3384-3387.

Diebold, et al., "Photoacoustic Signature of Particulate Matter: Optical Production of 9 Acoustic Monopole Radiation," Science New Series, Oct. 5, 1990, pp. 101-104, vol. 250, No. 4977, pp. 101-104.
Diem, M. et al., "Molecular pathology via IR and Raman spectral imaging." Journal of Biophotonics, vol. 6, No. 11-12 (2013) pp. 855-886. <doi:10.1002/jbio.201300131>.
Diem, M., et al., "A decade of vibrational micro-spectroscopy of human cells and tissue (1994-2004)," Analyst, Oct. 2004, vol. 129, No. 10, pp. 880-885. <doi:10.1039/b408952a>.
Draeger, C., Fink, M., "One-channel time reversal of elastic waves in a chaotic 2D-silicon cavity," Phys. Rev. Lett. 79, 407-410 (Jul. 21, 1997).
Dunn, et al., "Transport-based image reconstruction in turbid media with small source-detector separations," Optics Letters, vol. 25, No. 24, Dec. 15, 2000, pp. 1777-1779.
Eghtedari, et al., "High Sensitivity of in Vivo Detection of Gold Nanorods Using a Laser Optoacoustic Imaging System," Nano Letters, vol. 7, No. 7, 2007, pp. 1914-1918.
Ermilov et al., "Laser optoacoustic imaging system for detection of breast cancer," Journal of Biomedical Optics, vol. 14 No. 2, pp. 24007-024007-14 (2009).
Erpelding et al., "Sentinel Lymph Nodes in the Rat: Noninvasive Photoacoustic and US Imaging with a Clinical US System," Radiology, 256(1): 102-110 (2010).
Evans, et al., "Coherent Anti-Stokes Raman Scattering Microscopy: Chemical Imaging for Biology and Medicine," Annual Review of Analytical Chemistry 1, (2008), pp. 883-909.
Fan, et al., "Development of a Laser Photothermoacoustic Frequency-Swept System for Subsurface Imaging: Theory and Experiment," J. Acoust. Soc. Am., vol. 116 (6), Dec. 2004, pp. 3523-3533.
Fan, et al., "Sub-Cellular Resolution Delivery of a Cytokine via Precisely Manipulated Nanowires" Nat. Nanotechnol. 5(7), Jul. 2010, 545-551. <doi:10.1038/nnano.2010.104>.
Fang, et al., "Photoacoustic Doppler effect from flowing small light-absorbing particles," Physical Review Letters 99(18) 184501-(1-4) (Nov. 2, 2007).
Fercher, et al., "Measurement of Intraocular Distances by Backscattering Spectral Interferometry," Optics Communications, 1995, vol. 117, pp. 43-48.
Fernandez, D. C., Bhargava, R., Hewitt, S. M. & Levin, I. W., "Infrared spectroscopic imaging for histopathologic recognition," Nat. Biotechnol. 23, 469-474 (2005).
Foster, et al., "Advances in ultrasound biomicroscopy" Ultrasound in Medicine & Biology, vol. 26, No. 1, Jan. 2000, pp. 1-27.
Fujita, K., et al., "Confocal multipoint multiphoton excitation microscope with microlens and pinhole arrays," Opt. Comm. 174, 7-12 (Jan. 15, 2000).
Furstenberg, et. al., "Chemical Imaging using Infrared Photothermal Microspectroscopy," In Proceedings of SPIE Defense, Security, and Sensing (eds Druy, M.A. & Crocombe, R. A.) 837411 (SPIE, 2012).
Gaihre, et al., "Gelatin-coated magnetic iron oxide nanoparticles as carrier system: Drug loading and in vitro drug release study," Int. J. Pharm. 365, (2009) pp. 180-189.
Gao, et al., "Single-shot compressed ultrafast photography at one hundred billion frames per second," Nature 516(7529) 74-77 (Dec. 4, 2014).
Gao, et al., "A review of snapshot multidimensional optical imaging: measuring photon tags in parallel" Phys Rep. 616, Feb. 29, 2016, pp. 1-37. <doi:10.1016/j.physrep.2015.12.004>.
Gao, et al., "Artificial micromotors in the mouse's stomach: A step toward in vivo use of synthetic motors," ACS Nano 9, (2015) pp. 117-123.
Gibson, et al., "Recent advances in diffuse optical imaging" Physics in Medicine and Biology 50, 2005, pp. R1-R43, Institute of Physics Publishing, UK.
Gong, L. et al., "Breaking the diffraction limit by saturation in stimulated-Raman-scattering microscopy: a theoretical study," Phys. Rev. A 90, 13818 (2014).
Griffiths, P., "Fourier transform infrared spectrometry," Science 21, 297-302 (1983).

(56) References Cited

OTHER PUBLICATIONS

Guggenheim, et al., "Ultrasensitive planoconcave optical microresonators for ultrasound sensing", Nat. Photon. 11, 714-721 (2017).
Guittet C, et al., "In vivo high-frequency ultrasonic characterization of human dermis" IEEE Transactions on Bio-medical Engineering. Jun. 1999;46(6):740-746. <doi:10.1109/10.764950>.
Guo, et al., "Calibration-free absolute quantification of optical absorption coefficients using acoustic spectra in three-dimensional photoacoustic microscopy of biological tissue" Opt Lett. 2010; 35(12): 2067-2069. <doi:10.1364/OL.35.002067>.
Guo, et al., "CsxWO3 nanorods coated with polyelectrolyte multilayers as a multifunctional nanomaterial for bimodal imaging-guided photothermal/photodynamic cancer treatment," Adv. Mater. 29, 1604157 (2017).
Haas, J. et al., "Advances in Mid-Infrared Spectroscopy for Chemical Analysis," Annu. Rev. Anal. Chem. 9 (2016) pp. 45-68.
Hai, et al., "Near-infrared optical-resolution photoacoustic microscopy", Opt. Lett. 39, 5192-5195 (Sep. 1, 2014).
Hai, et al., "High-throughput, label-free, single-cell photoacoustic microscopy of intratumoral metabolic heterogeneity," Nature Biomedical Engineering 3(5) 381-391 (May 2019).
Hebden et al., "Enhanced time-resolved imaging with a diffusion model of photon transport" Optics Letters, vol. 19, No. 5, 1994, pp. 311-313.
Hee, et al., "Femtosecond transillumination tomography in thick tissues" Optics Letters, vol. 18, No. 13, 1993, pp. 1107-1109.
Hillman, et al., "Laminar optical tomography: demonstration of millimeter-scale depth-resolved imaging in turbid media," Optics Letters, vol. 29, No. 14, Jul. 15, 2004, pp. 1650-1652.
Hoelen, et al., "Three-Dimensional Photoacoustic Imaging of Blood Vessels in Tissue" Optics Letters, 1998, pp. 648-650, vol. 23, No. 8, Optical Society of America, USA.
Hong, et al., "Simple Method to Produce Janus Colloidal Particles in Large Quantity" Langmuir 22, (2006) pp. 9495-9499.
Hu, C., et al., "Soft Micro- and Nanorobotics," Annu. Rev. Control. Robot. Auton. Syst. 1, (2018) pp. 53-75.
Hu, W., et al., "Small-scale soft-bodied robot with multimodal locomotion," Nature 554, 81-85, (2018).
Hu, S. et al., "Three-dimensional optical-resolution photoacoustic microscopy," Journal of Visualized Experiments 51 (2011).
Hu, S., et al., "Label-free Photoacoustic Ophthalmic Angiography" Optics Letters, 35(1), Jan. 1, 2010, pp. 1-3.
Huang, et al., "Aberration correction for transcranial photoacoustic tomography of primates employing adjunct image data," Journal of Biomedical Optics, vol. 17, No. 6, Jun. 2012, pp. 066016-1 to 066016-8.
Huang, et al., "Optical Coherence Tomography," Science, New Series, vol. 254, No. 5035, Nov. 22, 1991, pp. 1178-1181.
Huber, et al., "Three-Dimensional and C-Mode 6 OCT Imaging with a Compact, Frequency Swept Laser Source at 1300 nn" Optics Express, vol. 13, No. 26, Dec. 26, 2005, pp. 10523-10526.
Imai, T. et al., "High-throughput ultraviolet photoacoustic microscopy with multifocal excitation," Journal of Biomedical Optics 23(3), 036007 (Mar. 15, 2018).
Ing, R. K., Quieffin, N., Catheline, S., Fink, M., "In solid localization of finger impacts using acoustic time-reversal process," Appl. Phys. Lett. 87, 204104 (Nov. 14, 2005).
Ji, M. et al., "Detection of human brain tumor infiltration with quantitative stimulated Raman scattering microscopy," Sci. Transl. Med 7, 309ra163 (2015).
Ji, T. et al. "Preparation, Characterization, and Application of Au-Shell/Polystyrene Beads and Au-hell/Magnetic Beads" Adv. Mater. 13(16), Aug. 2001, pp. 1253-1256.
Karamata, et al., "Multiple Scattering in Optical Coherence Tomography I Investigation and Modeling" Journal of Optical Society of America, vol. 22, No. 7 (2005) pp. 1369-1379.
Karamata, et al., "Multiple scattering in optical coherence tomography. II. Experimental and theoretical investigation of cross talk in wide-field optical coherence tomography" J. Opt. Soc. Am. A/vol. 22, No. 7/Jul. 2005, pp. 1380-1388.

Karshalev, E. et al., "Micromotor Pills as a Dynamic Oral Delivery Platform" American Chemical Society Nano, 2018, vol. 12, No. 8, pp. 8397-8405 <DOI: 10.1021/acsnano.8b03760>.
Kim, C. et al., "In vivo molecular photoacoustic tomography of melanomas targeted by bio-conjugated gold nanocages" ACS Nano, 2010; 4(8), pp. 4559-4564. <doi:10.1021/nn100736c>.
Kirch, J., et al., "Optical tweezers reveal relationship between microstructure and nanoparticle penetration of pulmonary mucus," Proc. Natl. Acad. Sci. 109, (2012) pp. 18355-18360.
Knoll, B. & Keilmann, F., "Near-field probing of vibrational absorption for chemical microscopy," Nature 399, 134-137 (1999).
Kole, M. R., et al., "Discrete frequency infrared microspectroscopy and imaging with a tunable quantum cascade laser," Anal. Chem. 84, 10366-10372 (2012).
Kolkman, et al., "In Vivo Photoacoustic Imaging of Blood Vessels Using an Extreme-Narrow Aperture Sensor" IEEE Journal of Selected Topics in Quantum Electronics, vol. 9, No. 2, Mar./Apr. 2003, pp. 343-346.
Koziolek, et al., "Navigating the human gastrointestinal tract for oral drug delivery: Uncharted waters and new frontiers," Adv. Drug Delivery Rev. 101, (2016) pp. 75-88.
Kruger et al., "Photoacoustic Ultrasound (PAUS)-Reconstruction Tomography" Med. Phys., Oct. 1995, vol. 22 (10) Am. Assoc. Phys. Med., USA, pp. 1605-1609.
Kruger, et al., "Thermoacoustic computed tomography—technical considerations" Medical Physics, 26(9): 1832-1837 (1999).
Kruger et al., "Thermoacoustic computed tomography using a conventional linear transducer array," Medical Physics, 30(5): 856-860 (2003).
Kruger, et al., "Thermoacoustic Molecular Imaging of Small Animals," Molecular Imaging, 2(2): 113-123 (2003).
Kruger, et al., "Thermoacoustic CT: imaging principles," Proc. SPIE 3916, (2000) pp. 150-160.
Kruger, et al., "Breast Cancer in Vivo: Contrast Enhancement with Thermoacoustic CT at 434 MHz-Feasibility Study," Radiology, 216(1): 279-283 (2000).
Ku and Wang, "Scanning thermoacoustic tomography in biological tissue." Medical physics 27.5 (2000): 1195-1202.
Ku and Wang, "Scanning microwave-induced thermoacoustic tomography: Signal, resolution, and contrast," Medical Physics, 28(1): 4-10 (2001).
Ku, G. et al., "Multiple-bandwidth photoacoustic tomography," Physics in Medicine & Biology, 49(7): 1329-1338 (2004).
Ku and Wang, "Deeply penetrating photoacoustic tomography in biological tissues enhanced with an optical contrast agent," Optics Letters, 30(5): 507-509 (2005).
Ku, et al., "Imaging of tumor angiogenesis in rat brains in vivo by photoacoustic tomography," Applied Optics, 44(5): 770-775 (2005).
Ku, et al., "Thermoacoustic and Photoacoustic Tomography of Thick Biological Tissues Toward Breast Imaging," Technology in Cancer Research & Treatment, 4(5): 559-566 (2005).
Kunitz, M., "Crystalline desoxyribonuclease; isolation and general properties; spectrophotometric method for the measurement of desoxyribonuclease activity," The Journal General Physiology, vol. 33, Mar. 20, 1950, pp. 349-362. <URL:http://doi.org./10.1085/jgp.33.4.349>.
Kuppusami, S. et al., "Parylene Coatings in Medical Devices and Implants: A Review" Universal Journal of Biomedical Engineering, 2015, vol. 3, No. 2, pp. 9-14 <DOI: 10.13189/ujbe.2015.030201>.
Lai, S. et al., "Mucus-penetrating nanoparticles for drug and gene delivery to mucosal tissues," Adv. Drug Deliv. Rev. 61(2), Feb. 27, 2009, pp. 158-171. <doi:10.1016/j.addr.2008.11.002>.
Lai, P. et al., "Photoacoustically guided wavefront shaping for enhanced optical focusing in scattering media," Nature Photonics 9 126-132 (Jan. 19, 2015).
Lai, P. et al., "Dependence of optical scattering from Intralipid in gelatin-gel based tissue-mimicking phantoms on mixing temperature and time" Journal of Biomedical Optics, vol. 19, No. 3, Mar. 2014, pp. 035002-1-035002-6.
Larina, et al., Real-time optoacoustic monitoring of temperature in tissues: Journal of Physics D: Applied Physics, vol. 38, (2005) pp. 2633-2639.

(56) References Cited

OTHER PUBLICATIONS

Lasch, et al., "FT-IR spectroscopic investigations of single cells on the subcellular level," Vibr. Spectrosc. 28, 147-157 (2002).
Laser Institute of America, "American National Standard for the safe use of lasers," American National Standard Institute (ANSI Z136.1-2007 Revision of ANSI Z136.1-2000).
Leal, et al., "Physicochemical properties of mucus and their impact on transmucosal drug delivery," Int. J. Pharm. 532, (2017) pp. 555-572.
Lewis, E. N. et al., "Fourier transform spectroscopic imaging using an infrared focal-Plane array detector," Anal. Chem. 67, 3377-3381 (1995).
Leitgeb, et al., "Performance of fourier domain vs. time domain optical coherence tomography," Optical Express, vol. 11, No. 8, Apr. 21, 2003, pp. 889-894.
Li, et al., "An Enteric Micromotor Can Selectively Position and Spontaneously Propel in the Gastrointestinal Tract," ACS Nano. 10(10), Oct. 25, 2016, pp. 9536-9542. <doi:10.1021/acsnano.6b04795>.
Li, et al., "Autonomous Collision-Free Navigation of Microvehicles in Complex and Dynamically Changing Environments" ACS Nano, 11, (2017) pp. 9268-9275.
Li, G., et al., "Reflection-mode multifocal optical-resolution photoacoustic microscopy," J. Biomed. Opt. 18, 030501 (Feb. 12, 2013).
Li, J. et al., "Micromotors Spontaneously Neutralize Gastric Acid for pH-Responsive Payload Release" ANGEWANDTE CHEMIE International Edition, vol. 56, No. 8, 2017, pp. 2156-2161. <DOI: 10.1002/anie.201611774>.
Li, L., et al., "Small near-infrared photochromic protein for photoacoustic multi-contrast imaging and detection of protein interactions in vivo," Nature Communications 9(1) 2734 (Jul. 16, 2018).
Li, et al., "Single-impulse panoramic photoacoustic computed tomography of small-animal whole-body dynamics at high spatiotemporal resolution," Nat Biomed Eng. 1(5) May 2017, pp. 1-11. <doi:10.1038/s41551-017-0071>.
Li, L . . . , et al., "Simultaneous Molecular and Hypoxia Imaging of Brain Tumors in Vivo Using Spectroscopic Photoacoustic Tomography," Proceedings of the IEEE, 96(3): 481-489 (2008).
Li, J. et al., "Micro/Nanorobots for Biomedicine: Delivery, Surgery, Sensing, and Detoxification" Sci Robot, 2(4), Mar. 15, 2017, pp. 1-20. <doi:10.1126/scirobotics.aam6431>.
Li, Y. et al., "Multifocal photoacoustic microscopy through an ergodic relay (Conference Presentation)", Proc. SPIE 10878, Photons Plus Ultrasound: Imaging and Sensing 2019, 108781C, presented Feb. 4, 2019, published Mar. 4, 2019, https://doi.org/10.1117/12.2513502.
Li, et al., "Optical Coherence Computed Tomography," Applied Physics Letters, vol. 91, American Institute of Physics, 2007, pp. 141107-1-141107-3.
Li, et al., "Snapshot photoacoustic topography through an ergodic relay for high-throughput imaging of optical absorption," Nature Photonics 14(3) (2020) pp. 164-170. <URL:https://doi.org/10.1038/s41566-019-0576-2>.
Li, Z., et al., "Super-resolution far-field infrared imaging by photothermal heterodyne imaging," The Journal of Physical Chemistry B, vol. 121 (2017) pp. 8838-8846.
Li, Z., et al., "Super-resolution imaging with mid-IR photothermal microscopy on the single particle level," in Proceedings of SPIE Physical Chemistry of Interfaces and Nano-materials XIV, vol. 9549, Aug. 20, 2015, pp. 954912-1-954912-8.
Liang, et al., "Single-shot real-time femtosecond imaging of temporal focusing," Light-Science & Applications 7(1) 42 (Aug. 8, 2018).
Liang, et al., "Single-shot real-time video recording of a photonic Mach cone induced by a scattered light pulse," Science Advances 3(1) e1601814 (Jan. 20, 2017).
Liang, et al., "Single-shot ultrafast optical imaging," Optica 5(9) 1113-1127 (Sep. 2018).

Lin, et al., "Single-breath-hold photoacoustic computed tomography of the breast," Nature Communications 9(1) 2352 (Jun. 15, 2018).
Liu, et al., "Optical focusing deep inside dynamic scattering media with near-infrared time-reversed ultrasonically encoded (TRUE) light," Nature Communications 6 5409 (Jan. 5, 2015).
Liu, et al., "Label-free cell nuclear imaging by Grüneisen relaxation photoacoustic microscopy" Opt Lett. Feb. 15, 2018; 43(4), (2018) pp. 947-950.
Lovell, et al., "Porphysome nanovesicles generated by porphyrin bilayers for use as multimodal biophotonic contrast agents," Nature Materials 10(4) 324-32 (Mar. 20, 2011).
Lu, F., et al., "Tip-enhanced infrared nanospectroscopy via molecular expansion force detection," Nat. Photon. 8, 307-312 (2014).
Lu, F.-K. et al., "Label-free DNA imaging in vivo with stimulated Raman scattering microscopy," Proc. Natl Acad Sci. USA 112, 11624-11629 (2015).
Ma, et al., "Time-reversed adapted-perturbation (TRAP) optical focusing onto dynamic objects inside scattering media," Nature Photonics 8(12) 931-936 (Nov. 2, 2014).
Manohar, et al., "Initial results of in vivo non-invasive cancer imaging in the human breast using near-infrared photoacoustics," Optics Express, 15(19): 12277-12285 (2007).
Maslov, et al., "In vivo dark-field reflection-mode photoacoustic microscopy," Optics Letters 30(6), Mar. 15, 2005, pp. 625-627.
Maslov, et al., "Optical-resolution photoacoustic microscropy for in vivo imaging of single capillaries," Optical Letters, 33(9): 929-931 (2008).
Maslov, et al., "Photoacoustic Imaging of biological tissue with Intensity-Modulated Continuous-Wave Laser" Journal of Biomedical Optics, 2008, pp. 024006 1-024006 5, vol. 13(2), SPIE, USA.
Medina-Sanchez, et al., "Medical microbots need better imaging and control," Nature 545, (2017) pp. 406-408.
Michaelian, Kirk H. Photoacoustic IR spectroscopy: instrumentation, applications and data analysis. Pub: John Wiley & Sons; Dec 1, 2010. <PREFACE ONLY>.
Miller, et al., "Synchrotron-based biological microspectroscopy: From the mid-infrared through the far-infrared regimes," Journal of Biological Physics 29, 219-230 (2003).
Mishra et al., "Development and comparison of the DTM, the DOM and the FVM formulations for the short-pulse laser transport through a participating medium" International Journal of Heat and Mass Transfer, vol. 49 (2006) pp. 1820-1832.
Montaldo, et al., "Building three-dimensional images using time-reversal chaotic cavity", IEEE Trans. Ultrason. Ferroelectr. Freq. Control 52, pp. 1489-1497 (2005).
Morgner et al., "Spectroscopic optical coherence tomography," Optics Letters, vol. 25, No. 2, Jan. 15, 2000, pp. 111-113.
Murray et al., "High-Sensitivity Laser-Based Acoustic Microscopy Using a Modulated Excitation Source," Applied Physics Letters, vol. 85, No. 14, American Institute of Physics, USA., Oct. 4, 2004, pp. 2974-2976.
Nakajima, et al., "Three-dimensional analysis and classification of arteries in the skin and subcutaneous adipofascial tissue by computer graphics imaging," Plastic and Reconstructive Surgery, 102(3): 748-760 (1998).
Nasiriavanaki, et al., "High-resolution photoacoustic tomography of resting-state functional connectivity in the mouse brain," Proceedings of the National Academy of Sciences 111(1) 21-26 (Jan. 7, 2014).
Nasse, M. J. et al., "High-resolution Fourier-transform infrared chemical imaging with multiple synchrotron beams," Nat. Methods 8, 413-416 (2011).
Nelson et al., "Imaging Glioblastoma Multiforme," The Cancer Journal vol. 9, No. 2, Mar./Apr. 2003, pp. 134-145.
Niederhauser et al., "Combined Ultrasound and Optoacoustic System for Real-Time High-Contrast Vascular imaging in Vivo," IEEE Transactions on MedicalImaging, 24(4): 436-440 (2005).
Nowak, D. et al., "Nanoscale chemical imaging by photoinduced force microscopy," Sci. Adv. 2, Mar. 25, 2016, e1501571, pp. 1-9.
Ntziachristos, V., "Going deeper than microscopy: the optical imaging frontier in biology" Nature Methods vol. 7, No. 8, Aug. 2010, pp. 603-614.

(56) References Cited

OTHER PUBLICATIONS

Oraevsky et al., "Optoacoustic Tomography," Biomedical Photonics Handbook, 2003, chapter 34: pp. 931-964, CRC Press LLC, USA.
Oraevsky et al., "Ultimate Sensitivity of Time-Resolved Opto-Acoustic Detection," Biomedical Optoacoustics, 2000, pp. 228-239, vol. 3916, SPIE, USA.
Oraevsky et al., "Laser Optoacoustic Tomography of Layered Tissues: Signal Processing" Proceedings of SPIE, 2979: 59-70 (1997).
Oraevsky et al., "Laser opto-acoustic imaging of the breast: Detection of cancer angiogenesis" Proceedings of SPIE, 3597: 352-363 (1999).
Patel, et al., "Pulsed optoacoustic spectroscopy of condensed matter," Rev. Mod. Phys., vol. 53 (1981) pp. 517-550.
Paxton, et al., "Catalytic nanomotors: Autonomous movement of striped nanorods," J. Am. Chem. Soc. 126, 13424-13431 (2004).
Petrov, et al., "Optoacoustic, Noninvasive, Real-Time, Continuous Monitoring of Cerebral Blood Oxygenation: An in Vivo Study in Sheep" Anesthesiology, vol. 102, No. 1, Jan. 2005, pp. 69-75.
Potter, et al., "Capillary diameter and geometry in cardiac and skeletal muscle studied by means of corrosion casts" Microvascular Research, 25(1): 68-84 (1983).
Prati, et al., "New advances in the application of FTIR microscopy and spectroscopy for the characterization of artistic materials," Accounts of Chemical Research, vol. 43, (2010) pp. 792-801.
Prevedel, et al., "Simultaneous whole-animal 3D imaging of neuronal activity using light-field microscopy," Nat. Methods 11, 727-730 (Jul. 2014).
Quickenden, et al., "The ultraviolet absorption spectrum ofliquid water," J Chem. Phys. 72, 4416-4428 (1980).
Razansky, et al., "Multispectral opto-acoustic tomography of deep-seated fluorescent proteins in vivo," Nature Photonics 3, (2009) pp. 412-417.
Robert et al., "Fabrication of Focused Poly (Vinylidene Fluoride-Trifluoroethylene) P19 (VDF-TrFE) Copolymer 40-50 MHz Ultrasound Transducers on Curved Surfaces," Journal of Applied Physics, vol. 96, No. 1. Jul. 1, 2004, pp. 252-256.
Rockley, M.G., "Fourier-transformed infrared photoacoustic spectroscopy of polystyrene film," Chem. Phys. Lett. 68, 455-456 (1979).
Rosenblum, et al., "Progress and challenges towards targeted delivery of cancer therapeutics" Nat. Commun. 9, (2018) 1410, pp. 1-12.
Saager et al., "Direct characterization and removal of interfering absorption trends in two-layer turbid media" J. Opt. Soc. Am. A, vol. 22, No. 9, Sep. 2005, pp. 1874-1882.
Sanchez, et al., "Chemically powered micro- and nanomotors," Angew. Chem. Int. Ed. 54, (2015) pp. 1414-1444.
Sakadzic, et al., "Correlation transfer and diffusion of ultrasound-modulated multiply scattered light," Physical Review Letters 96(16) 163902—(1-4) (Apr. 28, 2006).
Savateeva, et al., "Noninvasive detection and staging or oral cancer in vivo with confocal opto-acoustic tomography" Biomedical Optoacoustics, vol. 3916, International Society for Optics and Photonics 2000, pp. 55-66.
Schambach, et al., "Application of micro-CT in small animal imaging" Methods, vol. 50, No. 1, Jan. 2010, pp. 2-13.
Schmidt, et al., "A 32-Channel Time Resolved Instrument for Medical Optical Tomography" Review of Scientific Instruments, vol. 71, No. 1, Jan. 2000, pp. 256-265.
Schroeter, et al., "Spontaneous slow hemodynamic oscillations are impaired in cerebral microangiopathy," Journal of Cerebral Blood Flow & Metabolism (2005) 25, pp. 1675-1684.
Servant, et al., "Controlled in Vivo Swimming of a Swarm of Bacteria-Like Microrobotic Flagella" Advanced Materials 27, (2015) pp. 2981-2988.
Sezer, et al., "Review of magnesium-based biomaterials and their applications," J. Magnesium Alloys 6, (2018) pp. 23-43.
Sethuraman et al., "Development of a combined intravascular ultrasound and photoacoustic imaging system" Proceedings of SPIE, 6086: 60860F.1-60860F.10 (2006).
Sethuraman et al., "Intravascular photoacoustic imaging of atherosclerotic plaques: Ex vivo study using a rabbit model of atherosclerosis" Proceedings of SPIE, 6437: 643729.1-643729.9 (2007).
Shah, J. et al, "Photoacoustic imaging and temperature measurement for photothermal cancer therapy," Journal of Biomedical Optics, vol. 13, No. 3, (May/Jun. 2008) pp. 034024-1-034024-9.
Sheth, et al., "Columnar Specificity of Microvascular Oxygenation and Volume Responses: Implications for Functional Brain Mapping," The Journal of Neuroscience, vol. 24, No. 3, Jan. 21, 2004, pp. 634-641.
Shi, J., et al., "High-resolution, high-contrast mid-infrared imaging of fresh biological samples with ultraviolet-localized photoacoustic microscopy," Nature Photonics 13 609-615 (May 2019).
Shmueli, et al., "Low Frequency Fluctuations in the Cardiac Rate as a Source of Variance in the Resting-State fMRI BOLD Signal," Neuroimage, vol. 38, No. 2, Nov. 1, 2007, pp. 306-320.
Silva, et al., "Toward Label-Free Super-Resolution Microscopy," ACS Photon. 3, 79-86 (2016).
Sim, et al., "In vivo Microscopic Photoacoustic Spectroscopy for Non-Invasive Glucose Monitoring Invulnerable to Skin Secretion Products," Sci. Rep. 8, 1059 (2018).
Siphanto et al., "Imaging of Small Vessels Using Photoacoustics: an in Vivo Study," Lasers in Surgery and Medicince, vol. 35, Wiley-Liss, Inc., Netherlands, Dec. 20, 2004, pp. 354-362.
Sitti, M., "Miniature soft robots—road to the clinic," Nat. Rev. Mater, 3, (2018) pp. 74-75.
Smith, et al., "Beyond C, H, O, and Ni analysis of the elemental composition of U.S. FDA approved drug architectures," J. Med. Chem. 57, pp. 9764-9773 (2014).
Sommer, A. J., et al., "Attenuated total internal reflection infrared mapping microspectroscopy using an imaging microscope," Appl. Spectrosc. 55, 252-256 (2001).
Song, et al., "Fast 3-D dark-field reflection-mode photoacoustic microscopy in vivo with a 30-MHz ultrasound linear array" Journal of Biomedical Optics, 13(5): 054028.1-054028.5 (2008).
Song et al., "Multi-focal optical-resolution photoacoustic microscopy in vivo." NIH Public Access Author Manuscript, May 13, 2011. pp. 1-7.
Song, et al., "Section-illumination photoacoustic microscopy for dynamic 3D imaging of microcirculation in vivo" Optics Letters, 35(9): 1482-1484 (2010).
Soppimath, et al., "Microspheres as floating drug-delivery systems to increase gastric retention of drugs" Drug Metab. Rev. 33, (2001) pp. 149-160.
Steinbrink, et al., "Illuminating the BOLD signal: combined fMRI-fNIRS studies" Magnetic Resonance Imaging, vol. 24, No. 4, May 2006, pp. 495-505.
Stern, MD., "In vivo evaluation of microcirculation by coherent light scattering," Nature, 254(5495): 56-58 (1975).
Tay, et al., "Magnetic Particle Imaging Guided Heating in Vivo using Gradient Fields for Arbitrary Localization of Magnetic Hyperthermia Therapy" ACS Nano. 12(4), Apr. 24, 2018, pp. 3699-3713. <doi:10.1021/acsnano.8b00893>.
Tam, A. C., "Applications of photoacoustic sensing techniques," Reviews of Modern Physics, vol. 58, No. 2, Apr. 1986, pp. 381-431.
Tearney, et al., "Scanning single-mode fiber optic catheter-endoscope for optical coherence tomography" Optics Letters, 21(7): 543-545 (1996).
Tran, et al., "In vivo endoscopic optical coherence tomography by use of a rotational microelectromechanical system probe" Optics Letters, 29(11): 1236-1238 (2004).
Treeby B. E., et al., "Photoacoustic tomography in absorbing acoustic media using time reversal," Inverse Probl. (2010) 26(11), pp. 1-20.
Tu, et al., "Self-propelled supramolecular nanomotors with temperature-responsive speed regulation," Nat. Chem. 9, 480 (2016).
Van Essen, et al., "An Integrated Software Suite for Surface-based Analyses of Cerebral Cortex" Journal of the American Medical Informatics Association, vol. 8, No. 5, Sep./Oct. 2001, pp. 443-459.
Velasco, E., "Ultrafast Camera Takes 1 Trillion Frames Per Second of Transparent Objects and Phenomena" [Webpage] Caltech, California Institute of Technology, Jan. 17, 2020, pp. 1-2. <URL:https://www.eurekalert.org/pub_releases/2020-01/ciot-uct012120.php>.

(56) References Cited

OTHER PUBLICATIONS

Viator et al., "Design testing of an endoscopic photoacoustic probe for determination of treatment depth after photodynamic therapy" Proceedings of SPIE in Biomedical Optoacoustics II, 4256: 16-27 (2001).

Vilela, et al., "Medical imaging for the tracking of micromotors," ACS Nano 12, (2018) pp. 1220-1227.

Wang, et al., "Ballistic 2-D Imaging Through Scattering Walls Using an Ultrafast Oplical Kerr Gale," Science, vol. 253, Aug. 16, 1991, pp. 769-771.

Wang, et al., "Biomedical Optics, Principles and Imaging," Wiley-Interscience, A John Wiley & Sons, Inc., (2007) p. 7.

Wang, et al., "Fabrication of micro/nanoscale motors" Chem. Rev. 115, (2015) pp. 8704-8735.

Wang, B. et al., "Recent progress on micro- and nano-robots: towards in vivo tracking and localization" Quantitative Imaging in Medicine and Surgery, 2018, vol. 8, No. 5, pp. 461-479. <DOI: 10.21037/qims.2018.06.07>.

Wang, L. et al., "Grueneisen relaxation photoacoustic microscopy," Physical Review Letters 113 174301 (Oct. 24, 2014).

Wang, L. V & Yao, J., "A practical guide to photoacoustic tomography in the life sciences," Nat. Methods 13, 627-638 (Jul. 28, 2016).

Wang, L. V., "Multiscale photoacoustic microscopy and computed tomography," Nat. Photon. 3, 503-509 (Aug. 29, 2009).

Wang, L. V.; "Mechanisms of ultrasonic modulation of multiply scattered coherent light: an analytic model," Physical Review Letters 87(4) 043903-(1-4) (Jul. 23, 2001).

Wang, L. V.; "Prospects of photoacoustic tomography," Medical Physics 35(12), Nov. 19, 2008, pp. 5758-5767.

Wang, L., et al., "Single-cell label-free photoacoustic flowoxigraphy in vivo," Proceedings of the National Academy of Sciences 110(15) 5759-5764 (Apr. 9, 2013).

Wang, L., et al., "Ultrasonically encoded photoacoustic flowgraphy in biological tissue," Physical Review Letters 111(20), 204301 (Nov. 15, 2013).

Wang, L.V., Hu, S. "Photoacoustic Tomography: in vivo imaging from organelles to organs," Science 335, 1458-1462 (Mar. 23, 2012).

Wang, X. D., et al., "Noninvasive laser-induced photoacoustic tomography for structural and functional in vivo imaging of the brain," Nature Biotechnology 21(7) 803-806 (Jul. 2003).

Wang, et al., "MCML—Monte Carlo modeling of light transport in multi-layered tissues" Computer Methods and Programs in Biomedicine, vol. 47, No. 2, Jul. 1995, pp. 131-146.

Wang et al., "Three-dimensional laser-induced photoacoustic tomography of mouse brain with the skin and skull intact," Optics Letters, 28(19): 1739-1741 (2003).

Wang et al., "Noninvasive photoacoustic angiography of animal brains in vivo with near-infrared light and an optical contrast agent" Optics Letters, 29(7): 730-732 (2004).

Wang, et al., "Intravascular Photoacoustic Imaging" IEEE J Quantum Electronics, 16(3): 588-599 (2010).

Wang, et al., "Nano/microscale motors: biomedical opportunities and challenges," ACS Nano 6, (2012) pp. 5745-5751.

Wetzel, et al., "Imaging molecular chemistry with infrared microscopy," Science, New Series, vol. 285, No. 5431, Aug. 20, 1999, pp. 1224-1225.

Wong, T. et al., "Fast label-free multilayered histology-like imaging of human breast cancer by photoacoustic microscopy," Sci. Adv. 3, 1602168 (May 17, 2017).

Wong, T. et al., "Label-free automated three-dimensional imaging of whole organ by microtomy-assisted photoacoustic microscopy," Nat. Comm. 8, (Nov. 9, 2017).

Wu, Z., et al., "A microrobotic system guided by photoacoustic computed tomography for targeted navigation in intestines in vivo," Science Robotics 4(32) eaax0613 (Jul. 24, 2019).

Wu, D., et al., "In vivo Mapping of Macroscopic Neuronal Projections in the Mouse Hippocampus using High-resolution Diffusion MRI," Neuroimage 125, Jan. 15, 2016, pp. 84-93.

Xia, J., et al., "Photoacoustic tomography: principles and advances," Electromagn. Waves 147, 1 (2014; available in PMC Jan. 30, 2015).

Xia, J., et al., "Wide-field two-dimensional multifocal optical-resolution photoacoustic-computed microscopy," Opt. Lett. 38(24), Dec. 15, 2013, pp. 5236-5239.

Xu, et al., "Photoacoustic Imaging in Biomedicine," Review of Scientific Instruments, American Institute of Physics, vol. 77 (2006) pp. 041101 1-041101 22.

Xu, et al., "Rhesus monkey brain imaging through intact skull with thermoacoustic tomography," IEEE Trans. Ultrason. Ferroelectr. Freq. Control, vol. 53, No. 3, Mar. 2006, pp. 542-548.

Xu, M. H.; Wang, L. V.; "Time-domain reconstruction for thermoacoustic tomography in a spherical geometry," IEEE Transactions on Medical Imaging 21(7) 814-822 (Jul. 2002).

Xu, M. H.; Wang, L. V.; "Universal back-projection algorithm for photoacoustic computed tomography," Physical Review E 71(1) 016706-(1-7) (Jan. 19, 2005).

Xu, S., et al., "Thermal expansion of confined water," Langmuir 25, 5076-5083 (2009).

Xu, X. et al., "Time-reversed ultrasonically encoded optical focusing into scattering media," Nature Photonics 5(3) 154-157 (Jan. 16, 2011).

Xu, Y.; Wang, L. V.; "Time reversal and its application to tomography with diffracting sources," Physical Review Letters 92(3) 033902-(1-4) (Jan. 23, 2004).

Xu et al. "Time Reversal Ultrasound Modulated Optical Tomography Using a BSO Phase Conjugate Mirror," poster presented at SIPE Conference 7177 on Jan. 26, 2009, 1 page.

Yadlowsky, et al., "Multiple scattering in optical coherence microscopy" Applied Optics, vol. 34, No. 25 (1995) pp. 5699-5707. <doi.org/10.1364/AO.34.005699>.

Yan, et al., "Multifunctional biohybrid magnetite microrobots for imaging-guided therapy" Yan et al., Sci. Robot. 2, eaaq1155, Nov. 22, 2017, pp. 1-14.

Yang, "Optical coherence and Doppler tomography for monitoring tissue changes induced by laser thermal therapy—An in vivo feasibility study" Review of Scientific Instruments, vol. 74, No. 1, Jan. 2003, p. 437-440.

Yang, J. M. et al., "Simultaneous functional photoacoustic and ultrasonic endoscopy of internal organs in vivo," Nature Medicine 18(8) 1297-1303 (Aug. 2012).

Yang, J., et al., "Motionless volumetric photoacoustic microscopy with spatially invariant resolution," Nature Communications 8(1) 780 (Oct. 3, 2017).

Yang, et al., "Novel biomedical imaging that combines intravascular ultrasound (IVUS) and optical coherence tomography (OCT)" IEEE International Ultrasonics Symposium, Beijing, China, Nov. 2-5, 2008, pp. 1769-1772.

Yang, et al., "Time-reversed ultrasonically encoded optical focusing using two ultrasonic transducers for improved ultrasonic axial resolution" Journal of Biomedical Optics 18(11), 110502 (Nov. 2013) pp. 110502-1-110502-4.

Yang, et al., "The grand challenges of science robotics," Science Robotics 3, Jan. 31, 2018, eaar7650, pp. 1-14.

Yang, J.M., et al., "Focusing light inside live tissue using reversibly switchable bacterial phytochrome as a genetically encoded photochromic guide star" Science Advances 5(12) (2019) pp. 1-9.

Yao, et al., "Monte Carlo simulation of an optical coherence tomography signal in homogeneous turbid media" Phys. Med. Biol. 44(9), Jul. 8, 1999, pp. 2307-2320.

Yao, et al., "Absolute photoacoustic thermometry in deep tissue," Opt. Lett. 38, 5228-5231 (2013).

Yao, et al., "In vivo label-free photoacoustic microscopy of cell nuclei by excitation of DNA and RNA," Opt. Lett. 35, 4139-4141 (2010).

Yao, et al., "Optimal ultraviolet wavelength for in vivo photoacoustic imaging of cell nuclei," J Biomed. Opt. 17, 056004 (2012).

Yao, et al., "Photoimprint photoacoustic microscopy for three-dimensional label-free sub-diffraction imaging," Physical Review Letters 112(1) 014302 (Jan. 10, 2014).

Yao, L. et al., "Multiscale photoacoustic tomography using reversibly switchable bacterial phytochrome as near-infrared photochromic probe," Nature Methods 13(1) 67-73 (Jan. 2016).

(56) References Cited

OTHER PUBLICATIONS

Yao, L. et al., "High-speed label-free functional photoacoustic microscopy of mouse brain in action," Nat. Methods 12(5), 407-410 (May 12, 2015).

Yao, L. et al., "Photoacoustic microscopy: superdepth, superresolution, and superb contrast", IEEE Pulse 6, 34-7 (May 13, 2015).

Yaqoob, et al., "Methods and application areas of endoscopic optical coherence tomography" Journal of Biomedical Optics, 11(6): 063001. 1-063001.19 (2006).

Yavuz, M. S., et al., "Gold nanocages covered by smart polymers for controlled release with near-infrared light," Nature Materials 8(12) 935-939 (Nov. 1, 2009).

Yin, et al., "Agarose particle-templated porous bacterial cellulose and its application in cartilage growth in vitro" Acta Biomater. Jan. 12, 2015, pp. 129-138. <doi:10.1016/j.actbio.2014.10.019>.

Yodh et al., "Functional Imaging with Diffusing Light" Biomedical Photonics Handbook, 2003, Ch. 21, pp. 45, CRC Press, Boca Raton.

Yodh, et al. "Spectroscopy and Imaging with Diffusing Light" Physics Today 48(3), Mar. 1995, pp. 34-40.

Zeff, et al., "Retinotopic mapping of adult human visual cortex with high-density diffuse optical tomography" PNAS, vol. 104, No. 29, Jul. 17, 2007, pp. 12169-12174.

Zemp, et al., "Realtime photoacoustic microscopy in vivo with a 30MHZ ultrasonic array transducer" Optics Express, 16(11): 7915-7928 (2008).

Zhang, C., et al., "Coherent Raman scattering microscopy in biology and medicine," Annu. Rev. Biomed. Eng. 17, 415-445 (2015).

Zhang, D. et al., "Depth-resolved mid-infrared photothermal imaging of living cells and organisms with submicrometer spatial resolution," Sci. Adv. 2, e1600521 (2016).

Zhang, H. F. et al., "Functional photoacoustic microscopy for high-resolution and noninvasive in vivo imaging," Nature Biotechnology 24(7) 848-851 (Jul. 2006).

Zhang, H. F. et al., "In vivo imaging of subcutaneous structures using functional photoacoustic microscopy," Nature Protocols 2(4) 797-804 (Apr. 5, 2007).

Zhang, et al., "Intrinsic Functional Relations Between Human Cerebral Cortex and Thalamus" Journal of Neurophysiology, vol. 100, No. 4, Oct. 2008, pp. 1740-1748.

Zharov, et al., "In vivo photoacoustic flow cytometry for monitor of circulating single cancer cells and contrast agents," Optics Letters, 31(24): 3623-3625 (2006).

Zou, et al., "BOLD responses to visual stimulation in survivors of childhood cancer" NeuroImage, vol. 24, No. 1, Jan. 1, 2005, pp. 61-69.

U.S. Appl. No. 16/946,496, filed Jun. 24, 2020, Gao et al.

U.S. Appl. No. 17/090,752, filed Nov. 5, 2020, Wang et al.

International Search Report and Written Opinion of the International Searching Authority regarding PCT/US2018/032007 dated Aug. 9, 2018; pp. 1-7.

Notice of Allowance dated Jan. 26, 2021 issued in U.S. Appl. No. 14/436,581.

Notice of Allowance dated Feb. 2, 2021 issued in U.S. Appl. No. 16/372,597.

International Preliminary Report on Patentability dated Feb. 25, 2021, issued in Application No. PCT/US2019/046574.

International Preliminary Report on Patentability dated Mar. 18, 2021, issued in Application No. PCT/US2019/049594.

International Search Report and Written Opinion dated Mar. 2, 2021 issued in PCT/US2020/059214.

Arridge, et al., "Accelerated high-resolution photoacoustic tomography via compressed sensing," ArXiv Prepr. ArXiv160500133, 2016, pp. 8908-8940.

Cox, et al., "Artifact trapping during time reversal photoacoustic imaging for acoustically heterogeneous media," IEEE Trans. Med. Imaging, vol. 29, No. 2, (2010) pp. 387-396.

Deán-Ben, et al., "Functional optoacoustic neuro-tomography for scalable whole-brain monitoring of calcium indicators," Light Sci. Appl., vol. 5, No. 12, p. e16201, 2016, pp. 1-7.

Deán-Ben, et al., "Portable spherical array probe for volumetric real-time optoacoustic imaging at centimeter-scale depths," Opt. Express, vol. 21, No. 23, 2013, pp. 28062-28071.

Deserno, M., "How to generate equidistributed points on the surface of a sphere," Polym. Ed, p. 99, 2004, p. 1.

Han, Y. et al., "Three-dimensional optoacoustic reconstruction using fast sparse representation," Opt. Lett., vol. 42, No. 5, (2017) pp. 979-982.

Han, et al., "Optoacoustic image reconstruction and system analysis for finite-aperture detectors under the wavelet-packet framework," J. Biomed. Opt., vol. 21, No. 1, Jan. 2016, pp. 016002-1-016002-9.

Huang, et al., "Full-wave iterative image reconstruction in photoacoustic tomography with acoustically inhomogeneous media," IEEE Trans. Med. Imaging, vol. 32, No. 6, Jun. 2013, pp. 1097-1110.

R. A. Kruger, et al., "Dedicated 3D photoacoustic breast imaging," Med. Phys., vol. 40, No. 11, 2013, pp. 113301-1-113301-8.

Matthews, et al., "Parameterized Joint Reconstruction of the Initial Pressure and Sound Speed Distributions for Photoacoustic Computed Tomography," SIAM J. Imaging Sci., vol. 11, No. 2, (2018) pp. 1560-1588.

Matsumoto, et al., "Label-free photoacoustic imaging of human palmar vessels: a structural morphological analysis," Sci. Rep., vol. 8, No. 1, (2018) p. 786.

Mitsuhashi, et al., "A forward-adjoint operator pair based on the elastic wave equation for use in transcranial photoacoustic computed tomography," SIAM J. Imaging Sci., vol. 10, No. 4, 2017, pp. 2022-2048.

Mitsuhashi, et al., "Investigation of the far-field approximation for modeling a transducer's spatial impulse response in photoacoustic computed tomography," Photoacoustics, vol. 2, No. 1, 2014, pp. 21-32.

Ogunlade, et al., "In vivo three-dimensional photoacoustic imaging of the renal vasculature in preclinical rodent models," Am. J. Physiol.-Ren. Physiol., vol. 314, No. 6, (2018) pp. F1145-F1153.

Pramanik, M., "Improving tangential resolution with a modified delayand-sum reconstruction algorithm in photoacoustic and thermoacoustic tomography," JOSA A, vol. 31, No. 3, (2014) pp. 621-627.

Scholte, et al., "On spatial sampling and aliasing in acoustic imaging" 12th Intern. congress on sound and vibration, Lisbon, Portugal (2005) pp. 1-8.

Schoeder, et al., "Optoacoustic image reconstruction: the full inverse problem with variable bases," Proc. R. Soc. A, vol. 474, No. 2219, (2018) pp. 1-20.

Treeby, et al., "k-Wave: MATLAB toolbox for the simulation and reconstruction of photoacoustic wave fields," J. Biomed. Opt., vol. 15, No. 2, Mar./Apr. 2010, pp. 021314.

Treeby, et al., "Advanced photoacoustic image reconstruction using the k-Wave toolbox," in Photons Plus Ultrasound: Imaging and Sensing 2016, 2016, vol. 9708, p. 97082P.

Tzoumas, et al., "Eigenspectra optoacoustic tomography achieves quantitative blood oxygenation imaging deep in tissues," Nat. Commun., vol. 7, 2016, pp. 1-10.

Wang et al., "Biomedical optics: principles and imaging," Section 12.5; Photoacoustic Tomography, John Wiley & Sons (2012) pp. 288-290.

Wang, K. et al., "Investigation of iterative image reconstruction in three-dimensional optoacoustic tomography," Phys. Med. Biol., vol. 57, No. 17, 2012, p. 5399-5423.

Xu, et al., "Exact frequency-domain reconstruction for thermoacoustic tomography—II: Cylindrical geometry," IEEE Trans. Med. Imaging, vol. 21, No. 7, (2002) pp. 829-833.

Zhou, et al., "Tutorial on photoacoustic tomography," J. Biomed. Opt., vol. 21, No. 6, Jun. 2016, pp. 061007-1-061007-14.

U.S. Appl. No. 17/302,313, filed Apr. 29, 2021, Wang et al.

U.S. Appl. No. 17/302,041, filed Apr. 22, 2021, Wang et al.

Notice of Allowance dated Jun. 23, 2021 issued in U.S. Appl. No. 15/037,468.

Duan, T. et al., "Hybrid Multi-wavelength Photoacoustic Imaging", 40th Annual International Conference of the IEEE Engineering in Medicine and Biology Society (EMBC), Jul. 18, 2018, pp. 4804-4807.

(56) References Cited

OTHER PUBLICATIONS

EP Office Action dated May 11, 2022, in Application No. EP19849860.2.
Extended European Search Report dated Apr. 22, 2022, in Application No. 19849860.2.
Extended European search report dated May 23, 2022, in Application No. EP19857631.6.
International Preliminary Report on Patentability dated Jan. 6, 2022 in PCT Application No. PCT/US2020/070174.
International Preliminary Reporton Patentability dated May 19, 2022, in PCT Application No. PCT/US2020/059214.
International Preliminary Reporton Patentability dated Sep. 2, 2021, issued in Application No. PCT/US2020/019368.
Li, Y. et al., "Multifocal Photoacoustic Microscopy Using a Single-element Ultrasonic Transducer Through an Ergodic Relay", Light: Science & Applications, Jul. 31, 2020, vol. 9, No. 135, pp. 1-7.
Notice of Allowance dated Jan. 5, 2022 issued in U.S. Appl. No. 16/540,936.
U.S. Notice of Allowance dated Oct. 19, 2022 in U.S. Appl. No. 16/560,680.
U.S. Corrected Notice of Allowance dated Nov. 14, 2022 in U.S. Appl. No. 16/540,936.
U.S. Corrected Notice of Allowance dated Oct. 26, 2022 in U.S. Appl. No. 16/560,680.
U.S Corrected Notice of Allowance dated Apr. 27, 2022 in U.S. Appl. No. 16/540,936.
U.S. Corrected Notice of Allowance dated Jun. 2, 2022 In U.S. Appl. No. 16/806,796.
U.S. Non Final Office Action dated Aug. 26, 2022 in U.S. Appl. No. 17/302,313.
U.S. Non-Final Office Action dated May 2, 2022 in U.S. Appl. No. 16/798,204.
U.S Notice of Allowance dated Apr. 19, 2022 in U.S. Appl. No. 16/540,936.
U.S. Notice of Allowance dated Aug. 5, 2022 in U.S. Appl. No. 16/540,936.
U.S. Notice of Allowance dated Feb. 23, 2022 in U.S. Appl. No. 16/806,796.
U.S. Office Action dated Apr. 7, 2022, in U.S. Appl. No. 16/560,680.
U.S. Requirement for Restriction dated Oct. 29, 2021 in U.S. Appl. No. 16/560,680.
Yao, J. et al., "Double-illumination Photoacoustic Microscopy", Optics Letters, Feb. 15, 2012, vol. 37, No. 4, pp. 659-661.
U.S. Final office Action dated Jan. 27, 2023 in U.S. Appl. No. 16/798,204.
U.S. Non-Final office Action dated Jan. 23, 2023 in U.S. Appl. No. 17/302,313.
U.S. Non-Final Office Action dated Mar. 20, 2023 in U.S. Appl. No. 17/302,041.
U.S. Notice of Allowance dated Jan. 26, 2023 in U.S. Appl. No. 16/560,680.

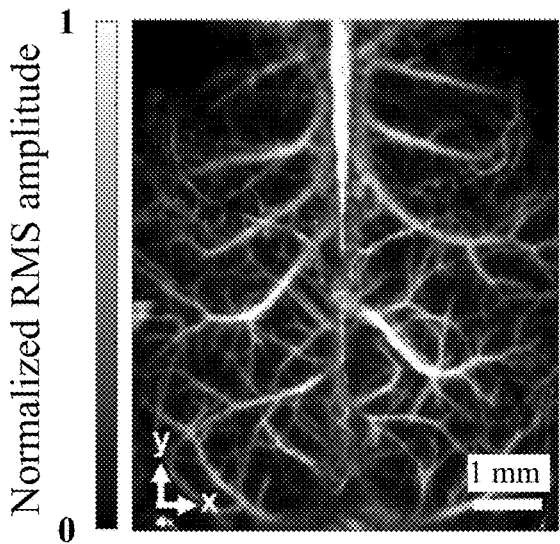
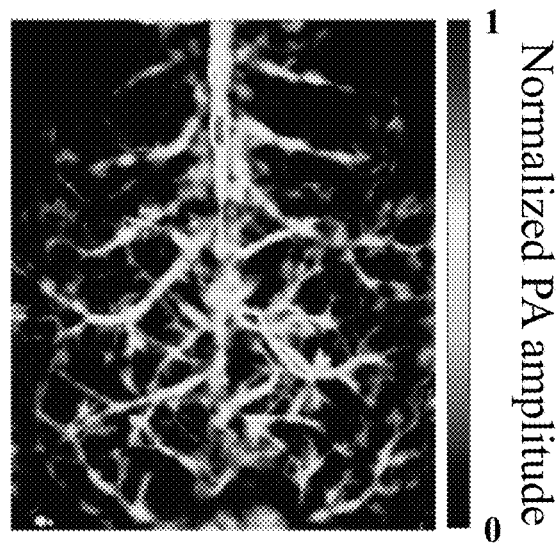
FIG. 5A  FIG. 5B
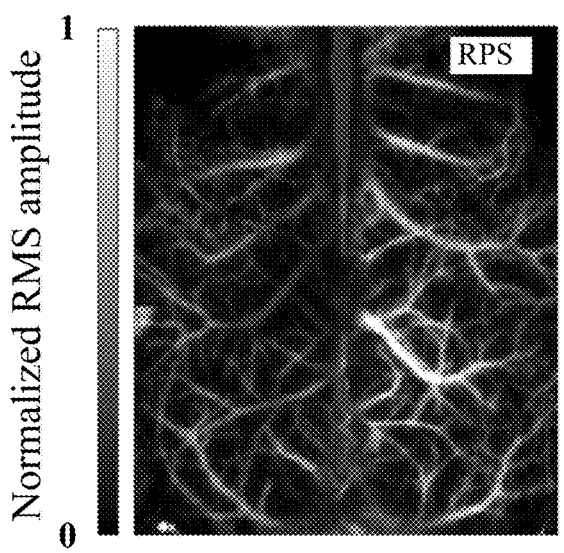
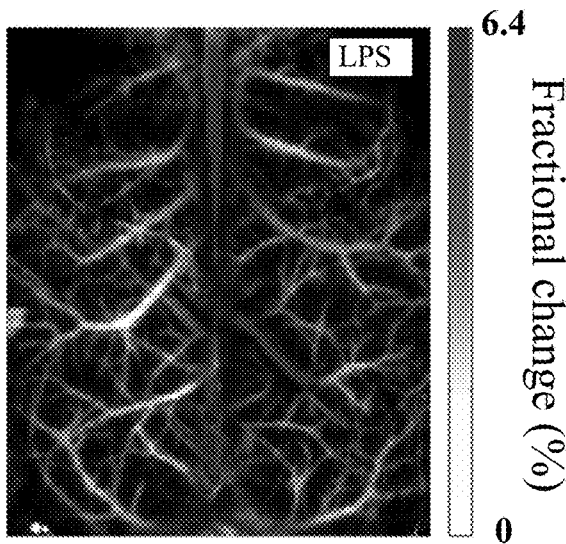
FIG. 5C  FIG. 5D

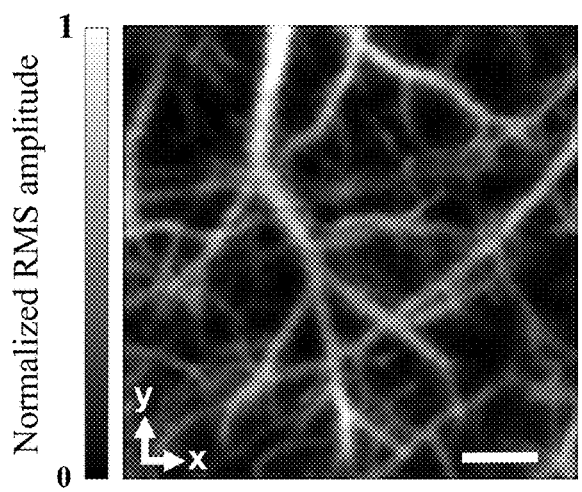
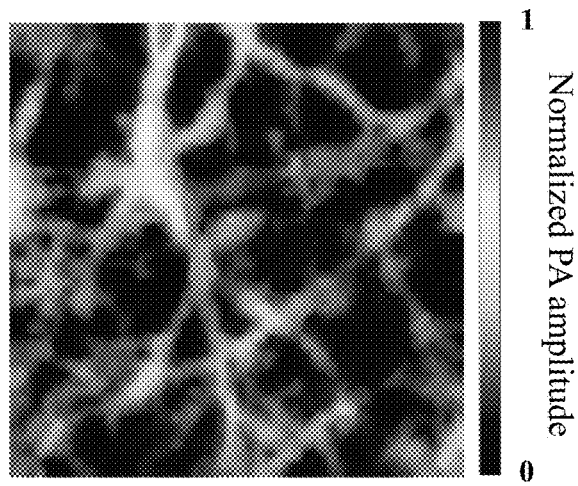
*FIG. 8A*  *FIG. 8B*
Normoxia  Hypoxia
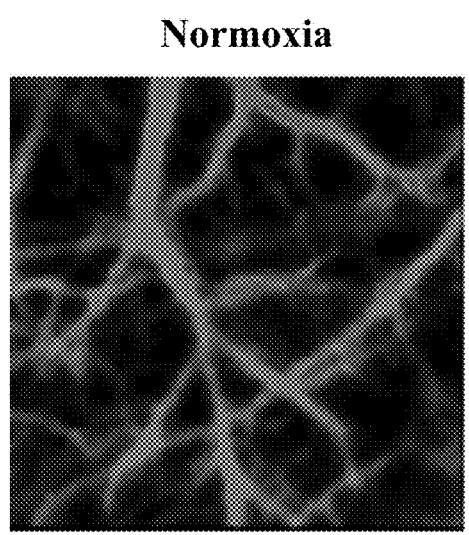
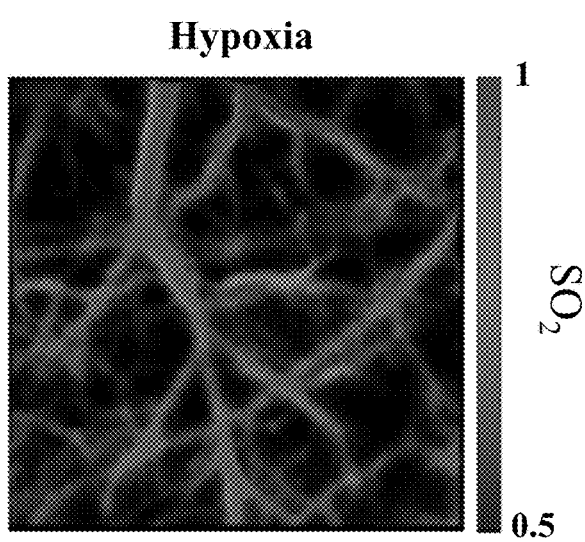
*FIG. 8C*  *FIG. 8D*

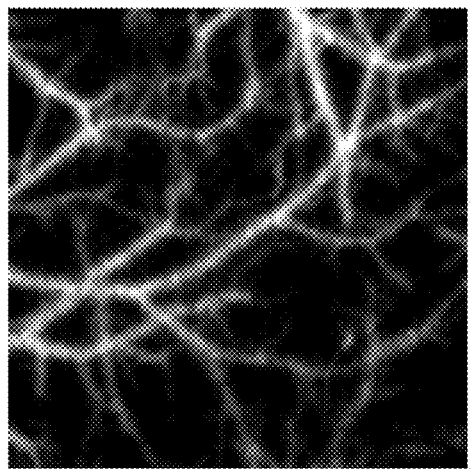
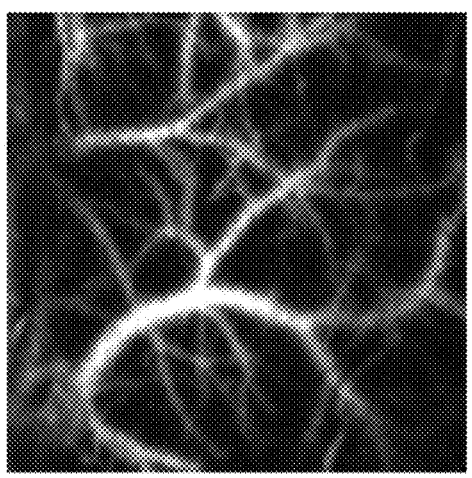
FIG. 10A  FIG. 10B
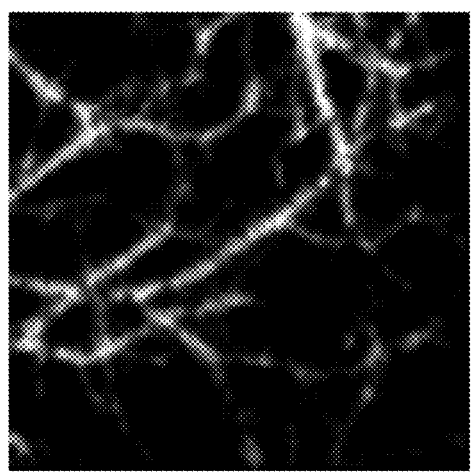
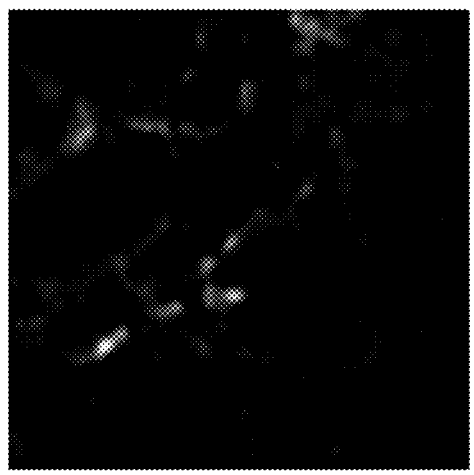
FIG. 10C  FIG. 10D

*FIG. 13A*
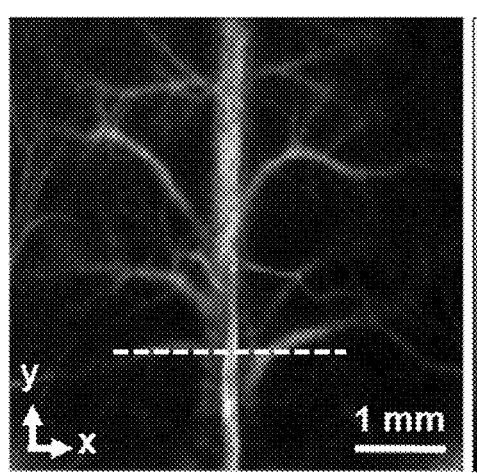
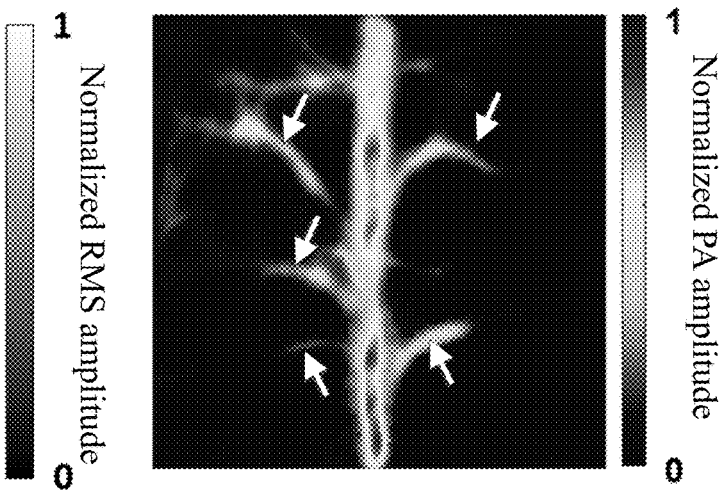
*FIG. 13B*  *FIG. 13C*

SNAPSHOT PHOTOACOUSTIC PHOTOGRAPHY USING AN ERGODIC RELAY

CROSS-REFERENCE TO RELATED APPLICATIONS

This application is a National Stage Entry of International Patent Application No. PCT/US2018/032007, filed on May 10, 2018, which claims the benefit of U.S. Provisional Patent Application Ser. No. 62/503,997, filed on May 10, 2017, entitled SNAPSHOT PHOTOACOUSTIC PHOTOGRAPHY USING AN ERGODIC RELAY, the entire contents of which are hereby incorporated by reference in their entireties.

STATEMENT REGARDING FEDERALLY SPONSORED RESEARCH & DEVELOPMENT

This invention was made with government support under CA186567 awarded by the National Institutes of Health. The government has certain rights in the invention.

BACKGROUND OF THE INVENTION

Optical imaging reveals fundamental biomedical mechanisms by recording fine structures and functions in biological tissues. Modern optical microscopy technologies, such as confocal microscopy, multi-photon microscopy, and optical coherence tomography, form an image via mechanical or optical scanning by detecting photons returned from tissue through scattering or fluorescence. The imaging speed of these existing systems limits their ability to capture fast dynamics over a large field of view (FOV). Conventional optical photography techniques have achieved high imaging speeds by employing two-dimensional optical sensor arrays to acquire snapshot images, but due to strong optical scattering, conventional optical photography can reveal only superficial structures in biological tissue, and it is therefore not well suited for imaging physiological parameters.

Photoacoustic (PA) imaging plays an important complementary role to optical imaging by sensing optical absorption, thereby enabling functional and molecular imaging capabilities. PA signals, unlike signals received by optical imaging systems, are due to photons that are not returned from the tissue during imaging. To date, most PA imaging systems acquire images over extended fields of view by either scanning with a single-element ultrasound transducer or by sensing PA signals using an ultrasound transducer array. Similar to the scanning devices and methods used by other scanning microscopic systems, the single-transducer-based approach to PA imaging has an imaging speed limited by mechanical scanning. Although the transducer-array-based method overcomes the mechanical scanning speed limitation by acquiring multi-channel PA ultrasonic signals in parallel, the use of ultrasound transducer arrays in PA imaging systems is typically accompanied by high system complexity and cost. Moreover, voluminous data acquired from multiple channels may eventually limit the continuous-mode imaging speed due to high demands on data streaming and processing. A need in the art exists for an imaging system suitable for imaging fine structures and functions in biological tissues with enhanced imaging speed without the added complexity and cost of transducer arrays.

BRIEF DESCRIPTION OF THE INVENTION

In one aspect, a photoacoustic imaging system is provided that includes an ergodic relay coupled optically to a light source configured to produce a light pulse and further coupled acoustically to at least one transducer device. The ergodic relay is further configured to couple acoustically and optically to an object to be imaged.

In another aspect, a method of imaging a field of view within an object using a photoacoustic imaging system is provided that includes providing a photoacoustic imaging system with an ergodic relay coupled optically to a light source at a light input face and further coupled acoustically to at least one transducer device. The method also includes acoustically and optically coupling an object to be imaged to a light output face of the ergodic relay. The method further includes directing a diffuse light pulse produced by the light source into the object to be imaged via the light output face. The diffuse light pulse illuminates a field of view within the object. The method additionally includes receiving, via the light output face, a plurality of PA signals from a plurality of positions within the field of view. Each of the plurality of PA signals is produced at one of the plurality of positions within the field of view in response to illumination by the diffuse light pulse. The method further includes directing each of the plurality of PA signals to the at least one transducer device via the ergodic relay. Each of the plurality of PA signals is detected at the at least one transducer device after one of a plurality of corresponding delays after producing the diffuse light pulse. Each delay corresponds to one of the plurality of positions at which one of the pluralities of PA signals is produced. The method also includes forming a PA imaging data set that includes the plurality of PA signals and a corresponding plurality of positions within the field of view, each position corresponding to one of the PA signals, as well as reconstructing an image from the PA imaging data set.

BRIEF DESCRIPTION OF THE DRAWINGS

The following drawings illustrate various aspects of the disclosure.

FIG. 5A is an RMS amplitude projection image of the vasculature of a mouse brain obtained through an intact skull during calibration of the PATER imaging system illustrated in FIG. 1B;

FIG. 5B is a snapshot widefield image of the vasculature of a mouse brain obtained through an intact skull using the PATER imaging system illustrated in FIG. 1A;

FIG. 5C is an image mapping fractional change in PA signal amplitude (shown in red) in response to right paw stimulation superimposed on the RMS amplitude projection image of mouse brain vasculature shown in FIG. 5A;

FIG. 5D is an image mapping fractional change in PA signal amplitude (shown in red) in response to left paw stimulation superimposed on the RMS amplitude projection image of mouse brain vasculature shown in FIG. 5A;

FIG. 8A is an RMS amplitude projection image of the vasculature of a mouse brain obtained through an intact skull during calibration of the PATER imaging system illustrated in FIG. 1B;

FIG. 8B is a snapshot widefield image of the vasculature of a mouse brain obtained through an intact skull using the PATER imaging system illustrated in FIG. 1A;

FIG. 8C is a map of blood oxygenation ($sO_2$) within the vasculature of a mouse brain illustrated in FIGS. 8A and 8B obtained through an intact skull using the PATER imaging system during normoxia;

FIG. 8D is a map of blood oxygenation ($sO_2$) within the vasculature of a mouse brain illustrated in FIGS. 8A and 8B obtained through an intact skull using the PATER imaging system during hypoxia;

FIG. 10A is an RMS amplitude projection image of the vasculature of a first mouse brain (Mouse 1) obtained during calibration of the PATER imaging system illustrated in FIG. 1B;

FIG. 10B is an RMS amplitude projection image of the vasculature of a first mouse brain (Mouse 2) obtained during calibration of the PATER imaging system illustrated in FIG. 1B;

FIG. 10C is a snapshot widefield image of the vasculature of the first mouse brain (Mouse 1) obtained using Mouse 1 snapshot widefield data and Mouse 1 calibration data from FIG. 10A;

FIG. 10D is a snapshot widefield image of the vasculature of the first mouse brain (Mouse 1) obtained using Mouse 1 snapshot widefield data and Mouse 2 calibration data from FIG. 10B;

FIG. 13A is a photograph of a mouse brain with hair removed;

FIG. 13B is an RMS amplitude projection image of the vasculature of the mouse brain corresponding to the photograph of FIG. 13A obtained through an intact scalp during calibration of the PATER imaging system illustrated in FIG. 1B;

FIG. 13C is a snapshot widefield image of the vasculature of the mouse brain corresponding to the photograph of FIG. 13A obtained through an intact scalp using the PATER imaging system illustrated in FIG. 1A;

Figure 1A:
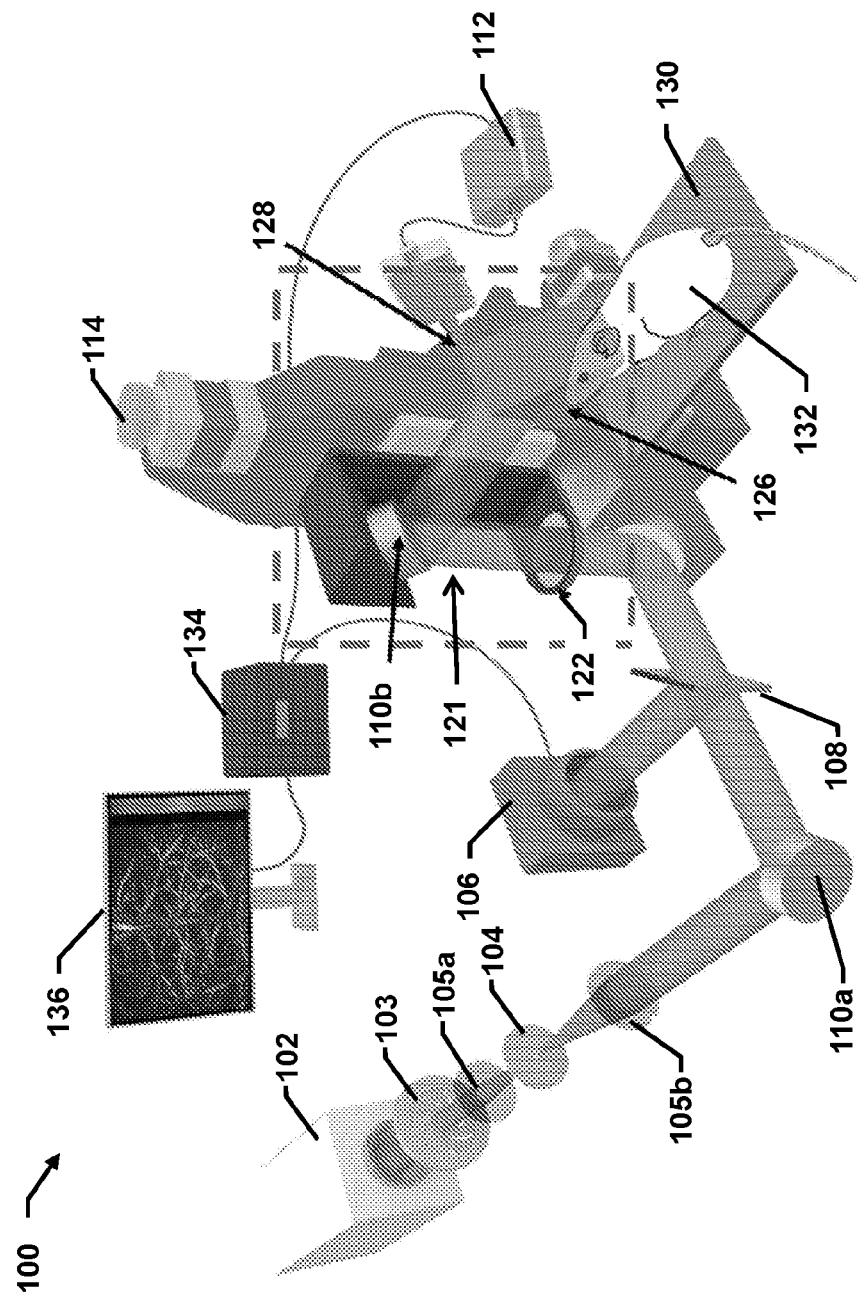
FIG. 1A is a schematic illustration of a photoacoustic topography through an ergodic relay (PATER) imaging system fitted with a diffuser.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION OF THE INVENTION

A photoacoustic imaging technique based on a high-throughput ergodic relay coupled with at least one single-element transducer to capture a widefield image with only one laser shot is disclosed. This method is referred to as photoacoustic topography through an ergodic relay (PATER). In one aspect, the PATER imaging system enables detection of up to 10,000 points over an 8×6 $cm^2$ FOV in parallel with a 2 KHz frame rate and resolved by solving the inverse problem as described herein below, with a lateral resolution of ~210 µm. The PATER imaging system overcomes the limitations of previous PA imaging systems, achieving a higher 2D frame rate, lower data volume, and simpler system configuration than an ultrasound transducer array-based PA tomography system, while maintaining a comparable lateral resolution and FOV. In various aspects, the PATER system makes use of broad light illumination and a single-element unfocused ultrasonic transducer in combination with an ergodic relay to reconstruct widefield snapshot images without scanning. Unlike either OR-PAM or PACT, the PA waves from the entire 2D imaging plane are encoded by the ER and then are decoded and reconstructed through the calibrated impulse responses to yield a widefield image.

The PATER imaging system makes use of an acoustic ergodic relay, also known as an acoustic ergodic cavity, defined herein as a waveguide that allows a sound wave from any input point to reach any one or more output points with distinct delay characteristics. If the ergodic relay is assumed to be lossless and the boundaries are assumed to be perfect reflectors, the acoustic wave at the input point will visit a given output position multiple times with a unique path relative to acoustic waves received at other inputs. Because an acoustic ergodic relay is a linear, temporally shift-invariant system and the ergodic relay's response can be calibrated in advance, ultrasonic waves from multiple PA sources can be detected in parallel using at least one single-element transducer coupled to the ergodic relay. The ultrasonic waves from multiple PA sources detected by the on at least one single-element transducer may be subsequently separated mathematically using analysis methods described herein below.

In various other aspects, the ergodic relay of the PATER system may be coupled to any of a variety of ultrasound transducer devices that include additional transducer elements in excess of the at least one single-element transducer disclosed herein above. The one or more ultrasound transducer devices coupled to the ergodic relay are selected from a variety of transducer devices including, but not limited to: one or more single-element transducers, one or more linear transducer arrays, one or more 2-D transducer arrays, and any combination thereof. Without being limited to any particular theory, the frame rate and/or imaging resolution of the PATER imaging system may be enhanced using transducer devices that include more than one transducer element by providing multiple parallel channels by which the ultrasonic waves from multiple PA sources may be detected and recorded.

The relatively high framing rate of the PATER imaging system, compared to both scanning-based single-transducer PA microscopy systems and array-based PA imaging systems, potentially enable neural activity imaging and other applications previously thought unachievable using previously existing PA imaging systems. In addition, the PATER imaging system may be used to enable biometric authentication of individuals for security applications based on unique internal biometric characteristics of in vivo physiological features such as blood flow, arterial oxygenation, and venous oxygenation that cannot be readily duplicated with existing technologies.

PATER Imaging System

Figure 1B:
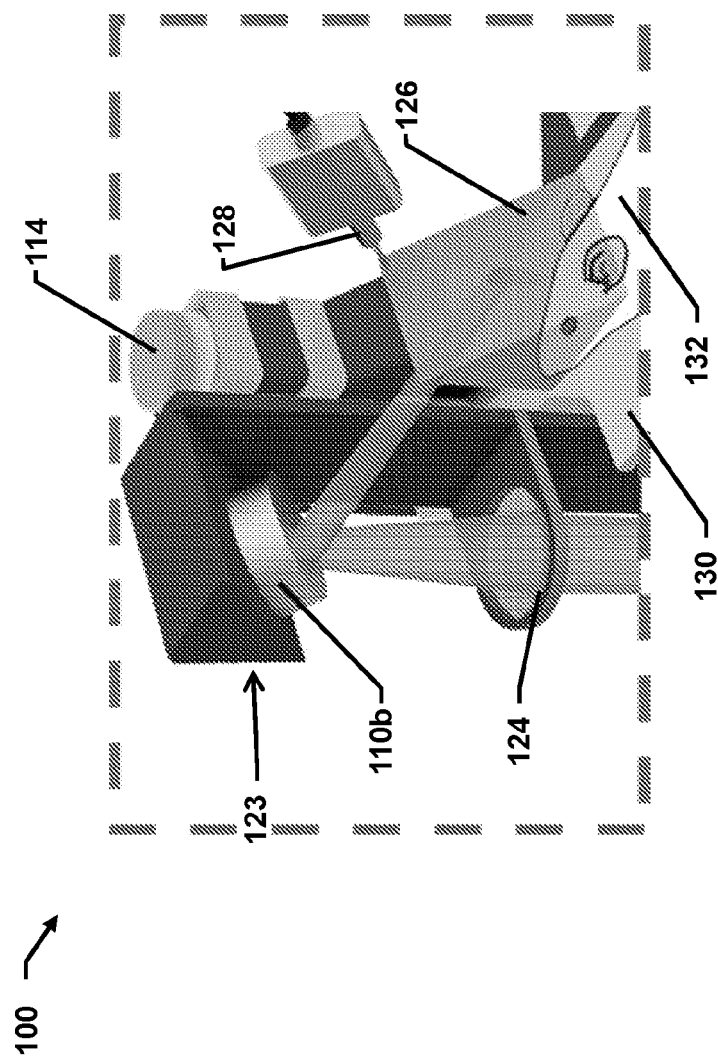
FIG. 1B is the PATER imaging system of FIG. 1A with the diffuser replaced with a plane convex lens.

FIGS. 1A and 1B are schematic illustrations of a Photoacoustic Topography through an Ergodic Relay (PATER) imaging system 100, in one aspect. The PATER imaging system 100 includes a light source 102, such as laser as illustrated in FIG. 1A. In this aspect, the light source/laser 102 is configured to deliver a series of light pulses suitable for photoacoustic imaging as described herein below. Any light source suitable for photoacoustic imaging may be selected for use as the light source 102 of the PATER imaging system 100 without limitation including, but not limited to, pulsed lasers. The light pulse wavelength, duration, and pulse repetition rate (pulses/sec) may be selected based on one of more factors including, but not limited to: selective absorbance of a pulse wavelength by structures of interest within the object 132 to be imaged, scattering of the pulse wavelength through the object 132 to be imaged, sufficient pulse duration to produce detectable PA signals, and any other relevant factor known in the art. By way of non-limiting example, the light source 102 may be a 5-ns pulsed laser beam configured to produce laser pulses at a pulse wavelength of 532 nm (INNOSAB IS8II-E, Edgewave GmbH; 2 KHz pulse repetition rate, 5-ns pulse width).

In various aspects, the light source 102 may be configured to compensate for fluctuations in power supply to the light source/laser 102 that may cause variation in the energy delivered by each light pulse produced by the light source/laser 102. In one aspect, a portion of each light pulses emitted by the light source/laser 102 may directed to a photodiode 106 (DET36A, Thorlabs, Inc.) using a sampling element including, but not limited to a beam sampler (BS) 108 as shown in FIG. 1A to monitor the energy of each light pulse. The energy of each light pulse as measured by a photodiode 106 may be used to correct the measured PA signals for any fluctuations in light energy detected during PATER imaging. The light source/laser 102 may further include additional elements to adjust the amount of light energy delivered to the object 132 to be imaged, including, but not limited to, an aperture 104 that may be contracted or dilated to select a preselected portion of the light pulse produced by the light source/laser 102 for delivery to the object 132 to be imaged using the PATER system 100.

Figure 2A:
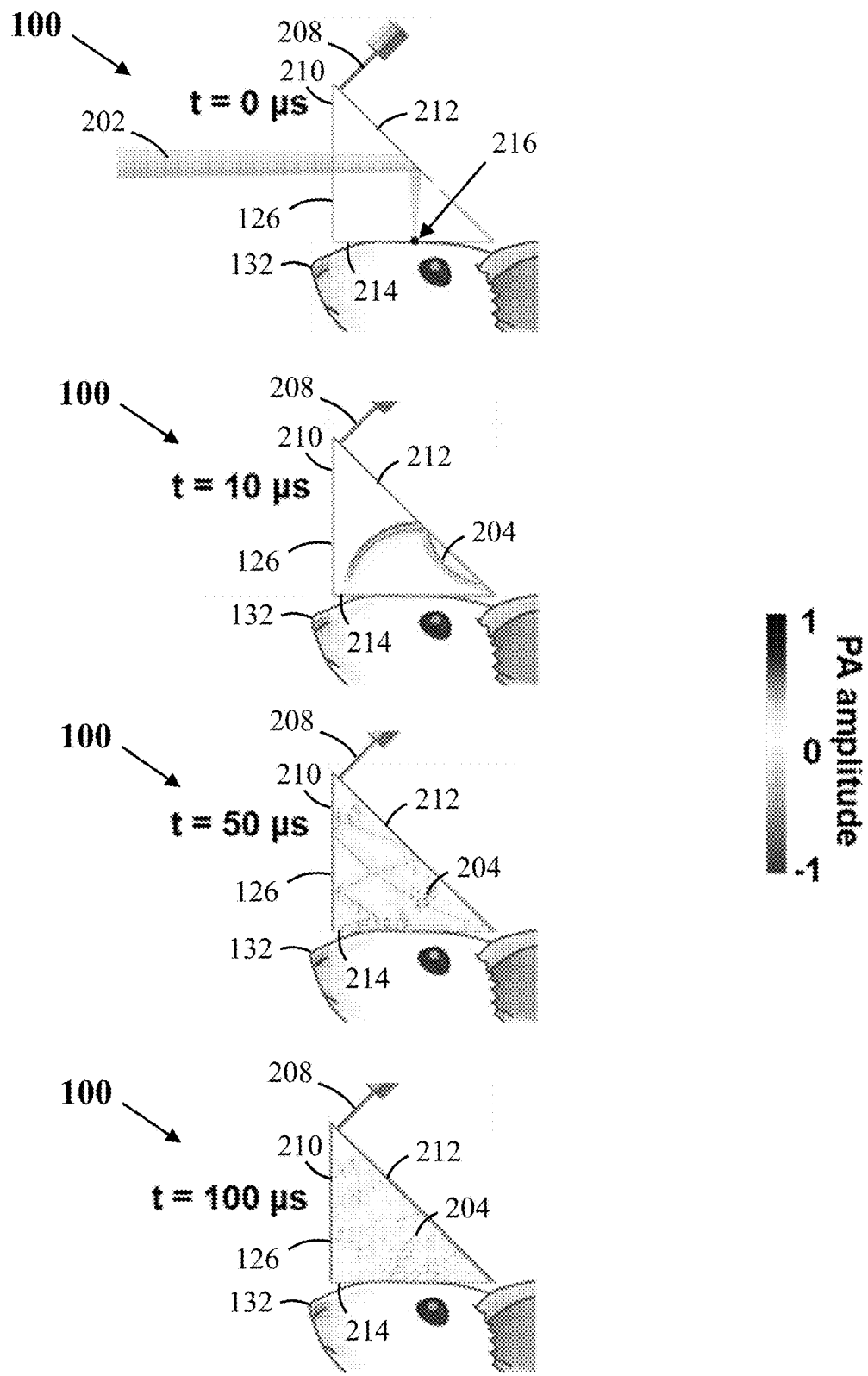
FIG. 2A is a schematic illustration of a method for acquiring calibration data using the PATER imaging system illustrated in FIGS. 1A and 1B.

The series of laser pulses produced by the light source 102 of the PATER imaging system 100 may be directed to selectable focusing elements 122/124 to modify (i.e. narrow or widen) the lateral dimensions of the light pulses delivered to the object 132 to be visualized using the PATER imaging system 100. As disclosed in further detail herein below, in various aspects imaging using the PATER imaging system 100 as disclosed herein is performed in two stages, each stage making use of light pulses with different cross-sectional diameters: a calibration stage in which a narrowly focused laser pulse is scanned across the object 132 to be viewed, and a widefield imaging phase, in which a diffuse (i.e. wide diameter) light pulse illuminates the entire field of view (FOV) 216 (shown in FIGS. 2A and 2B) within the object 132 to be imaged. In this aspect, the selectable focusing element includes a plane convex lens 124 (PCL) 124 to focus the light pulses into a narrow beam 202 as illustrated in FIG. 2A. The selectable focusing element further includes a diffuser 122 (D) to expand the light pulse from the light source/laser 102 into a beam sufficiently broad to illuminate the entire FOV within the object 132 to be imaged. By way of non-limiting example, the diffuser 122 may be an engineered diffuser (EDC-5-A-1r, RPC Photonics, Inc.; 5.5° divergence angle).

In one aspect, each selectable focusing element is positioned separately within the PATER imaging system 100 to conduct each stage of the PATER imaging method. In this aspect, a plane convex lens 124 may be positioned to focus the light pulses during the calibration stage, and the plane convex lens 124 may be replaced by a diffuser 122 during the widefield imaging phase of the PATER imaging method. In another aspect, the selectable focusing elements 122/124 may be mounted on an adjustable stage 114 configured to position each selectable focusing element as needed by adjusting the position, orientation, and/or configuration of the adjustable stage 114. In one aspect, the adjustable stage 114 may be an optical element rotator (OER) (not illustrated). In one aspect, the diffuser 122 (D) and the plane convex lens (PCL) 124 are mounted to the OER.

In an aspect, illustrated in FIGS. 1A and 1B, the selectable focusing elements 122/124 may be provided as switchable modules. In an aspect, a diffuser module 121 may be provided in the form of a C-frame or any other suitable support structure without limitation. The support structure of the diffuser module 121 is configured to support various elements associated with the diffuser 122 in a spacing and alignment suitable for directing a wide light beam to the ERP 126. In one aspect the diffuser 122 and a mirror 110$b$ may be coupled to the support structure of the diffuser module 121, as illustrated in FIG. 1A. In another aspect, a PCL module 123 may be provided to enable the switching of the PATER system 100 from a diffuser 122 to a PCL 124 for performing a calibration phase of imaging. In various aspects, the PCL module 123 may be provided with a support structure similar to the corresponding support structure of the diffuser module 121 to facilitate switching the PATER system 100 between the PCL 124 and the diffuser 122.

As illustrated in FIGS. 1A and 1B, the switchable modules 121 and 123 are configured to align one of the selectable focusing elements 122/124, respectively, with the light pulse such that the selectable focusing element 122/124 can modify the lateral dimension of the light pulse delivered to the object 132 to be focused. In other aspects, additional selectable optical elements may be mounted to the switchable modules 121/123 including, but not limited to: additional plane convex lenses configured to deliver light pulses of varying diameter to the object 132 to be imaged, additional diffusers 122 to expand the light pulse to illuminate different fields of view within the object, apertures, filters such as a polarizing filter, shutters, and any other suitable optical elements known in the art. In an aspect, the switchable modules 121 and 123 may be adjusted manually as needed to implement one of the stages of the PATER imaging method. In another aspect, the switchable modules 121 and 123 may further include an actuator, including, but not limited to a stepper motor or linear actuator, to reposition the optical elements as needed.

In various aspects, the light source/laser 102 is coupled to the selectable focusing element using any one or more known optical coupling elements to deliver the light pulse from the light source/laser 102 to the selectable focusing element. Non-limiting examples of suitable optical coupling elements include optical fibers, lenses, mirrors, and any other known optical coupling elements without limitation. In one aspect, the optical coupling element may include a mirror 110 positioned to reflect the light beam from the light source/laser 102 upward toward the selectable optical element as illustrated in FIG. 1A. In another aspect, the PATER imaging system 100 may include additional optical elements to direct the light pulse from the selectable focusing element to the object 132 including, but not limited to, additional mirrors 110 $b$ as illustrated schematically in FIGS. 1A and 1B.

Referring again to FIGS. 1A and 1B, the PATER imaging system 100 further includes an ergodic relay 126. In an aspect, the ergodic relay 126 receives a plurality of PA signals 204 from a plurality of corresponding positions within the FOV of the object 132, and delivers each of the plurality of PA signals 204 after a signature delay relative to the delivery of the illuminating light pulse. In effect, the ergodic relay 126 encodes the spatial position of a source of a PA signal as a signature delay between the time of delivery of the light pulse and the time at which a PA signal is received from the ergodic relay 126.

In some aspects, the ergodic relay 126 may be any device configured to direct light pulses from the light source 102 into a field of FOV of an object 132, to receive a plurality of PA signals 204 induced by the light pulse within the object 132, to direct each of the plurality of the PA signals 204 along one of a plurality of different pathways through the ergodic relay 126, and to deliver each of the PA signals 204 to one or more transducer devices coupled to the ergodic relay 126, such that each of the plurality of PA signals 204 is delivered at a characteristic delay that is correlated with the position from which the PA signal originated within the object 132.

Figure 15:
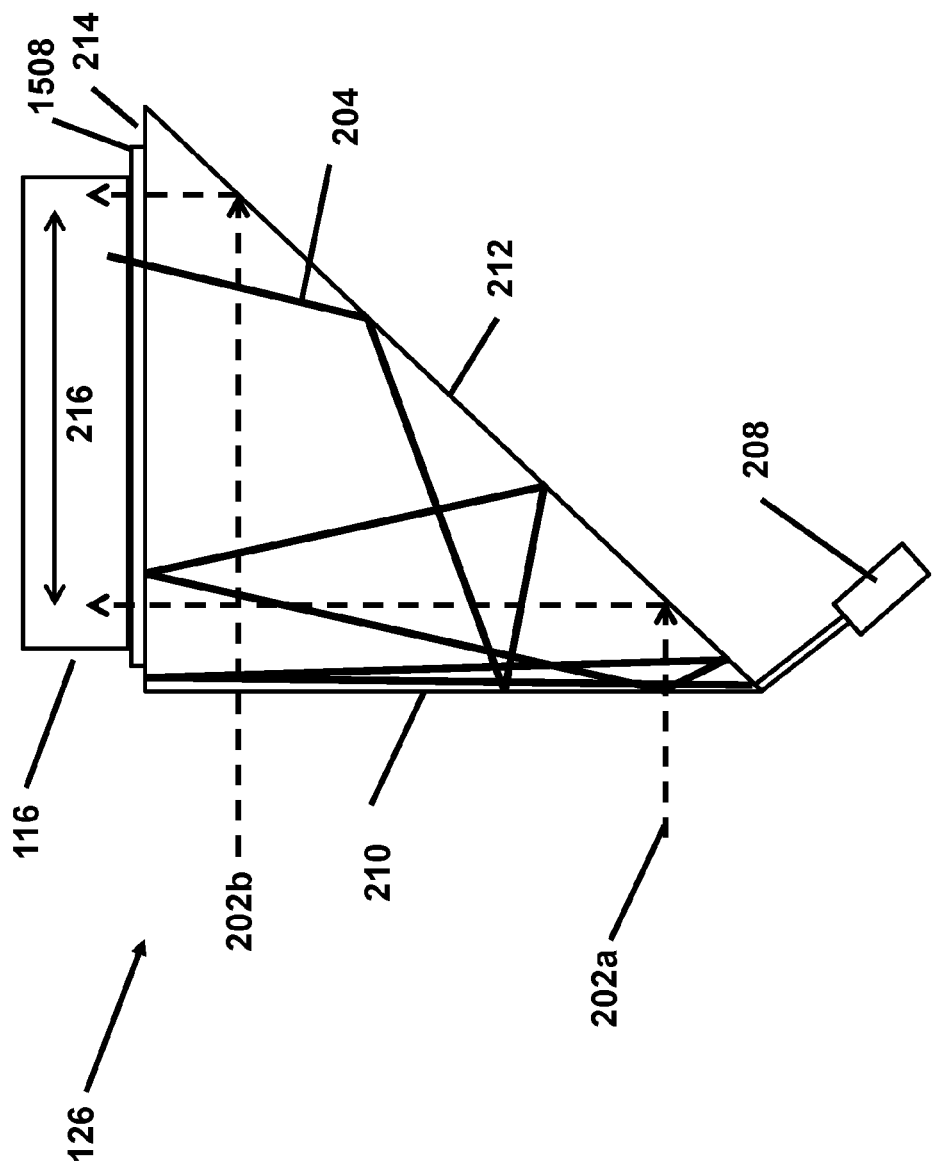
FIG. 15 is a schematic illustration of an ergodic relay prism (ERP)

In some aspects, the ergodic relay 126 may be any device configured to internally reflect light pulses and PA signals 204. In one aspect, the ergodic relay 126 is a right angle prism, such as an ergodic relay prism 126 (ERP) as illustrated in FIGS. 1A and 1B. FIG. 15 is a schematic diagram of an ergodic relay prism 126 in one aspect. In this aspect, the ERP 126 receives each light pulse via a light input face 210 of the ERP 126 as illustrated in FIG. 15. The light pulse may be focused (202) as part of the calibration stage of PATER imaging as described herein below, or it may be diffuse (206, not illustrated) to illuminate a field of view 216 (FOV) as illustrated in FIG. 15 as part of widefield imaging as described herein below. Referring again to FIG. 15, the light beam or beams 202a/202b propagate through the ERP 126 to an angled face 212 that reflects the light beam toward a light output face 214. The light beam exits the ERP 126 at the light output face 214 and enters into the object 132, which is pressed against the light output face 214. In an aspect, the angled face 212 of the ERP 126 may further include a light reflective coating to enhance the reflection of the light pulses to the object 132. Non-limiting examples of suitable reflective coatings include reflective metal coatings.

The light pulses directed into the object 132 via the light output face 214 carry sufficient energy to induce localized heating of objects 132 illuminated by the light beams, resulting in the production of photoacoustic (PA) signals through known methods. PA signals 204 in the form of ultrasound waves induced by the light pulse propagate in all directions away from the object 132 producing the pulse, including in the direction of the light output face 214 of the ERP 126. In an aspect, an acoustic coupling gel may be applied to the object 132 and/or the surface of the light output face 214 of the ERP 126 to enhance the efficiency of transfer of the PA signals 204 into the light output face 214 of the ERP 126 as illustrated in FIG. 15.

PA signals 204 entering the ergodic relay 126 via the light output face 214 propagate across the material of the ergodic relay 126 and are internally reflected due to the discontinuity between the acoustic transmissivity of the material of the ergodic relay 126 and the surrounding air. Each PA signal may reflect internally within the ergodic relay 126 a plurality of times between the internal surfaces of the light input face 210, the angled face 212, and the light output face 214. An exemplary path taken by one PA signal is illustrated in FIG. 15. The internal path of the PA signal within the ergodic relay 126 directs the PA signal to one or more transducer devices coupled to the ergodic relay 126 that detect the incoming PA signal.

In various aspects, each PA signal produced at one position within the FOV 216 of the PATER imaging system 100 is directed from the light output face 214 of the ERP 126 to a transducer element of the one or more transducer devices along a unique path involving multiple internal reflections. Because each unique path is characterized by a unique total path length along the multiple reflections between the light output face 214 and the transducer element, each PA signal takes a slightly different time to travel through the ERP 126. When the entire FOV 216 within the object 132 is illuminated by a single diffuse pulse, the resulting plurality of PA signals 204 induced by the diffuse pulse arrive at the one or more transducer devices at different times due to the different path ways traveled by each PA signal. As a result, the characteristic delay between each PA signal arriving at the one or more transducer devices may be used to determine the position from which each PA signal originated.

Without being limited to any particular theory, the construction of the ERP 126 provides a plurality of pathways along which each PA signal may be transmitted from the object 132 to the one or more transducer devices. Because each pathway is of slightly different length, the transit time of a PA pulse along each pathway is slightly different, causing a delay in the arrival time of different PA signals 204 depending on the individual pathway taken through the ERP 126. Because the individual pathway taken by a PA signal through the ERP 126 depends upon the spatial position at which the PA signal enters the ERP 126, the resulting delay time may similarly be associated with a spatial position within the object 132. As will be described below, each signature delay time for each position within the object 132 may be identified during a calibration stage by illuminating a small region within the object 132 using a narrow-diameter light pulse and determining the delay time between the delivery of the light pulse and the detection of the resulting PA signal. The signature delays over the entire field of view 216 (FOV) within the object 132 may be mapped by scanning the position of the narrow-diameter light pulse and measuring the resulting delay times at each position over the entire FOV 216.

In various aspects, the ERP 126 may be selected from any known ERP device without limitation. In one aspect, the ERP 126 may be selected based on at least one functional parameter including, but not limited to, low acoustic attenuation inside the cavity, high acoustic reflectivity at its boundaries, and high asymmetricity in the geometric relationship between the ERP 126 and the coupled transducer 128 to provide distinctive propagation paths for each acoustic input point. By way of non-limiting example, the ERP 126 may be a right-angle prism made of UV fused silica (PS615, Thorlabs, Inc.; 1.5 cm right-angle edge length, 2,203-kg/m$^3$ density, 73.6-GPa Young's modulus). The ERP in this non-limiting example has a 99.99% normal-incidence acoustic reflectivity by amplitude at the boundary between the prism and air. The acoustic attenuation coefficient is approximately 2.4 nepers/m at 20 MHz, indicating negligible attenuation in the prism over the detected pathlength range.

In various aspects, the one or more transducer devices coupled to the ergodic relay 126 may be any transducer device known in the art without limitation. In various other aspects, the one or more transducer devices may be coupled to the ergodic relay 126 at any one or more positions on the ergodic relay 126 so long as the coupled one or more transducer devices do not interfere with the delivery of the light pulses or the transmittal and internal reflection of the PA signals 204 from the object 132 into the light output face 214. In various aspects, an acoustic coupling medium may be inserted between the ERP 126 and the input of the one or more transducer devices including, but not limited to, a polyester resin material.

In one aspect, the one or more transducer devices may include at least one single-element needle transducer coupled to the right angle prism or other ergodic relay 126; each single-element needle transducer may be coupled to the ergodic relay 126 at a single point including, but not limited to, at a vertex of the prism as illustrated in FIG. 15. In another aspect (not illustrated) the at least one transducer device may include a linear transducer coupled to the right angle prism or other ergodic relay 126 along any face or an edge of the prism including, but not limited to at the edge formed at the intersection of the light input face 210 and the angled face 212 of the right angle prism 126. In other aspects, the at least one transducer device may include 2-D transducer array coupled to the right angle prism or other ergodic relay 126 over at least a portion of a face or edge of the ergodic relay 126 including, but not limited to at least a portion of the angled face 212, at least a portion of a side face of the right angle prism 126, or at least a portion of the light input face 210 or light output face 214 of the right angle prism 126.

By way of non-limiting example, the PATER imaging system 100 illustrated schematically in FIGS. 1A and 1B may include a 5 ns pulsed laser beam configured to produce laser pulses at a pulse wavelength of 532 nm (INNOSAB IS8II-E, Edgewave GmbH; 2 KHz pulse repetition rate, 5 ns pulse width). The PATER imaging system 100 may further include a beam sampler (BS) 108 configured to partially reflect the laser pulses to a photodiode 106 (DET36A, Thorlabs, Inc.) to correct PA signals 204 for any fluctuations in light energy. The PATER imaging system 100 may further include additional optical elements including a mirror 110 *a* (PF10-03-P01, Thorlabs, Inc.) to direct the laser beam toward one of two optical elements (plano-convex lens 105 and diffuser 122) mounted on an optical element rotator (not illustrated) configured to switch the optical element receiving the laser pulse according to the acquisition step plano-convex lens 124 for point-by-point calibration or diffuser 122 for widefield measurements. The PATER imaging system 100 may further include a two-channel digitizer (ATS9350, AlazarTech, Inc.; 50 MS/s sampling rate, 16384 Samples/A-line sample length) configured to record the photoacoustic signals and the photodiode measurements.

In this non-limiting example, the PATER imaging system 100 may further include an ergodic relay 126 in the form of a right-angle prism made of UV fused silica (PS611, Thorlabs, Inc.; 2,203 kg/m3 density, 73.6 GPa Young's modulus), which has a 99.99% normal-incidence acoustic reflectivity by amplitude at the boundary between the prism and air. The acoustic attenuation coefficient is 1.23 nepers/m at 10 MHz, indicating negligible attenuation in the prism, which has a right-angle edge length of 2.5 cm. With such high boundary reflectivity and low acoustic attenuation, the PA signals 204 reflecting within the prism may be assumed to be essentially lossless and sufficiently scrambled, so that the prism forms an acoustic ergodic relay 126 to guide PA signals 204.

Also in this non-limiting example, the PATER imaging system 100 may further include a pin-shaped ultrasound transducer (VP-0.5, CTS Electronics, Inc.; 10 MHz central frequency, 0.5 mm element size or VP-0.5-20 MHz, CTS Electronics, Inc.; 20 MHz central frequency, 56% one-way bandwidth, 0.5 mm element size) placed at a corner of the prism to maximize the distinctions among the received signals from the different input points. In this non-limiting example, an acoustic coupling material including, but not limited to, polyester resin may be positioned between the ergodic relay prism 126 and the ultrasound transducer to act as an ultrasound coupling medium.

PATER Imaging Method

The PATER imaging system 100 obtains images 218 of a field of view 216 of an object 132 according to a PATER imaging method that includes several stages. After positioning the object 132 on the light output face 214 of the ergodic relay prism 126 (ERP), a point-by-point calibration of the PATER system response is conducted during a calibration stage. During the calibration stage, a tightly focused light pulse is scanned over the field of view 216 of the object 132 while recording the resulting PA signals 204 at each position of the light pulse to map the response characteristics of the PATER system 100 for the object 132 including, but not limited to, a signature delay time between light pulse production and the detection of the resulting PA signal at the transducer as a function of position within the FOV 216. In addition to a map of the response characteristics at all positions within the field of view 216 resulting from the calibration, the PA signals 204 obtained during the calibration stage may be reconstructed into an image 218 of the object 132 using known data analysis methods.

Widefield images 218 may be obtained using the PATER imaging system 100 during a subsequent widefield imaging stage. Widefield images 218 are obtained by illuminating the entire FOV 216 of the object 132 using a single diffuse light pulse and recording a plurality of PA signals 204 produced within the FOV 216 of the object 132. The map of the response characteristics of the PATER imaging system 100 obtained during the calibration stage are used to map the plurality of PA signals 204 to corresponding positions within the FOV 216 of the object 132, an images 218 of the FOV 216 may be reconstructed using known methods once the positions from which each PA signal of the plurality of PA signals 204 originated.

Calibration Stage

Figure 16:
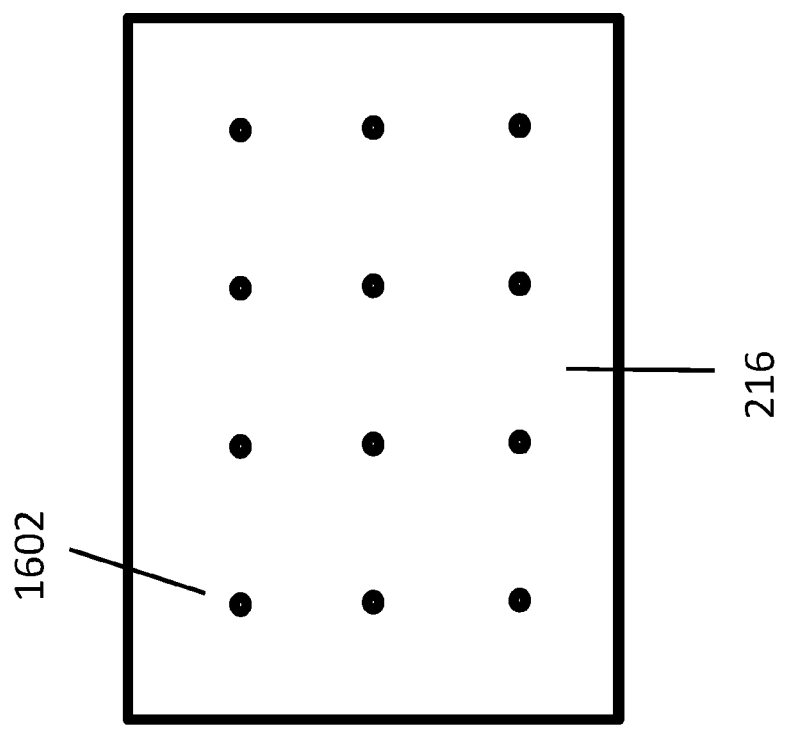
FIG. 16 is a schematic illustration of a scanning pattern associated with a calibration stage of imaging using a PATER imaging system.

The calibration stage of imaging using the PATER imaging system 100 obtains a PA signal via the ergodic relay prism 126 in response to illumination of an isolated small region of the FOV 216 of the object 132 for a plurality of small regions, and then maps the characteristics of each PA signal recorded at each isolated position within the FOV 216 of the object 132 onto the positions of each isolated region. In one aspect, the light pulse may be tightly focused and scanning across a plurality of calibration points 1602 distributed across the FOV 216 of the object 132 as illustrated in FIG. 16.

Figure 17:
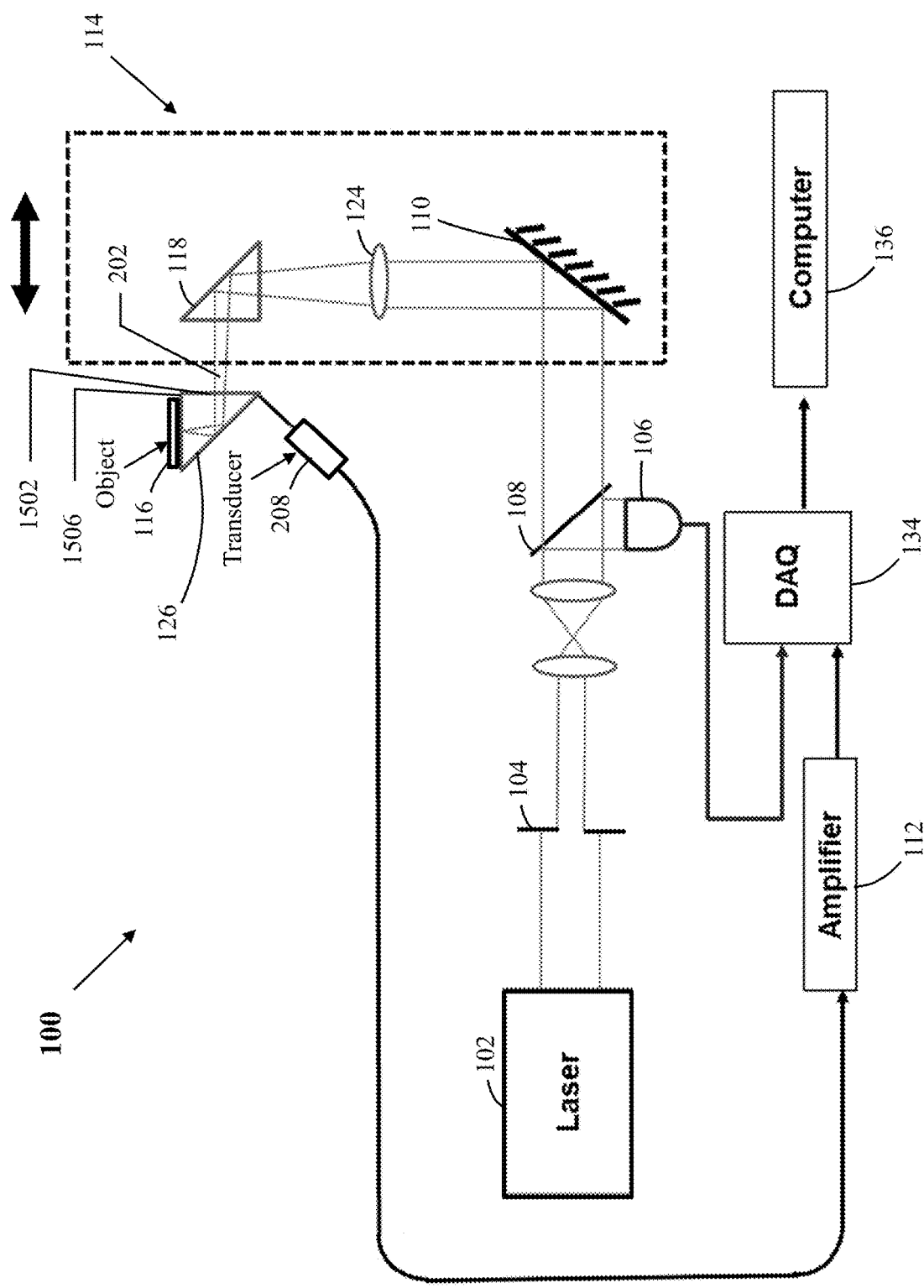
FIG. 17 is a schematic illustration of a PATER imaging system conducting a calibration during a calibration stage.

FIG. 2A and FIG. 17 are schematic illustrations showing the arrangement of various elements of the PATER imaging system 100 during the calibration stage. Referring to FIG. 2A and FIG. 17, the PATER imaging system 100 is configured with a piano-convex lens 124 (PCL) to focus the light pulses produced by the laser 102 into narrow beams 202. Each narrow beam 202 is delivered to the object 116 via the ERP 126 as described herein above, and the PA signal resulting from illumination of this isolated small region is detected by the transducer 208 and recorded to the data acquisition device (DAQ) 134 and computer 136 as illustrated in FIG. 17. The PATER imaging system 100 also includes an amplifier 112 in communication with the DAQ 134 and the transducer 208.

Figure 2B:
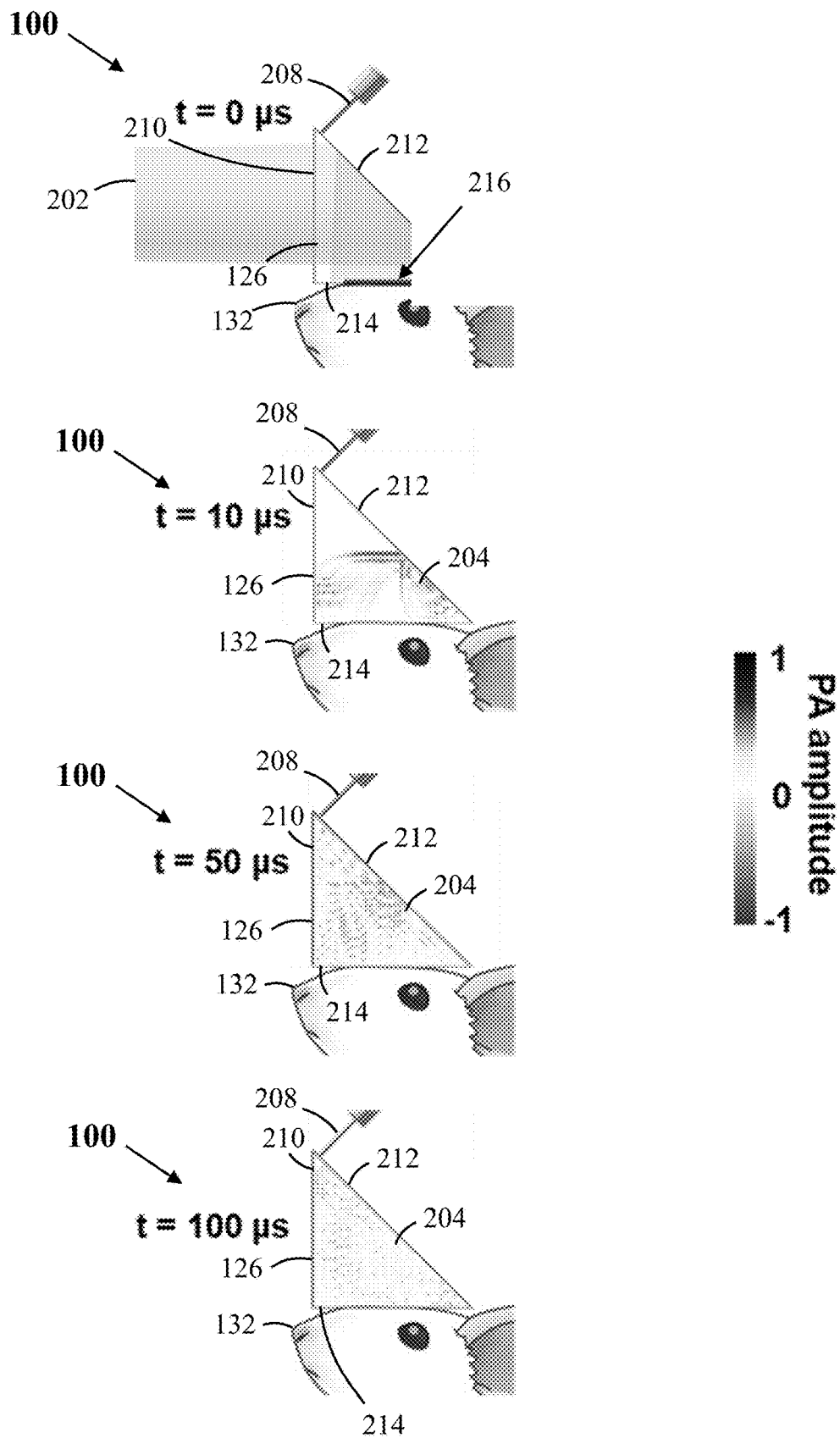
FIG. 2B is a schematic illustration of a method of acquiring snapshot widefield imaging data using the PATER imaging system illustrated in FIG. 1A.
Figure 2C:
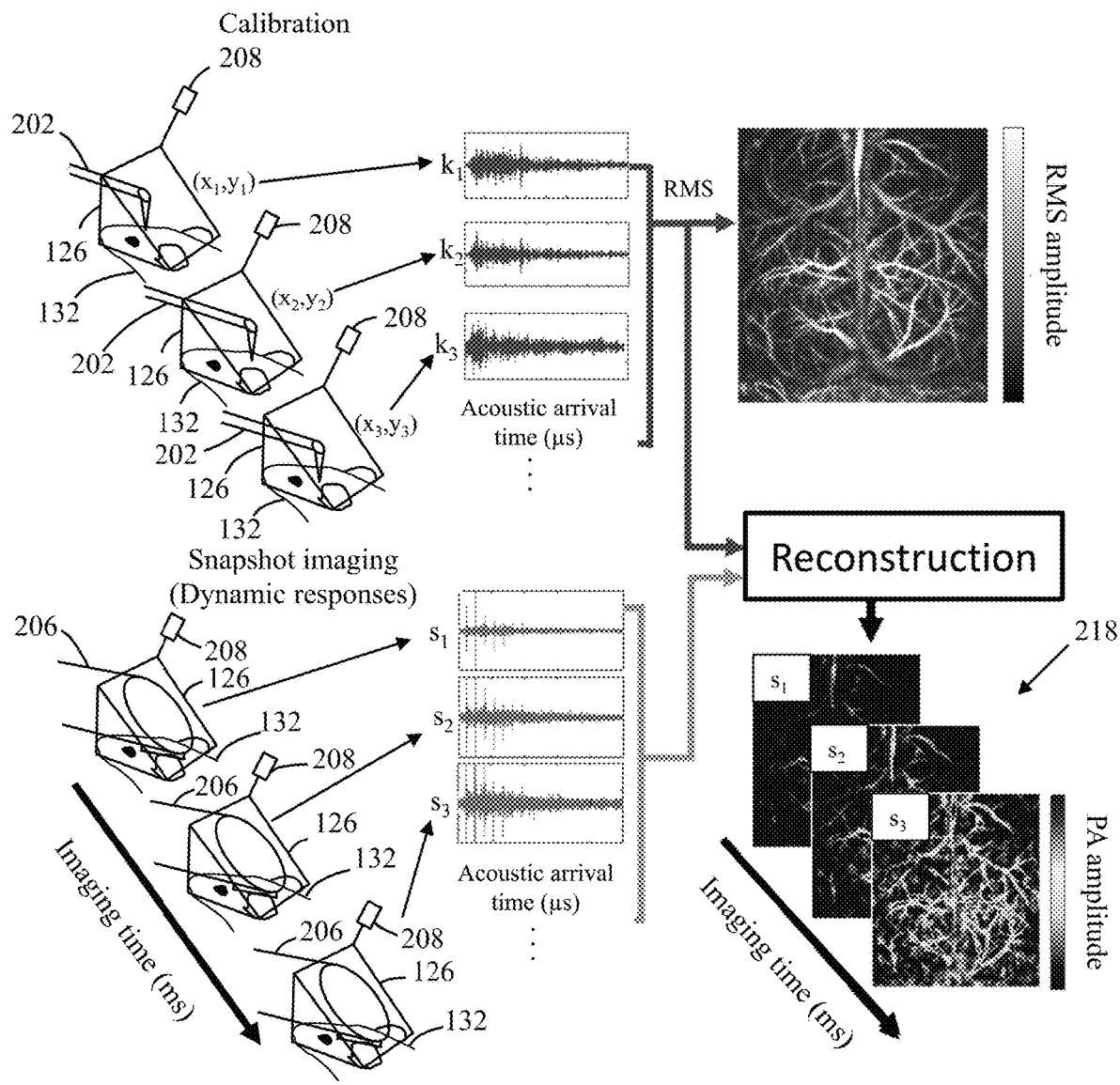
FIG. 2C is a schematic illustration of an image reconstruction method using the calibration data (see FIG. 2A) and snapshot widefield imaging data (see FIG. 2B) obtained using the PATER imaging system illustrated in FIGS. 1A and 1B.

PA signals 204 (not illustrated) from a plurality of calibration points, corresponding to the plurality of isolated illumination regions, are obtained as illustrated schematically in FIG. 2C. In some aspects, the PA signals 204 from a plurality of calibration points may be obtained by scanning one or more elements of the PATER imaging system 100 using one or more motorized stages 114. In one aspect, the ERP 126 and coupling optics such as a right hand prism may be translated relative to the laser 102 and PCL 124 using a 2-axis motorized stage 114 as illustrated in FIGS. 1A and 1B, and FIG. 17. In various other aspects (not illustrated), the laser 102 and PCL 124 may be translated relative to the ERP 126 and coupling optics, the PCL 124 and associated optical elements may be translated relative to the laser 102 and ERB, or any other subset of elements of the PATER imaging system 100 may be translated relative to the remaining elements. In one exemplary aspect, the ERP 126 may be driven by a customized two-axis motorized stage 114 for raster scanning of the laser focus over the light output face 214 of the ERP 126.

Without being limited to any particular theory, because the pulse width of the laser pulse is much shorter than the transducer-defined acoustic period and the focused beam spot is much smaller than the acoustic wavelength, the PA signals 204 from each calibration point received by the ergodic relay prism 126 (ERP) can be approximated as a spatiotemporal delta function. Consequently, each point-by-point calibration measurement provides the impulse response of the ERP 126 for one calibration position (i.e. from one spot on the input surface of the ERP 126).

In conventional PA microscopy (PAM), each PA signal detected by a focused ultrasound transducer has a well-defined propagation direction and can be directly mapped onto a line image. By contrast, each signal detected by the unfocused ultrasound transducer after passing through the ERP 126 contains many acoustic modes. To accommodate the multiple acoustic modes contained within each PA signal from each calibration point, the root-mean-squared (RMS) value of each PA signal was computed to form an RMS amplitude projection image at the calibration points on the light output surface of the ERP 126.

In one aspect, the PA signals 204 from each point i along the raster scan pattern can be measured sequentially as $C_i(t)$, where i=index number of a calibration point detected in response to light pulse input $x_i(t)$ at point i. The measured calibration signal $C_i(t)$ may be stored as a calibration signal C(n), where n is the number of samples obtained over time t.

The RMS value, $X_{i,rms}$, for each calibration point is the root-mean-squared value of the calibration signal C(n), calculated as:

$$X_{i,rms} = \sqrt{\frac{1}{N}\sum_{n=1}^{N}|C(n)|^2} \qquad \text{Eqn. (1)}$$

where N is the number of samples in the calibration signal.

By way of non-limiting example, a point-by-point calibration may be performed on the ergodic relay prism 126 (ERP) by illuminating a small spot within the FOV 216 of the object 132 using a 5 ns pulse focused by a plano-convex lens 124 (LA1433, Thorlabs, Inc.; 150 mm focal length) to a small spot (~30 μm) on the light input face 210 of the ergodic prism 126 (ERP) (see FIG. 15). The optical absorbers within the spot absorb the short-pulsed light energy and convert the light energy delivered by the pulse into heat, resulting in PA signal emission from the spot due to thermoelastic expansion. The PA signals 204 emitted by the spot are propagated through the ergodic relay prism 126 and are subsequently detected by the ultrasound transducer 128 attached to an edge of the ERP 126. By way of another non-limiting example, the laser beam may be focused by a plano-convex lens (LA1509, Thorlabs, Inc.; 2.54-cm diameter, 100-mm focal length) to a ~5 μm spot on the input surface of the ERB 126 that interfaces with the object 132 to be imaged.

The RMS values obtained during the calibration stage are used to process the data obtained during the widefield imaging stage as described herein below. Further, the RMS values may be used to form an RMS projection image of the FOV 216 of the object 132 using a TwIsT algorithm as described herein below.

Widefield Imaging Stage

The widefield imaging stage of imaging using the PATER imaging system 100 obtains a plurality of PA signals 204 via the ergodic relay prism 126 in response to illumination of the entire FOV 216 of the object 132 using a diffuse widefield light pulse 206, and then separates and analyzes the signals originating from different positions within the FOV 216 using the calibration RMS signal values $S_{i,rms}$. The separated PA signals 204 from each position within the FOV 216 are then used to form an image 218 of the FOV 216 within the object 132.

Figure 18:
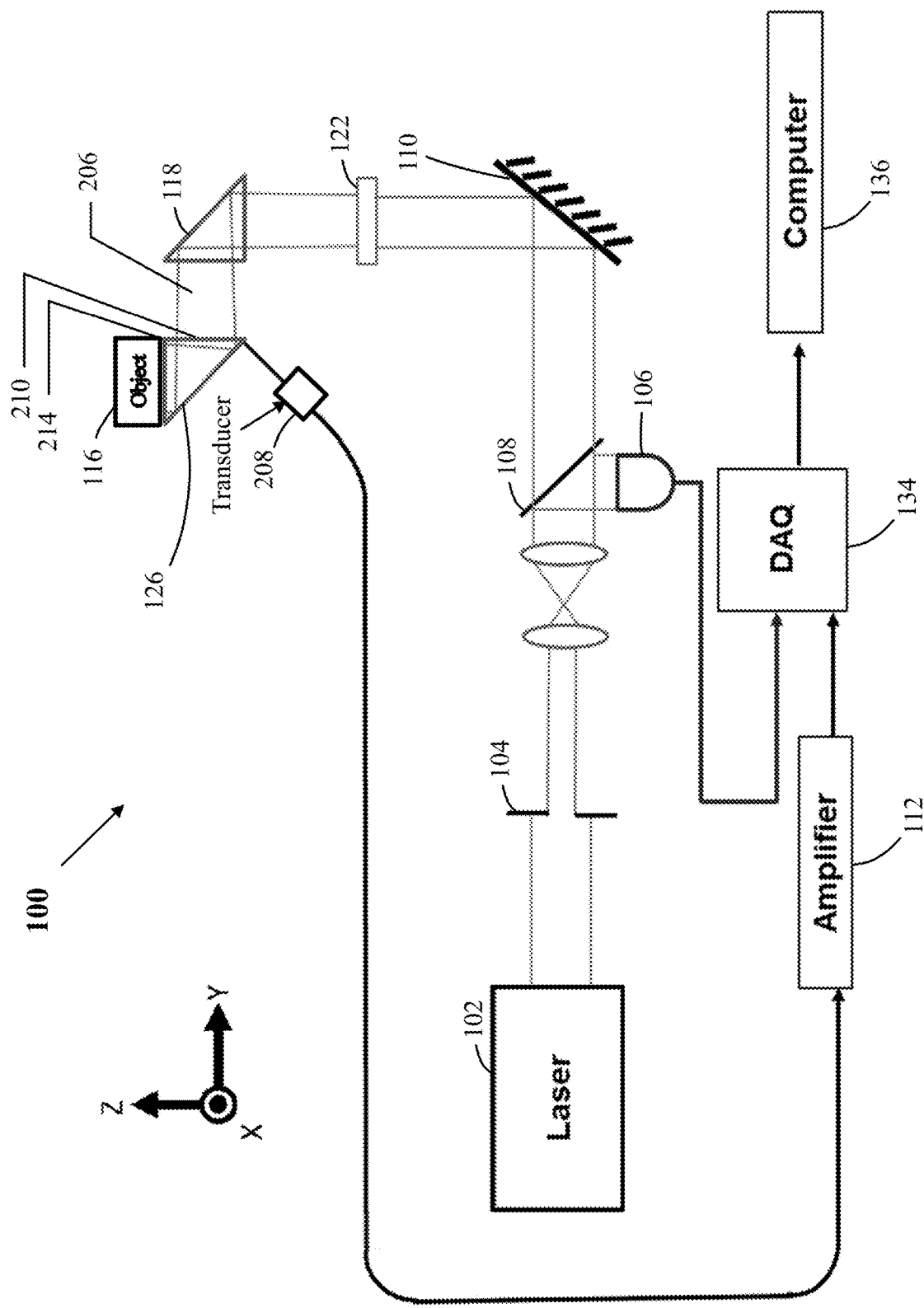
FIG. 18 is a schematic illustration of a PATER imaging system conducting a calibration during a widefield imaging stage.

FIG. 2B and FIG. 18 are schematic illustrations showing the arrangement of various elements of the PATER imaging system 100 during the widefield imaging stage. Referring to FIG. 2B and FIG. 18, the PATER imaging system 100 is configured with a diffuser 122 as the switchable focusing element to expand and homogenize the light beam so it covers the entire FOV 216 on the imaging surface uniformly. Each expanded beam is delivered to the object 132 via the ERP 126 as described herein above, and the PA signal resulting from illumination of the entire FOV 216 of the object 132 is detected by a needle transducer 208 and recorded to the data acquisition device (DAQ) 134 and recorded to a computer 136 as illustrated in FIG. 18. The photoacoustic signals 204 emitted from all of the points within the FOV 216 are recorded in parallel by the same ultrasound needle transducer 208 as illustrated schematically in FIG. 2C. The plurality of PA signals 204 is detected simultaneously as a combined assemblage by the needle transducer 208 as illustrated in FIG. 2C. The signals associated with each calibration point are separated using the calibration data obtained during the calibration stage.

In one aspect, each widefield measurement can be expressed as a linear combination of the responses from all calibrated points:

$$s(t)=\Sigma_i k_i(t)x_i, (i=1,\ldots,n), \qquad \text{Eqn. (2)}$$

where s is the widefield signal, and $k_i$ and $x_i$ are the impulse response and relative optical absorption coefficient from the $i^{th}$ calibrated point, respectively.

Once time t is discretized, Eqn. (1) can be recast in a matrix form, as expressed in Eqn. (2):

$$s=Kx, \qquad \text{Eqn. (3)}$$

where $K=[k_1,\ldots,k_n]$ is the system matrix.

The widefield image 218 is reconstructed by solving the inverse problem of Eqn. (3). A two-step iterative shrinkage/thresholding (TwIST) algorithm was adopted to implement the reconstruction as described herein below.

In another aspect, each PA signal 204 originating from each calibration point may be separated from the combined PA signals 204 recorded during the widefield imaging stage using the RMS values of the calibration signals determined above. In this other aspect, the signal recorded during the widefield imaging stage may be expressed at Eqn. (4):

$$y(t)=\Sigma_i^n a_i s_i(t) \qquad \text{Eqn. (4)}$$

where $a_i$ is an amplitude coefficient defined according to Eqn. (5):

$$a_i \propto \mu_a F \qquad \text{Eqn. (5)}$$

where $\mu_a$ is the light absorbance and F is the fluence of the light pulse.

The inner product from Eqn. (4) may be formed according to Eqn. (6):

$$Y=[\langle y,s_1\rangle,\ldots,\langle y,s_n\rangle] \qquad \text{Eqn. (6)}$$

The amplitude coefficient $a_i$ may be corrected using the root mean squared value of the calibration magnitudes according to Eqn. (7):

$$a_i = \frac{\langle y, s_i\rangle}{s_{i,rms}}, i=1,\ldots,n \qquad \text{Eqn. (7)}$$

where $s_{i,rms}$ is the root mean squared value of the calibration signal magnitude for the $i^{th}$ calibration point.

The calculated coefficients may then be normalized according to Eqn. (8):

$$a'_i = \frac{a_i - \min(a_i)}{\max(a_i)} \quad \text{Eqn. (8)}$$

By way of non-limiting example, the PA signals 204 for each image 218 may be acquired within 164 µs during the widefield imaging stage. In this example, the resulting image 218 is devoid of motion artifacts. Further, because the PATER imaging system 100 does not require scanning to form images 218 in the widefield stage, it is able to achieve a widefield recording rate of up to 6 KHz (typically limited by the laser repetition rate) over an 8×6 mm² FOV. The system's recording rate is 2,000 times greater than that of fast functional PAM, over an eight times larger FOV by area; hence, the rate per FOV area is 8,000 greater. However, each of the system's recorded frames contains up to about 25 times fewer pixels/frame; hence, the throughput (defined herein as the product of frame rate and pixels/frame) is about 80 times higher compared to fast functional PAM.

Image Reconstruction Stage

In various aspects, the RMS calibration values obtained during the calibration stage and the widefield image data may be reconstructed into images 218 of the FOV 216 within the object 132 during an image reconstruction stage of the PATER imaging method. Any known image reconstruction method suitable for photoacoustic imaging may be used without limitation. In one aspect, a two-step iterative shrinkage/thresholding (TwIST) algorithm may be implemented to solve for x as a minimizer of the objective function:

$$\hat{x} = \operatorname{argmin}_x \|y - Kx\|^2 + 2\lambda \Phi_{TV}(x) \quad \text{Eqn. (9)}$$

Here, $\Phi_{TV}(x)$ is the total variation regularization term, and $\lambda$ is the regularization parameter. To avoid computational instability and ensure image quality, RMS values may be used to select valid calibration points to form the system matrix. Calibration points with RMS values lower than twice (6 dB) the noise level were considered as belonging to the background that was too dark to calibrate for, and, therefore, the impulse responses of these points are excluded from the system matrix K in some aspects. This initial check ensures that only the foreground points with sufficient signal-to-noise ratios are considered in the reconstruction. The approach in this aspect holds valid if the background does not merge into the foreground during the experiment.

EXAMPLES

The following examples illustrate various embodiments of the disclosure.

Example 1: Lateral Resolution of PATER Imaging System

To assess the lateral resolution of images obtained using the PATER imaging system 100 described herein above, the following experiments were conducted.

Figure 3A:
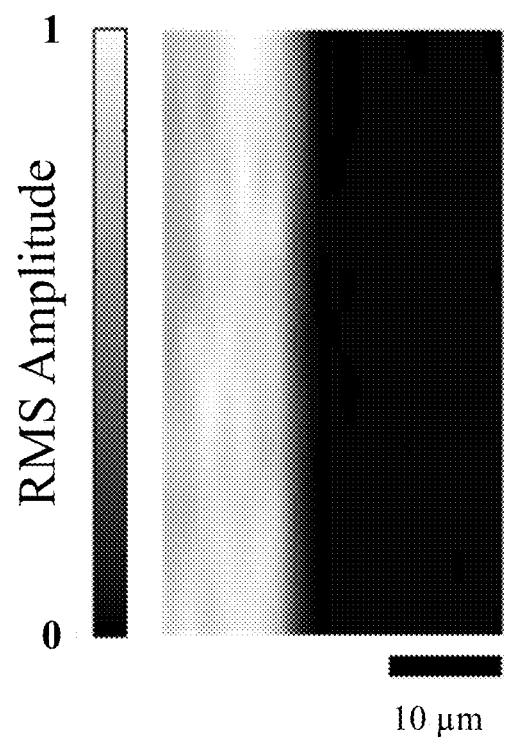
FIG. 3A is an RMS amplitude projection image of a blade edge obtained during calibration of the PATER imaging system illustrated in FIG. 1A.
Figure 3B:
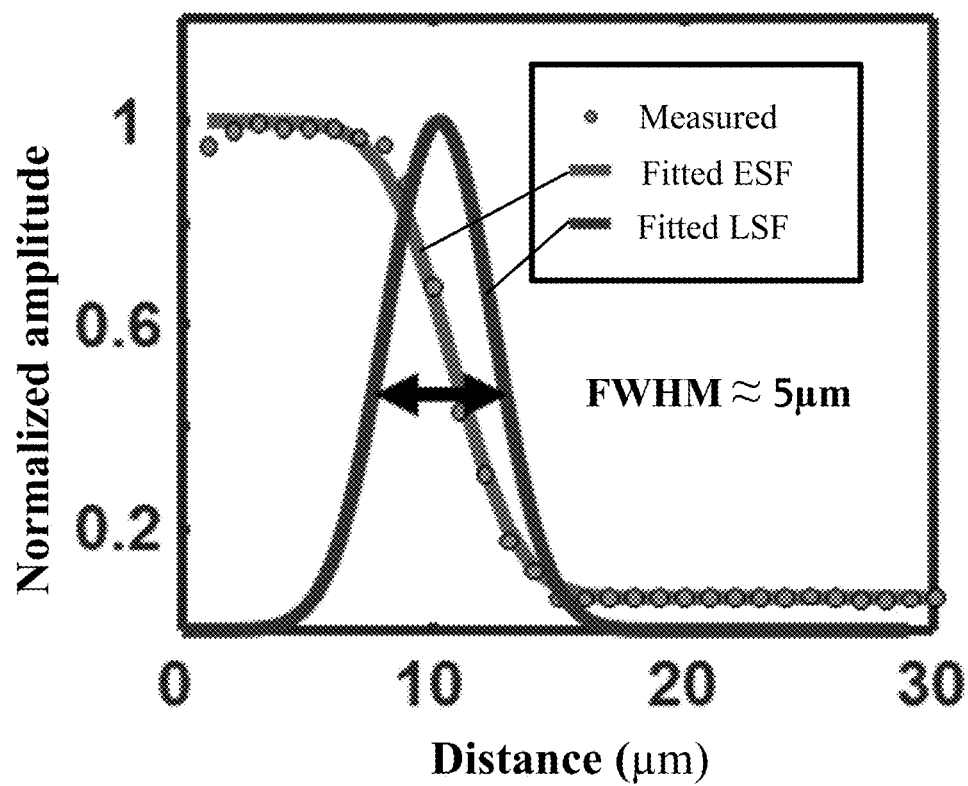
FIG. 3B is a graph summarizing a line-spread function calculated based on the edge-spread function derived from the image of FIG. 3A.

Two physical calibration objects were imaged to quantify the lateral resolution in both calibration and snapshot imaging modes. In calibration mode, the edge of a sharp metal blade was imaged. An RMS amplitude projection of the blade edge is provided in FIG. 3A. The averaged amplitude measurement was fitted to an error function to obtain the edge-spread function (ESF), based on the assumption that the beam profile was Gaussian. A line-spread function (LSF) of the system was calculated by taking the derivative of the fitted ESF. The lateral resolution, measured as the full width at half maximum (FWHM) of the fitted LSF, was 5 µm, matching the diameter of the focused laser spot.

To quantify the lateral resolution of the snapshot widefield image obtained by the PATER imaging system 100 during the snapshot photoacoustic tomography step as described herein above, a phantom calibration body consisting of a pair of laser spot beams projected on to a black acrylic sheet was placed on the imaging plane of the PATER imaging system 100 and snapshot widefield images were obtained at a variety of separation distances between the laser spot pair.

Figure 4A:
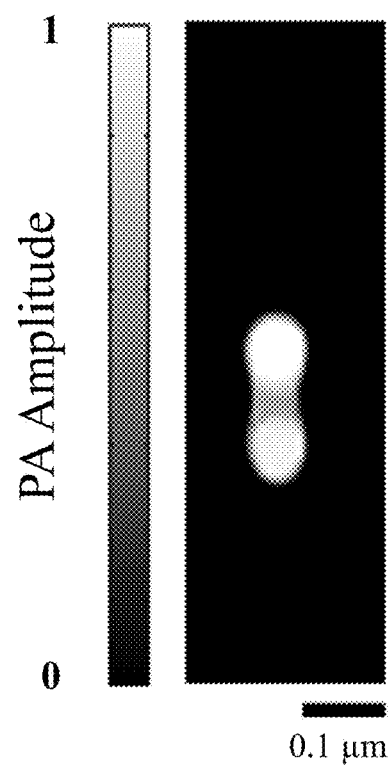
FIG. 4A is an image of two spot beams projected onto a black acrylic sheet obtained as snapshot widefield imaging data using the PATER imaging system.

The black acrylic sheet was selected to provide uniform absorption of the laser spots throughout the FOV 216 of the PATER imaging system 100. Two laser spot beams with beam diameters of about 5 µm were shined on the black acrylic sheet. The first laser spot was held stationary in the center of the black acrylic sheet and the second laser spot was traversed linearly across the black acrylic sheet to intercept the first laser spot while obtaining snapshot widefield images of the black acrylic sheet and spots at various separation distances. The step size for the movement of the second laser spot was 15 µm, and the area of the FOV was 1.5×0.51 mm². FIG. 4A is an example of one of the snapshot widefield images obtained.

Figure 4B:
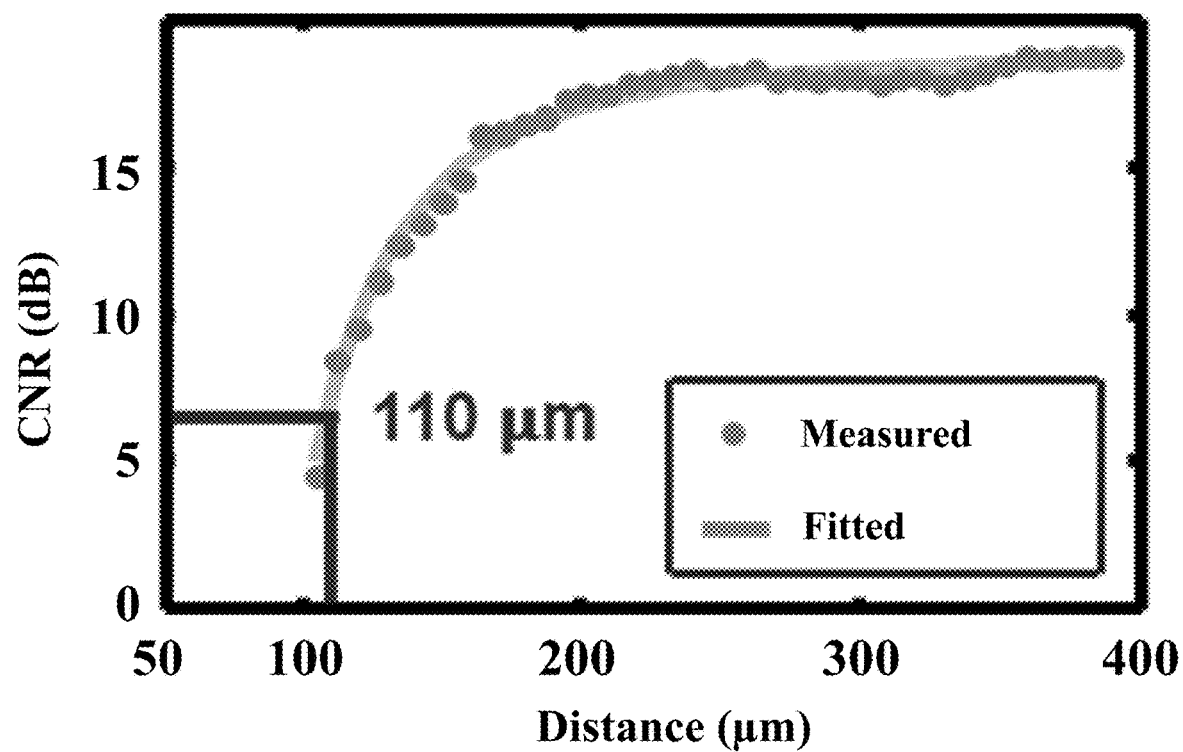
FIG. 4B is a graph summarizing the contrast-to-noise ratio (CNR) of PA signals as a function of separation distance of the two spot beams in the image shown in FIG. 4A.

For each snapshot widefield image of the two laser spots, the contrast-to-noise ratio (CNR) was calculated. FIG. 4B is a graph summarizing the contrast-to-noise ratio (CNR) versus the separation distance between the two laser spots. The lateral resolution, measured as the distance with 6 dB CNR, was approximately 110 µm.

The results of this experiment demonstrated that the PATER imaging system 100 acquired snapshot widefield images at a lateral resolution comparable to the diameter of an arteriole, thereby enabling the imaging of fine structures and functions in biological tissues.

Example 2: Quantification of Compound Concentrations Using PATER Imaging System

The following experiments were conducted to assess the ability of the PATER imaging system 100 to measure concentrations of Evans Blue dye (EB, Sigma-Aldrich, Inc.) in a tube.

A phantom calibration body consisting of two silicone tubes with a 0.65 mm inner diameter placed in parallel was situated within the FOV of the PATER imaging system 100 of Example 1. An EB solution with 0.6% concentration-by-mass was injected into each of the two tubes and a point-by-point calibration was performed as described herein above. Snapshot widefield images of the phantom calibration body in which the concentration of EB in Tube 2 was maintained at 0.6% concentration-by-mass as a control reference, and the concentration of EB in Tube 1 was varied from 0 to 0.9%.

Figure 12A:
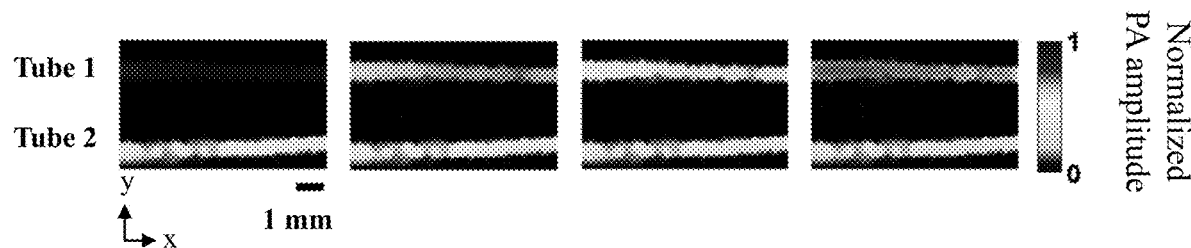
FIG. 12A is a series of snapshot widefield images of pairs of tubes filled with Evans Blue (EB) at various concentrations. The concentration of EB in Tube 1 varied from 0 to 0.9% concentration of EB from left to right and Tube 2 had a constant EB concentration of 0.6%.
Figure 12B:
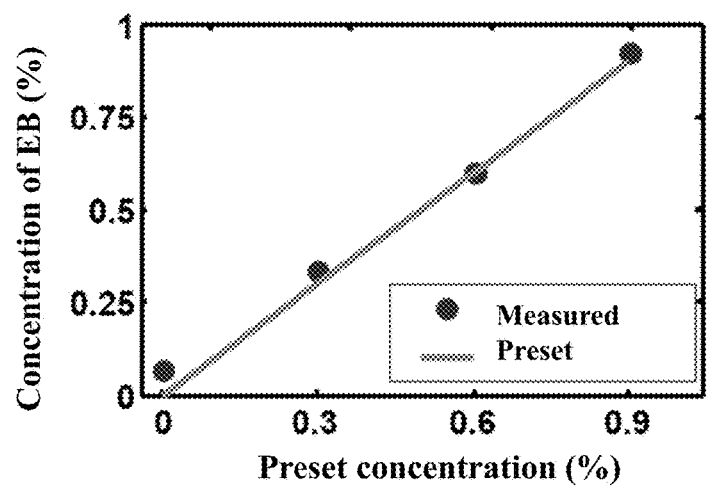
FIG. 12B is a graph summarizing the EB concentrations within tube 1 in the series of images shown in FIG. 12A measured using a PATER imaging system as compared to the preset EB concentration values.
Figure 12C:
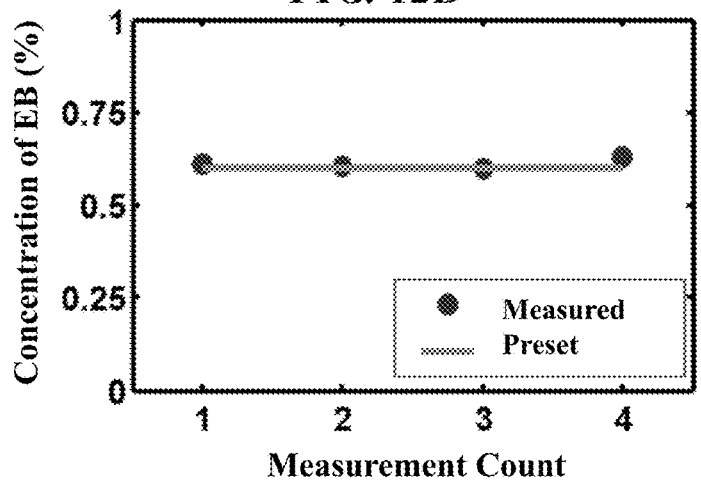
FIG. 12C is a graph summarizing the EB concentrations within tube 2 in the series of images shown in FIG. 12A measured using a PATER imaging system as compared to the preset EB concentration values.

FIG. 12A shows a series of snapshot widefield images obtained at various EB concentrations within Tube 1 of the phantom calibration body. FIG. 12B is a graph summarizing the concentration of EB in Tube 1 determined from the snapshot widefield images as a function of the preset concentration of EB introduced into Tube 1. FIG. 12C is a graph summarizing the concentration of EB in Tube 2 determined from the snapshot widefield images as a function of the preset concentration of EB in Tube 2. FIG. 12B and FIG. 12C both indicate strong agreement between the measured and predetermined EB concentrations. The measured concentrations, calculated based on the widefield image results, fit the preset concentrations well, with a ~0.038% standard error.

The results demonstrated the high sensitivity of the PATER imaging system 100, enabling detection of subtle changes in the imaged object 132.

Example 3: Imaging Depth of PATER Imaging System

To assess the imaging depth of brain vasculature obtained through intact scalp and intact skull using the PATER imaging system 100, the following experiments were conducted.

In comparison to visible light (380-700 nm), near-infrared light (700-1400 nm) had previously demonstrated deeper and finer photoacoustic microscopy (PAM) imaging of vasculature in the mouse brain with the scalp removed (data not shown). To assess the effect of illumination wavelength on the imaging depth and resolution enabled by the PATER imaging system 100, a widefield illumination wavelength of 1064 nm was used to noninvasively image mouse brain vasculature through both intact scalp and intact skull.

Female ND4 Swiss Webster mice (Harlan Laboratory, Inc.; 18-20 g, 6-8 weeks old) were used for these experiments. Each mouse was anesthetized in a small chamber with gaseous isoflurane mixed with air, and then transferred to a customized animal mount where the anesthesia gas was continuously supplied. The animal mount consisted of a stereotaxic frame that fixed the mouse's head, and a heating pad that maintained the mouse's body temperature at ~38° C. The hair on the mouse's head was razor trimmed and the scalp was either kept intact or surgically removed depending on the experiment; the skull was left intact for all mice. Bloodstains on the skull were carefully cleaned with phosphate buffered saline solution, and ultrasound gel was applied on the skull as an acoustic coupling medium. The animal mount was raised to contact the mouse's skull with the imaging surface of the ergodic relay 126 of the PATER imaging system 100. The amount of pressure maintained between the animal mount and the ergodic relay 126 was adequate to prevent the mouse's head from moving, but not sufficient to interrupt the blood supply in the brain.

Figure 6A:
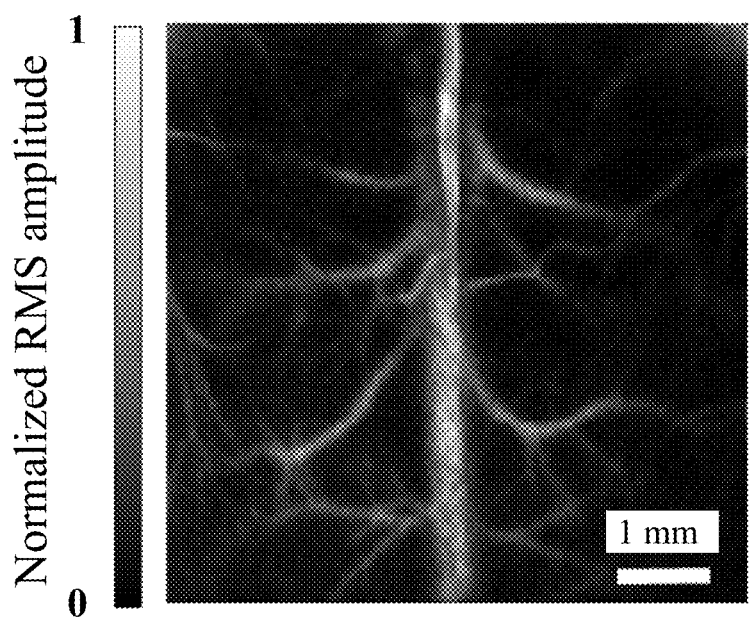
FIG. 6A is an RMS amplitude projection image of the vasculature of a mouse brain obtained through an intact scalp and skull during calibration of the PATER imaging system illustrated in FIG. 1B.

A 6×6 mm$^2$ region of the mouse brain was imaged at the illumination wavelength of 1064 nm to obtain the point-by-point calibration and widefield measurement images. A representative RMS amplitude projection image of the mouse brain vasculature reconstructed using the data obtained through an intact scalp during the point-by-point calibration at the illumination wavelength of 1064 nm is shown in FIG. 6A. A representative snapshot widefield image obtained at the same illumination wavelength is shown in FIG. 6B.

Figure 6B:
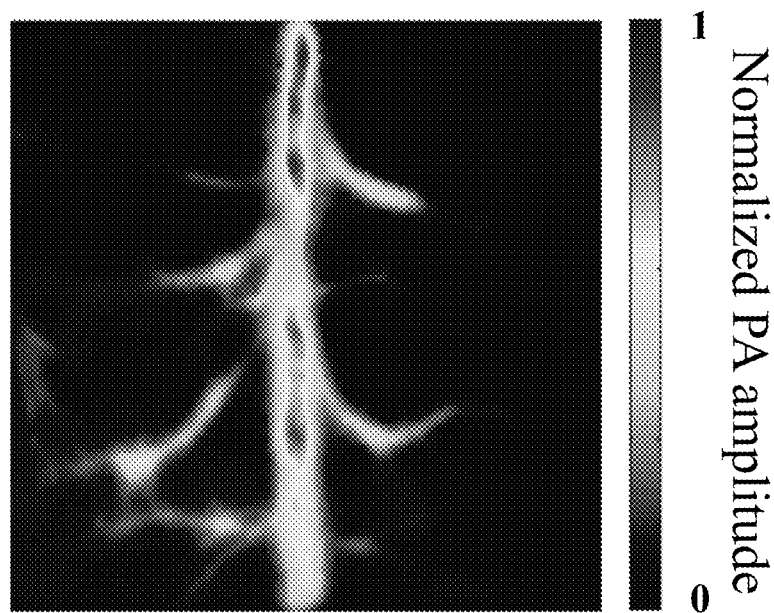
FIG. 6B is a snapshot widefield image of the vasculature of a mouse brain obtained through an intact scalp and skull using the PATER imaging system illustrated in FIG. 1A.
Figure 14A:
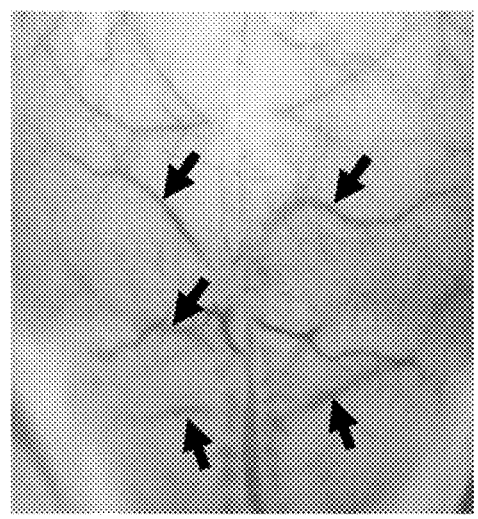
FIG. 14A is a photograph of a mouse brain vasculature with the scalp removed, acquired after the PATER imaging depicted in FIG. 13B and FIG. 13C.
Figure 14B:
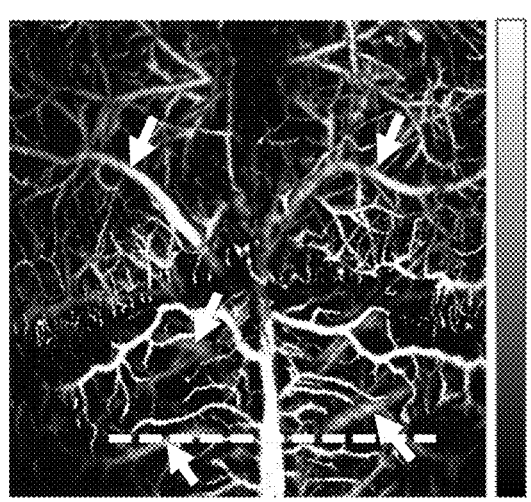
FIG. 14B is a maximum amplitude projection image of the mouse brain vasculature corresponding to the photograph of FIG. 14A acquired without scalp by conventional optical-resolution PAM methods.
Figure 14C:
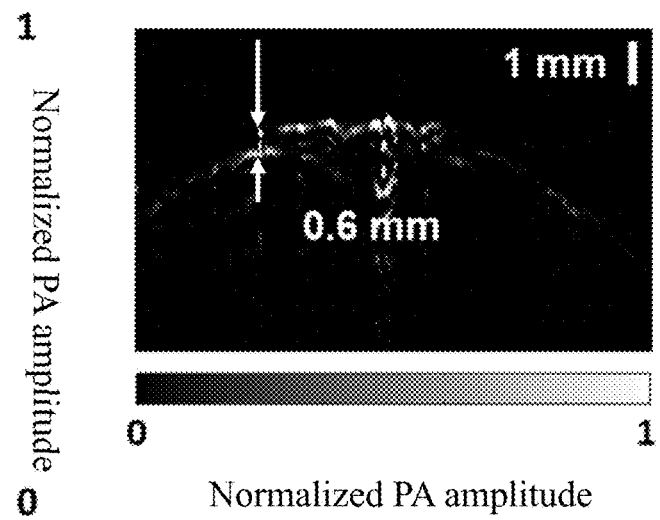
FIG. 14C is a B-scan image obtained along the dashed transect line shown in FIG. 14B.

In order to verify that the vasculature appearing in the images of FIG. 6A and FIG. 6B were not superficial vessels within the scalp, vasculature in the mouse brain with the scalp intact were imaged using the PATER imaging system 100. A photograph of the mouse head with the intact scalp is shown in FIG. 13A. The RMS amplitude projection image of the mouse brain vasculature reconstructed using the data obtained through an intact scalp during the point-by-point calibration is shown in FIG. 13B. To obtain a detailed image of the mouse's brain vasculature, the mouse's scalp was removed and the brain vasculature was then imaged using an optical-resolution (OR) PAM system with laser pulses delivered at 570 nm wavelength. FIG. 14B is the resulting OR-PAM image of the mouse brain vasculature obtained using OR-PAM imaging as described above. FIG. 14CF is a B-scan image of the mouse brain vasculature obtained along the dashed line shown in FIG. 14B using OR-PAM imaging.

The mouse's skull was removed after completion of OR-PAM imaging to visually inspect the brain vasculature. FIG. 14A is a photograph of the mouse's brain with the skull removed. Arrows superimposed on the photograph of FIG. 14A point to representative blood vessels within the mouse brain. Blood vessels corresponding to the blood vessels of FIG. 14A were identified in the images obtained using the PATER imaging system 100 (see FIG. 13C) as well as in the OR-PAM image (see FIG. 14B); the corresponding vessels on these figures are identified by arrows overlaying each respective image.

The OR-PAM B-scan image of FIG. 14C verified the depths of the brain blood vessels imaged using the PATER imaging system 100 shown in FIG. 13C. The PATER imaging system 100 was able to image brain vasculature at a depth of ~1.1 mm, given that the vasculature was ~0.6 mm under the skull, the thickness of the scalp was ~0.3 mm, and the thickness of skull was ~0.2 mm.

The results demonstrated that the PATER imaging system 100 is capable of PA imaging of brain vasculature through an intact mouse scalp and skull, and can achieve lateral resolution of blood vessels within a mouse brain.

Example 4: Imaging Hemodynamic Responses to Paw Stimulation of Brain Vasculature The following experiments were conducted to assess the ability to image rapidly occurring dynamic activity using the PATER imaging system 100 by imaging in vivo the hemodynamic response in a mouse brain to front paw stimulations.

The mice were prepared for imaging in a manner similar to the methods described in Example 3, with modifications as described below.

Light pulses used for illumination were delivered at a wavelength of 532 nm. This wavelength is approximately an isosbestic wavelength for both oxy- and deoxy-hemoglobin, i.e. the molar absorption coefficients are equal for these two forms of hemoglobin. Each mouse brain vasculature was imaged through the intact skull (with the scalp removed) in a point-by-point calibration similar to the point-by-point calibration described above. Snapshot widefield images were then obtained using the PATER imaging system 100 with an 8 mm×6 mm field-of-view and at a frame rate of 10 Hz as described herein above. During widefield image acquisition, the left and right paws of each mouse were alternately stimulated by nipping the paws with pointed forceps. Each paw stimulation lasted approximately 1 second. The resulting snapshot widefield images were processed with a 2D median filter and a Gaussian filter to construct an image of fractional changes in PA signal amplitude due to paw stimulation.

The mean of measurements of the first 5 widefield images/frames was used as a baseline to calculate subsequent differences in widefield measurements. This baseline was subtracted from each frame $x_i$ averaged over a sliding averaging window size of 5 to obtain the difference in widefield measurement $\Delta X_n$, as expressed in Eqn. (10):

$$\Delta X_n = \frac{\sum_{i=n}^{n+4} x_i}{5} - \frac{\sum_{i=1}^{5} x_i}{5}, (n = 1, 2, 3 \ldots),$$

Eqn. (10)

Figure 7A:
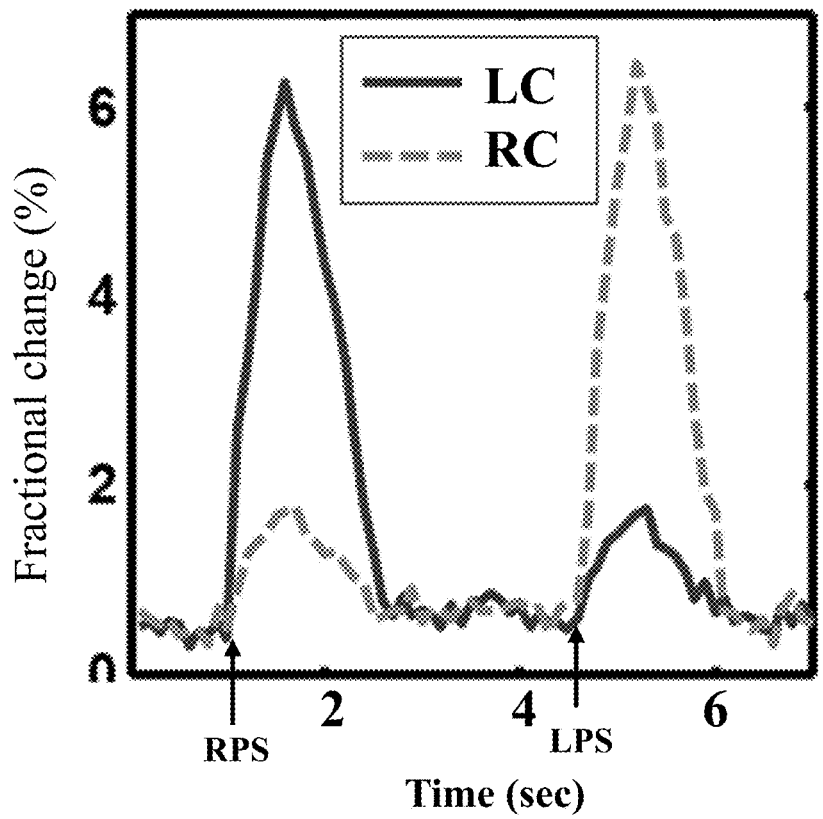
FIG. 7A is a graph showing time courses of differential PA signals for the left cortex (LC) and right cortex (RC) in response to right paw stimulation (RPS) and left paw stimulation (LPS)
Figure 7B:
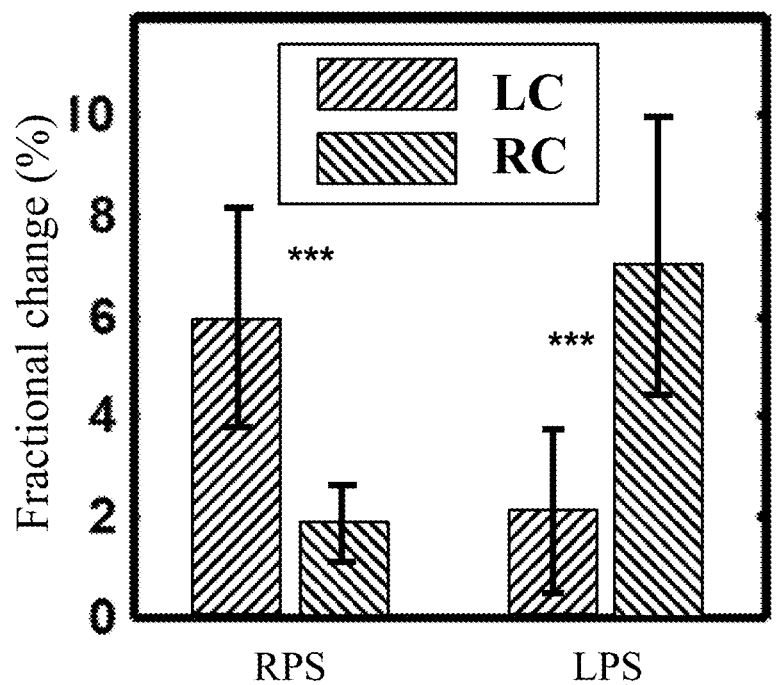
FIG. 7B is a bar graph summarizing the fractional changes in signal amplitude between the left cortex and the right cortex during RPS and LPS stimulations; error bars correspond to standard deviation and *** denotes $p<0.001$, calculated by the two-sample t-test.

A representative RMS amplitude projection image of the mouse brain vasculature reconstructed using the data obtained during the point-by-point calibration of the PATER imaging system 100 is shown in FIG. 5A. A representative snapshot widefield image of the brain vasculature prior to paw stimulation is shown in FIG. 5B. FIG. 5C and FIG. 5D are images showing fractional changes in PA signal amplitude due to paw stimulation overlaid on top of the RMS amplitude projection images for stimulation of the right paw (RPS) and for stimulation of the left paw (LPS), respectively. FIG. 7A is a graph summarizing the fractional changes in PA signals 204 measured in the left cortex (LC) and right cortex (RC) after right paw stimulus (RPS) and left paw stimulus (LPS) as a function of time. FIG. 7B is a bar graph summarizing the fractional changes in peak PA signals 204 measured in the left cortex (LC) and right cortex (RC) after right paw stimulus (RPS) and left paw stimulus (LPS).

An increase in PA amplitude was observed in the contralateral somatosensory brain region during stimulations, as well as a weaker increase in PA amplitude in the ipsilateral somatosensory brain region. These increases in PA signal magnitudes in contralateral and ipsilateral somatosensory brain regions during stimulations were consistent with previous findings that suggested a vascular interconnection between the left and right hemispheres of the brain. An increase in PA amplitude was also observed between the two hemispheres (see FIG. 5C and FIG. 5D), likely originating from the sagittal sinus region underneath the skull.

The results of these experiments confirmed that the PATER imaging system 100 possessed sufficient spatial and temporal resolution to image dynamic changes in brain vasculature in response to paw stimulation through intact scalp and intact skull.

Example 5: PATER Imaging of Blood Oxygen Saturation (sO2)

The following experiments were conducted to image the in vivo blood oxygen saturation in a mouse brain responding to oxygen challenge using a single wavelength of light.

The initial equipment and experimental animal set-up of Example 3 was used in this experiment. The absorption of light in blood mainly occurs within oxy- and deoxy-hemoglobin of circulating red blood cells. Thus, the absorption coefficient, $\mu_a$, of blood can be calculated as expressed in Eqn. (11):

$$\mu_a = \ln(10)(\varepsilon_{HbO_2} C_{HbO_2} + \varepsilon_{Hb} C_{Hb})$$  Eqn. (11)

where $\varepsilon$ is the molar extinction coefficient [$M^{-1}cm^{-1}$], C is the concentration [M], and the $HbO_2$ and Hb subscripts denote oxy- and deoxy-hemoglobin respectively.

The oxygen saturation in blood ($sO_2$) can be calculated as expressed in Eqn. (12):

$$sO_2 = \frac{C_{HbO_2}}{C_{HbO_2} + C_{Hb}} = 1 - \frac{C_{Hb}}{T_{Hb}}$$  Eqn. (12)

where $T_{Hb}$ is the total hemoglobin concentration in blood (combined oxygenated and deoxygenated hemoglobin), as expressed in Eqn. (13):

$$T_{Hb} = C_{HbO_2} + C_{Hb}$$  Eqn. (13)

Therefore, the change in the blood oxygen saturation can be calculated as expressed in Eqn. (14):

$$\Delta sO_2 = -\frac{\Delta C_{Hb}}{T_{Hb}}$$  Eqn. (14)

Assuming that the change in $T_{Hb}$ is insignificant, then a change in blood oxygen saturation signifies that $\Delta C_{Hb} = -\Delta C_{HbO_2}$. At a laser pulse wave length at which light absorption is dominated by deoxy-hemoglobin absorption, such as 620 nm, the absorption ratio of deoxygenated Hb absorption ($\varepsilon_{Hb}$) to oxygenated Hb absorption ($\varepsilon_{HbO_2}$) is approximately 7, and thus the change in absorption is mainly due to the change in concentration of deoxy-hemoglobin. Therefore, it may be assumed that $\Delta\mu_a \approx \ln(10)\varepsilon_{Hb}\Delta C_{Hb}$, and the change in PA signal at 620 nm is proportional to the change in blood oxygen saturation.

Using a single 620 nm wavelength of light, the in vivo blood oxygen saturation ($sO_2$) in a mouse brain responding to oxygen challenge was imaged using a PATER imaging system 100 over a field of view of 3 mm×3 mm and at a frame rate of 50 Hz. A tunable dye laser (CBR-D, Sirah GmbH) with Rhodamine B dissolved in ethanol as gain medium was used to generate the laser beam at 620 nm wavelength for the widefield illumination 206 used for imaging.

The oxygen challenge was performed by manipulating the oxygen concentration of the mouse's inhaled gas. In this study, a mixture of 95% oxygen and 5% nitrogen was initially administered to the mouse along with an amount of gaseous isoflurane for anesthesia. The mouse brain vasculature was imaged through an intact scalp in the calibration step as described herein above. During the oxygen challenge, the mixture was changed to 5% oxygen and 95% nitrogen for 3 minutes, and then changed back to the initial concentration to end the challenge. Snapshot widefield image data were recorded during the oxygen challenge, and the widefield difference was calculated pixel by pixel. The resulting widefield image was processed with a 2D median filter and a Gaussian filter, and then overlaid on the RMS amplitude projection image as described in Example 4. Two oxygen challenge cycles were performed and analyzed.

Figure 9A:
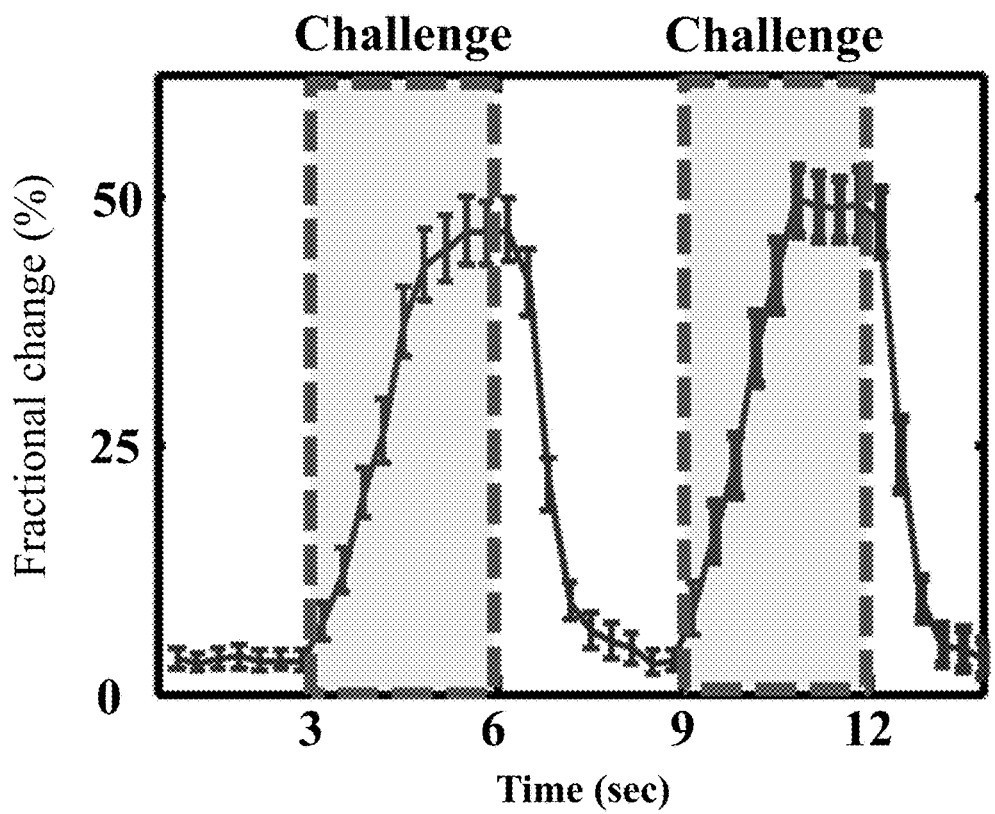
FIG. 9A is a graph plotting the time course of the fractional change in PA signal amplitude in response to two cycles of oxygen challenge, measured using the PATER imaging system illustrated in FIG. 1A at a laser pulse wavelength of 620 nm; error bars correspond to standard error.

FIG. 8A is an RMS amplitude projection image of the mouse brain vasculature reconstructed using the data obtained during the point-by-point calibration, and FIG. 8B is a snapshot widefield image of the brain vasculature prior to any oxygen challenges. FIG. 8C is a map of the blood oxygen saturation at normoxic conditions calculated as described above using Eqn. (6). FIG. 8D is a map of the blood oxygen saturation at hypoxic conditions calculated in a similar manner. FIG. 9A is a graph summarizing the fractional change in PA signal amplitude over two cycles of oxygen challenge; the fractional changes were calculated using the methods described in Example 4 above.

Figure 9B:
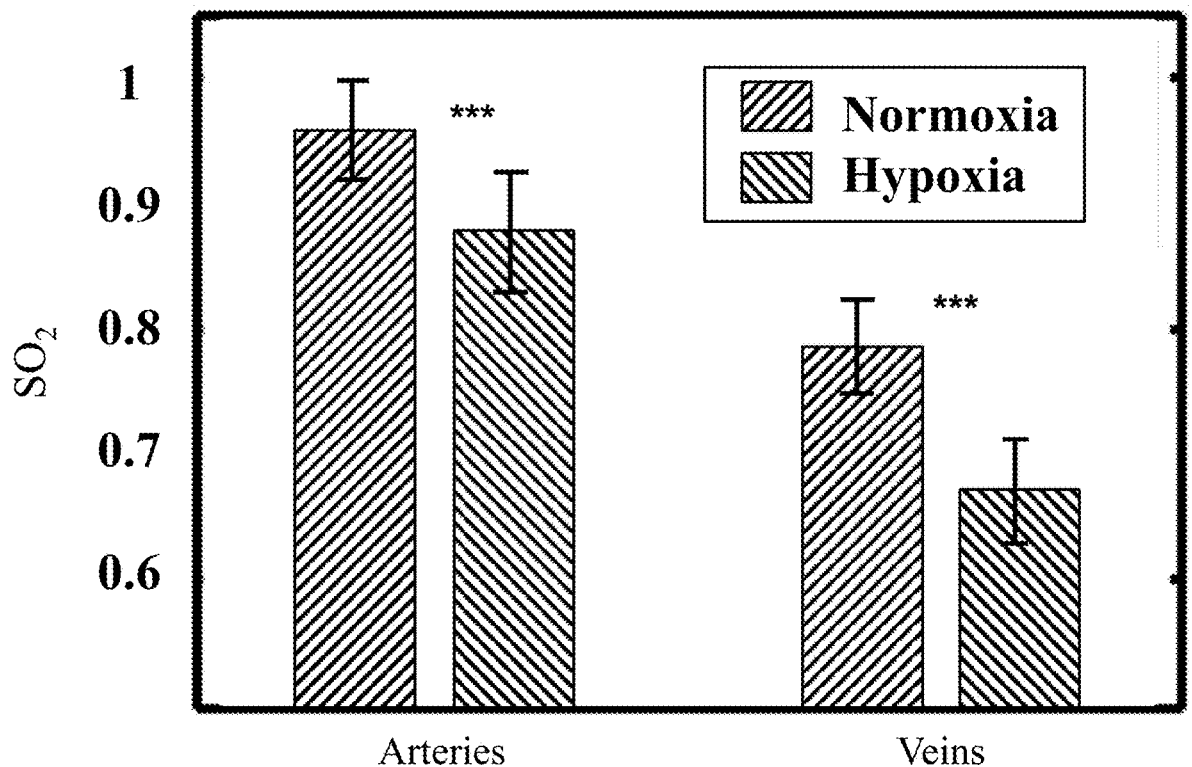
FIG. 9B is a bar graph summarizing the blood oxygenation ($sO_2$) within arteries and veins of the vasculature of a mouse brain illustrated in FIGS. 8A and 8B measured; error bars correspond to standard deviation and *** denotes $p<0.001$, calculated by the two-sample t-test.

Widefield measurements with a laser beam delivered at 532 nm wavelength were taken before and 3 minutes into the oxygen challenge to provide dual wavelength measurements for a $sO_2$ calculation, and a vessel segmentation algorithm was used to individually identify and label the arterial and venous vessels for sO2 calculations. FIG. 9B is a bar graph summarizing the blood oxygen saturation of arteries and veins of the mouse brain vasculature during normoxic and hypoxic conditions.

The PATER imaging system 100 was able to image the oxygen saturation in a mouse brain caused by the exposure to different mixtures of oxygen and nitrogen. The absolute rate of signal change was greater when the mouse was challenged than during recovery from hypoxia, which is consistent with the results reported previously. The $sO_2$ in both arteries and veins of the mouse brain dropped significantly during the oxygen challenge (see FIG. 8C, FIG. 8D, and FIG. 9B).

The results of this experiment demonstrated the ability to monitor changes in blood oxygenation levels in brain vasculature resulting from stimulations or treatments such as an oxygen challenge.

Example 6: High Speed Identification of Blood Vasculature

The following experiments were conducted to assess the ability to differentiate blood vessel patterns between individual mice with two single laser shots using the PATER imaging system 100.

Two mice were used in this experiment, hereinafter referred to as Mouse 1 and Mouse 2. The mice were prepared for PATER imaging as described previously in Example 3. Mouse 1 was fixed in a stereotaxic frame and a region of the cortical vasculature was recorded in a point-by-point calibration of the PATER imaging system 100 as described above. Widefield signals of the same vasculature region of Mouse 1 were subsequently recorded as described herein above over a FOV of 3 mm×3 mm and at a frame rate of 1 Hz. During the widefield recording of Mouse 1, the mouse was detached from the ergodic relay 126 and then reattached at the same position using a linear translational stage 114 (PT1, Thorlabs, Inc.). Random noise was recorded during widefield recording while the mouse was detached from the ergodic relay 126, and PA signals 204 were observed again after the mouse was reattached to the ergodic relay 126. Point-by-point calibration and widefield recording were similarly conducted for Mouse 2. Reconstruction of widefield images of the brain vasculature of Mouse 1 was performed using the recorded calibration data sets for Mouse 1 as well as for Mouse 2.

Figure 11:
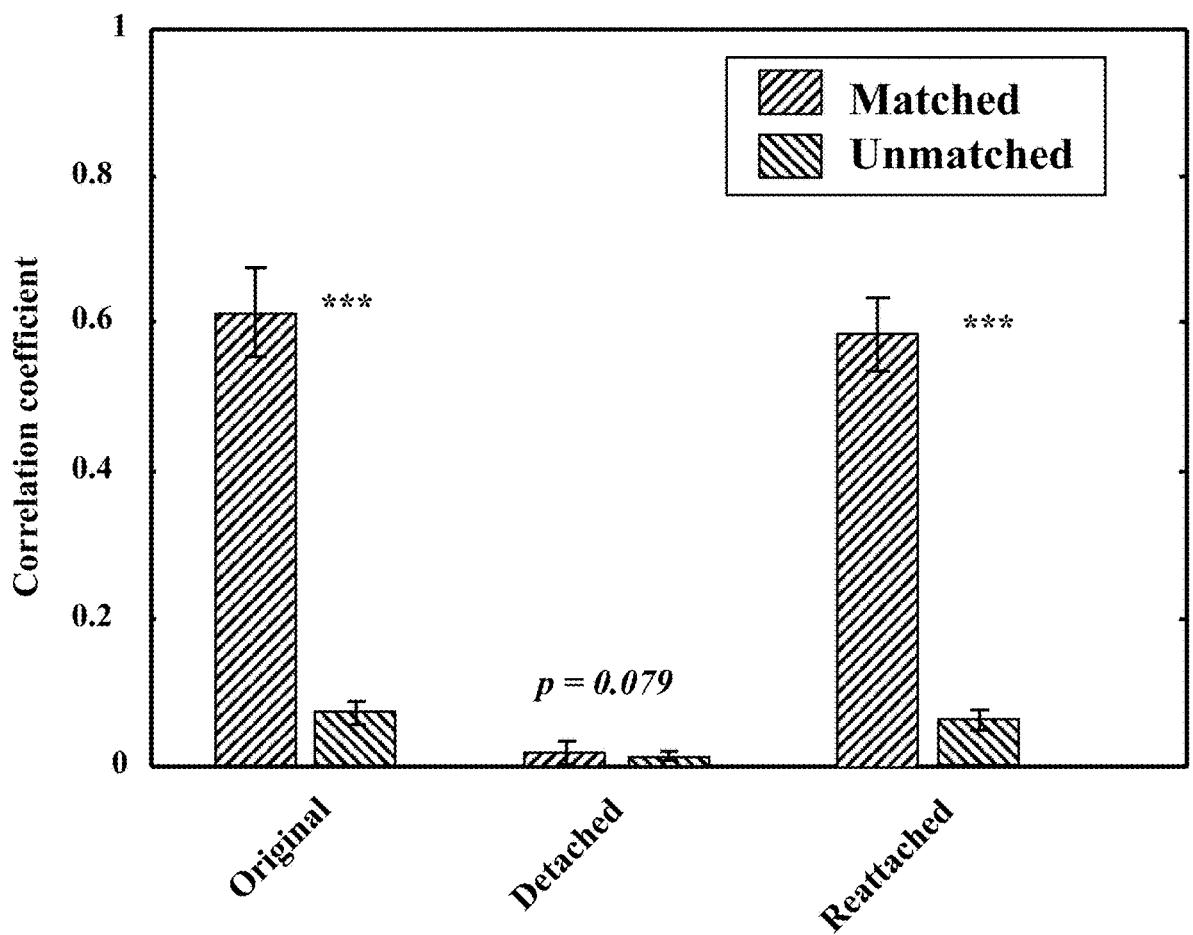
FIG. 11 is a graph comparing the correlation between snapshot widefield image reconstructions and RMS amplitude projections generated for the brain vasculatures of Mouse 1 and Mouse 2, for three conditions: mouse as originally attached to the ergodic relay of the PATER imaging system illustrated in FIG. 1A (original); mouse detached from the ergodic relay (detached), and mouse reattached to the ergodic relay (reattached) to demonstrate the consistency of reconstruction. Error bars correspond to standard deviation and *** denotes $p<0.001$, calculated by the two-sample t-test.

FIG. 10A is an RMS amplitude projection image of the brain vasculature of Mouse 1 acquired from data obtained during the point-by-point calibration of the PATER imaging system 100. FIG. 10B is an RMS amplitude projection image of the brain vasculature of Mouse 2 acquired from data obtained during the point-by-point calibration of the PATER imaging system 100. FIG. 10C is a widefield image of the brain vasculature of Mouse 1 reconstructed using the calibration data obtained from Mouse 1 (matched). FIG. 10D is a widefield image of the brain vasculature of Mouse 1 reconstructed using the calibration data obtained from Mouse 2 (unmatched). FIG. 11 is a bar graph summarizing the correlation between the widefield reconstructions obtained using the calibration data from the corresponding mouse (matched) as well as the correlations and between the widefield reconstructions obtained using the calibration data from mouse different from the mouse subjected to widefield imaging (unmatched). FIG. 11 summarizes these correlations using data obtained after the initial attachment of the ergodic relay 126 to each mouse (original), after the ergodic relay 126 is detached from each mouse (detached), and after the ergodic relay 126 is reattached to each mouse (reattached).

The widefield image 218 reconstructed from matched calibration data revealed the original vasculature, and the widefield image 218 reconstructed from unmatched calibration data failed to reconstruct an image 218 in which the original vasculature could be discerned. Consequently, the brain vasculature patterns of individual mice could be differentiated between the two mice. The correlation coefficients between the widefield reconstruction images 218 and the calibration images indicated that the widefield images 218 reconstructed from matched calibration data have much higher correlation than those reconstructed from unmatched calibration data. This differentiation of brain vasculature patterns was not impacted by detaching and reattaching the mice to the ergodic relay 126, indicating that the recognition of individual brain vascularization patterns by the PATER imaging system 100 are relatively insensitive to slight variations in the degree of contact of the mouse to the input surface of the ergodic relay 126.

The results of this experiment demonstrated the ability of the PATER imaging system 100 to discriminate between vascularization patterns of individual mice.

Example 7 Tracing Melanoma CTCs in Mouse Brain

To demonstrate the ability to perform super-resolution imaging and flow direction mapping, as well as detection of CTCs in vivo the following experiments were conducted. Most melanoma tumor cells contain high concentrations of melanin, which have much stronger optical absorption than hemoglobin at around 660 nm, thus providing a large optical contrast between the moving CTCs and the background blood. In this study, the ability of the PATER system described above to monitor the migrations of numerous melanoma CTCs simultaneously in a mouse brain vasculature without exogenous labelling was demonstrated. Super-resolution imaging and flow direction mapping of the mouse brain vasculature was accomplished by localizing and recording the positions of the melanoma CTCs.

The PATER system used in these experiments included a 5-ns pulsed laser beam at 532 nm (INNOSAB IS8II-E, Edgewave GmbH; 2-KHz pulse repetition rate). The laser beams were partially reflected by a beam sampler to a photodiode (DET36A, Thorlabs, Inc.) to correct PA signals for fluctuations in light energy. The laser beam that passed through the beam splitter was reflected by a mirror (PF10-03-P01, Thorlabs, Inc.) and passed through an optical-element wheel that enabled switching the active optical element in the light path according to the acquisition mode as described in detail above. The system further included two-channel digitizer (ATS9350, AlazarTech, Inc.; 100-MS/s sampling rate, 16,384 data points/acquisition sampling length) to record the PA signals and the photodiode measurements. The dye laser pumped by the 532-nm pulsed laser was tuned to generate a 660-nm laser beam by using DCM dissolved in ethanol as the gain medium for monitoring melanoma CTC migrations in the mouse brain.

The mouse was prepared for imaging in a manner similar to the methods described in Example 3, with modifications as described below. A carotid artery cannulation procedure was performed on the mouse to access the left common carotid artery. An arterial catheter (MAC-02, SAI Infusion Technologies Inc.; 1-F tip outer diameter) was inserted into the left common carotid artery to facilitate the melanoma cancer cell injection. The skin of the mouse was sutured after the procedure while the arterial catheter was exposed as the CTC injection port.

A cortical region of the mouse's brain was scanned for calibration after performing the carotid artery cannulation procedure. Approximately 200 μL of cell suspension containing $3 \times 10^6$ B16 cells was slowly injected through the arterial catheter into the left common carotid artery. Then, snapshot images of the cortical region were acquired using 660-nm light to monitor the migration of CTCs for approximately two minutes. Differences in snapshot measurements were calculated by temporal running averaging over five consecutive frames using Eqn. (10) provided above. The snapshot differential images were processed in MATLAB with a 2D median filter (medfilt2) using median values from the 5-by-5 neighborhood pixels and a 2D Gaussian filter (imgaussfit) with a sigma value of 10.

CTC localization accuracy was estimated based on a least-squares fitting to a Gaussian function. A significant source of noise within the snapshot images obtained using the PATER system included random, additive, and statistically stable (across all pixels in the FOV) detector or environmental noise. This detector or environmental noise contrasted with the photon shot noise associated with other super-resolution imaging methods, which follows a Poisson distribution whose parameter is related with the true photon count at each pixel. Therefore, the localization accuracy, as quantified by the RMS error of the fitted center position $\hat{x}_0$, in the detector or environmental noise-limited case was expressed as:

$$\sqrt{\langle (\Delta \hat{x}_0)^2 \rangle} = 2^{3/4} \frac{\sigma}{SNR_L}. \quad \text{Eqn. (15)}$$

where $\sigma$ is the standard deviation of the original Gaussian point-spread function (PSF), and $SNR_L$ is the signal-to-noise ratio with a conceptual pixel of width $L=\sqrt{2\pi}\sigma$. The localization accuracy as expressed in Eqn. (15) was proportional to the original resolution of the PATER system and inversely proportional to the value of $SNR_L$.

In order to track and localize the flowing CTCs over the FOV, the mouse's brain was imaged at 1,000 frames per second (fps) for 100 seconds. In the entire 3D (x-y-t) volume, candidate CTCs were found using a sequential procedure that included 1) applying the temporal running average to the consecutive image frames to suppress background noise; 2) filtering the volume with a Difference-of-Gaussian filter, whose scales were empirically determined as 1.4 and 1.8 pixels, 3) detecting all local maxima that were greater than 20% of the largest maximum value, and 4) fitting a 2D Gaussian function to the neighborhood of each local maximum to localize the center of the CTCs at the sub-pixel level. After localization, the CTC particles were further filtered with additional trackability criterion.

All candidate particles were tracked over the course of the video, and only those particles that could be tracked across at least 3 frames within a 5-frame window (10-ms) at the maximum flow speed of 10 mm/s were retained. Tracked CTC particles were then connected into paths and plotted to form a localization image. The finest resolution for the in vivo CTC localization study was estimated to be 300 nm (10-µm reconstruction pixel width, ~100-µm standard deviation of the Gaussian PSF, and an SNR of ~110, data not presented).

Major vessels were manually identified on the optical-resolution image to analyze the flow speed pattern. PA signals were extracted along vessel centerlines from the video to form a length-time 2D image for each vessel. A moving-window Fourier Transform-based flow speed extraction algorithm was used to calculate the flow speed and direction along the vessels.

Figure 19A:
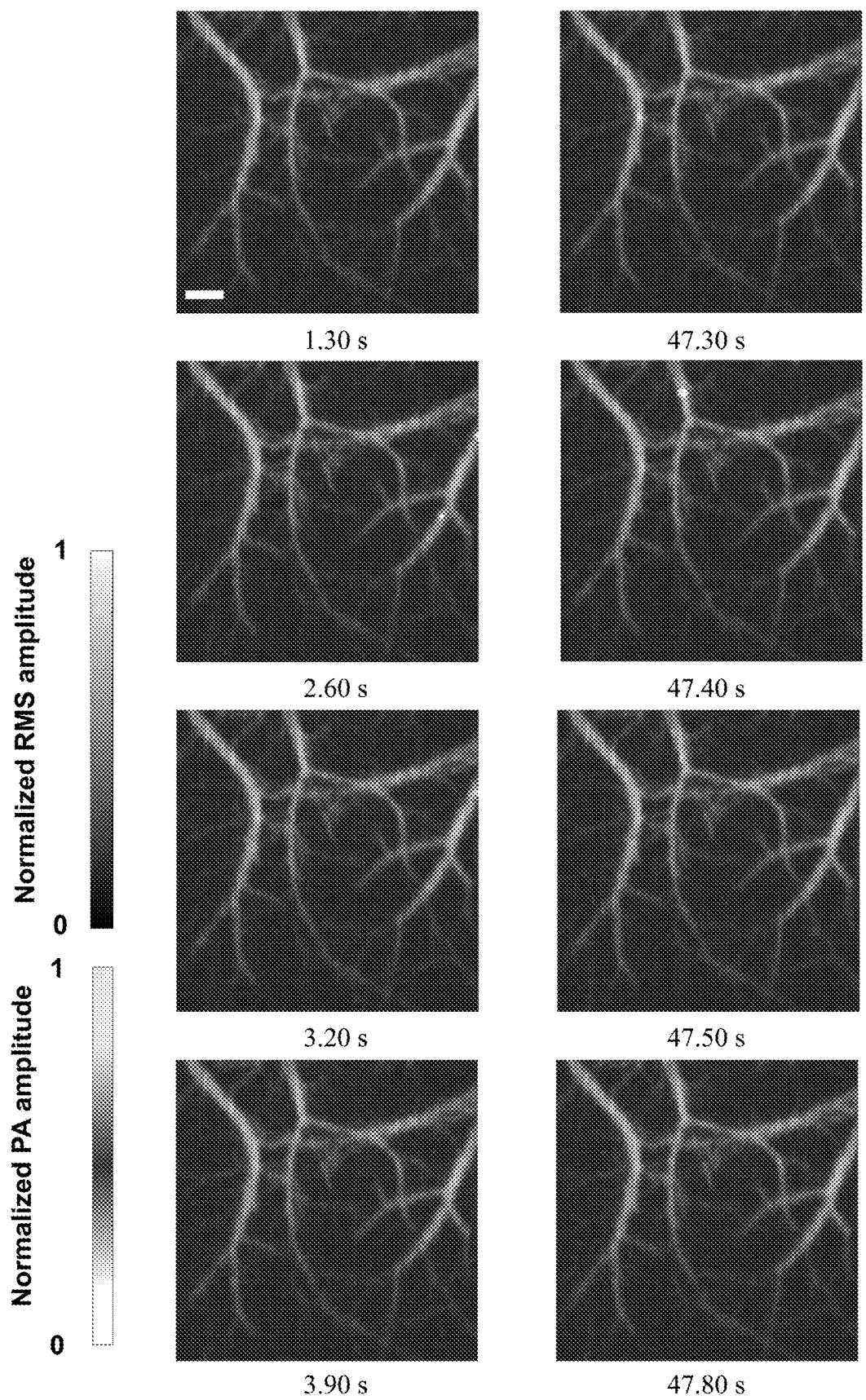
FIG. 19A contains a series of reconstructed snapshot images (with a threshold of 20% from the peak value of the largest local maxima) at various times, overlaid on RMS amplitude projections of the cortical region of a mouse injected with melanoma CTCs.
Figure 19B:
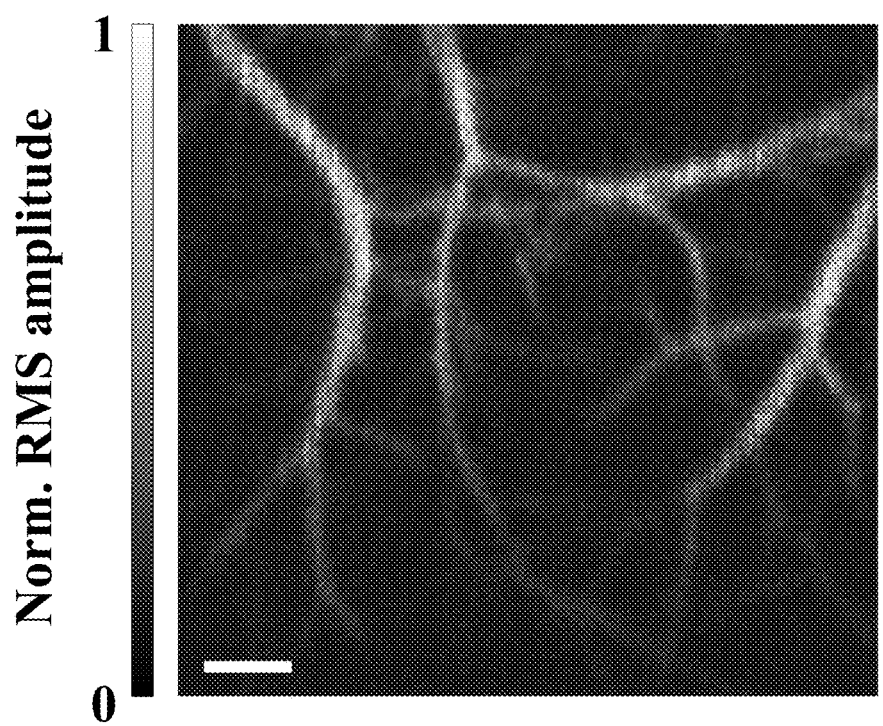
FIG. 19B contains an image of an RMS amplitude projection of the cortical region of a mouse obtained during calibration and prior to the injection of melanoma CTCs.

Snapshot measurements on a cortical region of the mouse brain were taken after the injection of melanoma CTCs through the mouse's carotid artery. The reconstructed snapshot images (with a threshold of 20% from the peak value of the largest local maxima) were overlaid on the RMS amplitude projection of the cortical region to highlight the current positions of melanoma CTCs, as illustrated in FIG. 19A. The RMS amplitude projection of the cortical region was obtained during calibration, prior to the injection of CTCs, as illustrated in FIG. 19B. Due to the scattering of the skull, the resolution of the RMS amplitude projection image was about 25 µm.

Figure 19C:
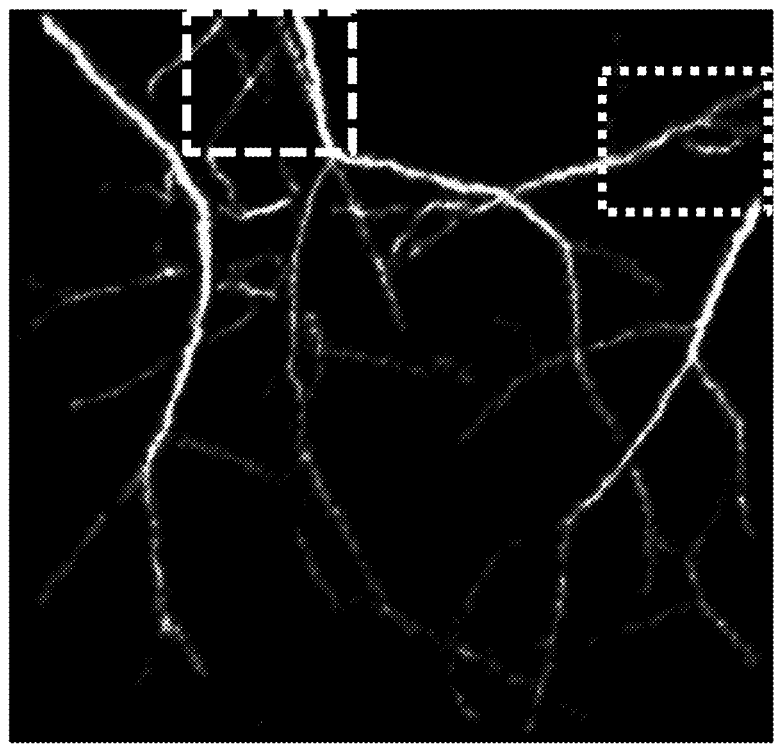
FIG. 19C contains an image of a high-resolution localization map of the high-resolution cortical vasculature of a mouse injected with melanoma CTCs, reconstructed using localized positions of melanoma CTCs from 100,000 snapshot frames.
Figure 19D:
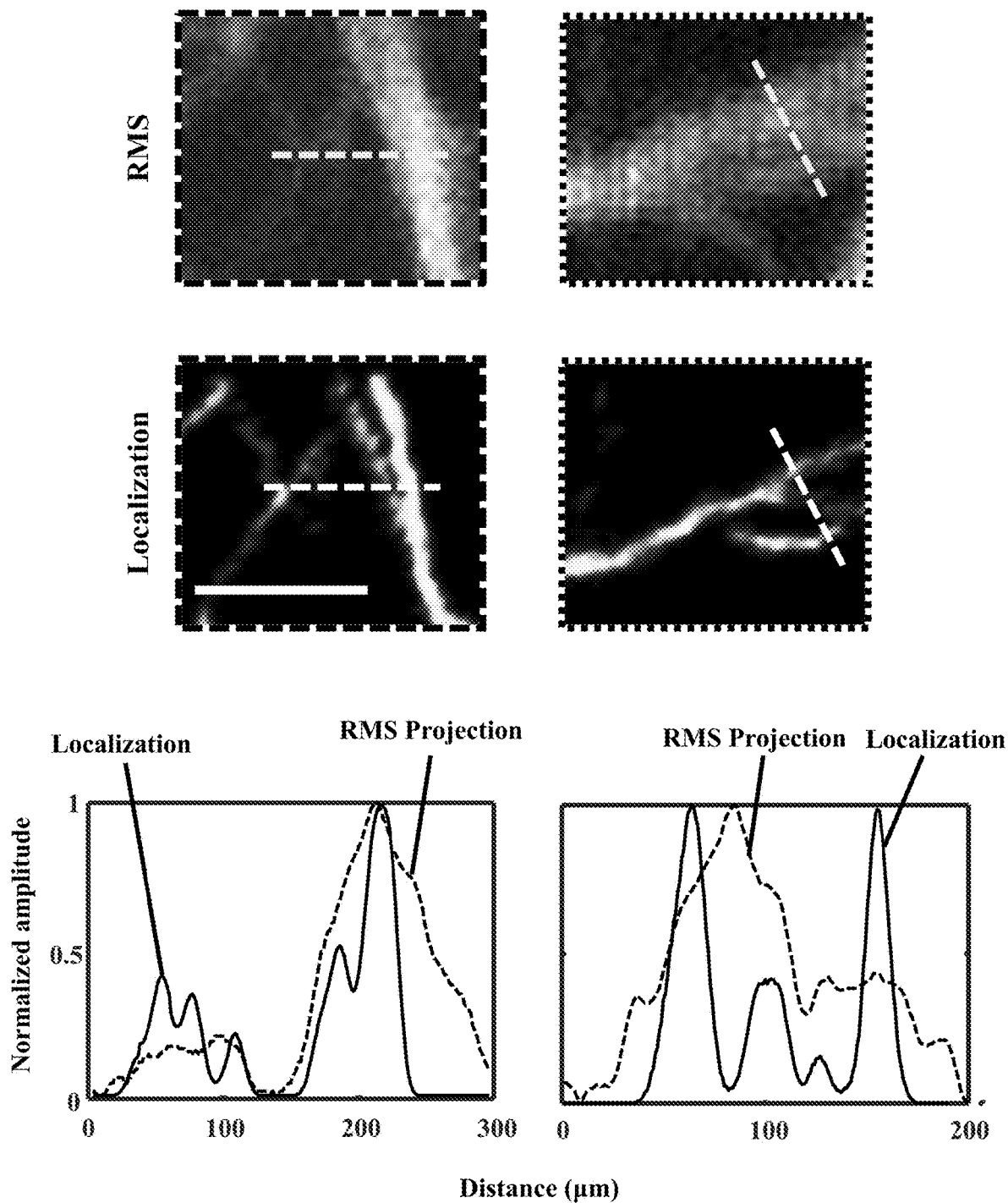
FIG. 19D contained RMS amplitude images and localization maps at blood vessel bifurcations.

The localized positions of the melanoma CTCs from 100,000 snapshot frames were computed to reconstruct the high-resolution localization map of the cortical vasculature, as illustrated in FIG. 19C. The localization map provided finer resolution for the vessels at the bifurcations shown in the boxed regions than the RMS projection maps, demonstrating super-resolution imaging, as illustrated in FIG. 19D. The cross-sectional profiles of the vessels indicated that two neighboring vessels branching out from each other may be separated by a distance of 12 µm, and the FWHM for one of the smallest vessels shown was 7 µm (data not shown), which fell within the range of capillary diameters (5-10 µm). The theoretical finest resolution, quantified from two traces of CTCs migrating through a crossing vasculature in the experimental results, was 300 nm.

The structural density of the localization-enhanced vessels depends on the number of traceable melanoma CTCs that were recognized from the images. Therefore, vessels traced with more melanoma CTC events resembled the vasculature more closely than did vessels traced with fewer events. The resolution of the localization image may be further improved with longer integration times.

Figure 19E:
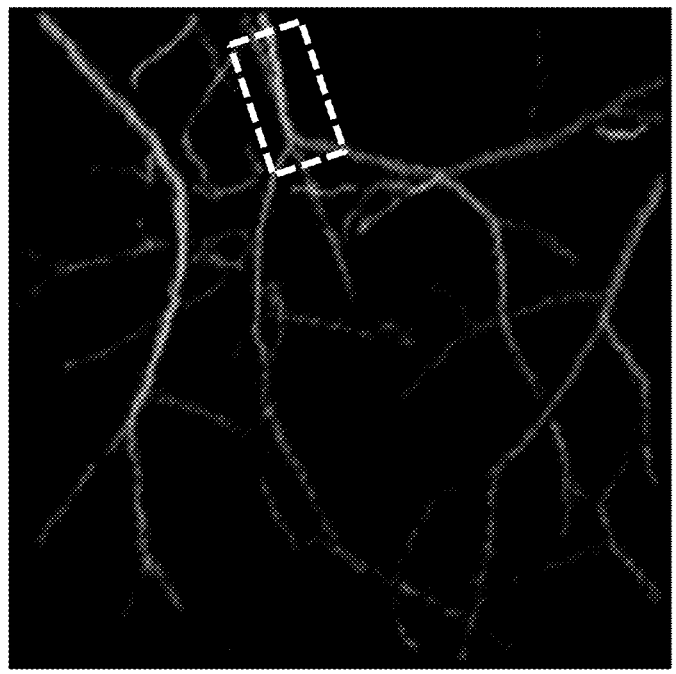
FIG. 19E contains an image showing the tumor cell flow directions in the vessels of a mouse injected with melanoma CTC.
Figure 19F:
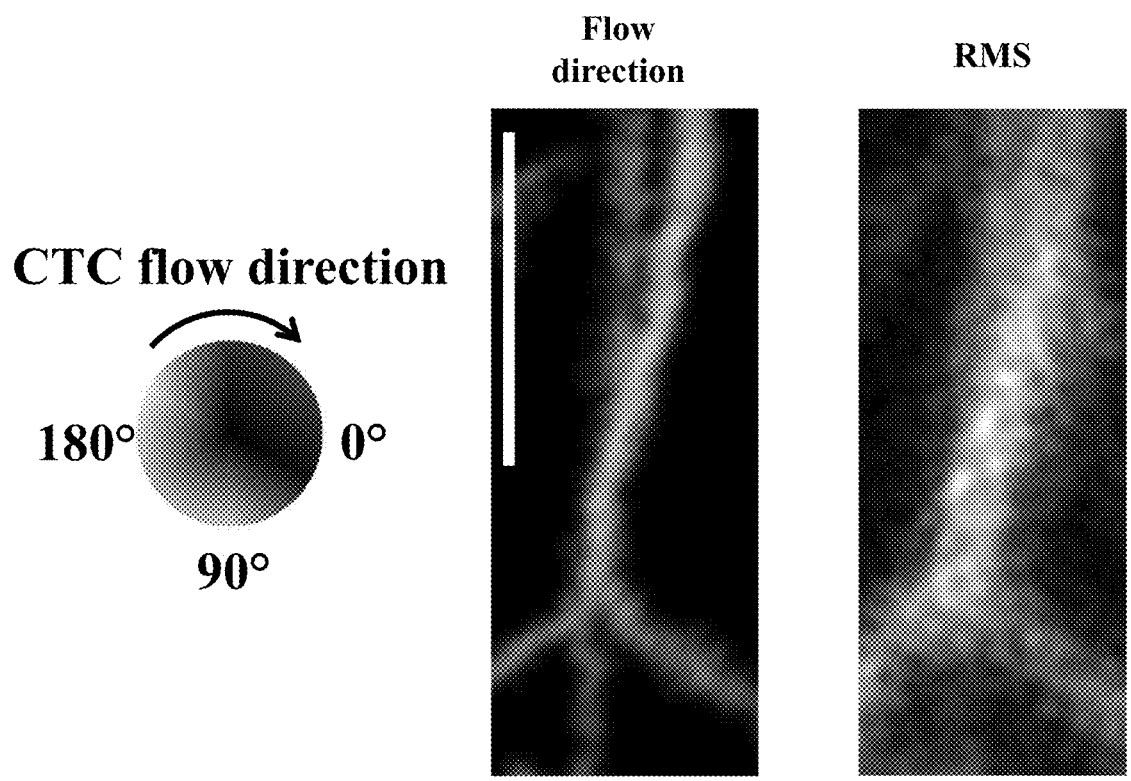
FIG. 19F contains an close-up image of FIG. 19E within the dashed box region, showing the tumor cell flow directions in the vessels of a mouse injected with melanoma CTC obtained using high resolution localization maps (left) and compared to a corresponding RMS-contrast image.

The flow rate and flow direction of the tumor cells in each vessel was estimated by tracing the melanoma CTCs in real time and analyzing the movements of flowing melanoma CTCs. The computed flow rate of melanoma CTCs had a maximum of 0.54 mm/s, which was lower than the cerebral blood speed. A velocity-contrast map was computed for the mouse cortical vasculature by analyzing the flow rate of melanoma CTCs in each vessel in the spatiotemporal frequency domain. Vessels in the mouse brain were individually identified based on the difference in flow speed and flow direction of CTCs. The tumor cell flow directions in the vessels are shown in FIG. 19E. The opposite flow directions and difference in flow rates of some neighboring vessels helped to differentiate them while they could not be resolved in the calibration RMS projection, as illustrated in FIG. 19F.

The results of this experiment demonstrated that if the imaged CTCs are sufficiently separated in a snapshot image (i.e., at most a single CTC or CTC cluster is within a resolution voxel at a time), individual CTC or CTC clusters may be localized using the PATER imaging system with super-resolution. The localization accuracy (quantified by the RMS error of the fitted center position of a single CTC) was inversely proportional to the signal-to-noise ratio (SNR), resulting in super-resolution imaging since SNR is sufficiently high enough.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A photoacoustic imaging system, comprising:
    an ergodic relay coupled optically to a light source configured to produce a light pulse and further coupled acoustically to at least one transducer device, wherein the ergodic relay is further configured to couple acoustically and optically to an object to be imaged.

2. The photoacoustic imaging system of claim 1, wherein the ergodic relay is configured to direct the light pulse into at least a portion of a field of view of the object to be imaged.

3. The photoacoustic imaging system of claim 2, wherein the ergodic relay is configured to direct at least two photoacoustic signals to the at least one transducer device, each of the at least two photoacoustic signals produced at different positions within the field of view of the object to be imaged in response to illumination by the light pulse, wherein the at least one transducer device is configured to detect each of the at least two photoacoustic signals after a delay, each delay comprising a duration between production of the light pulse and arrival of each of the two photoacoustic signals, each delay corresponding to the position at which each photoacoustic signal was produced.

4. The photoacoustic imaging system of claim 1, wherein the ergodic relay comprises an ergodic relay prism comprising a right-angle prism with a light input face, a light output face, and an angled face, the light input face coupled optically to the light source, the light output face coupled acoustically and optically to the object to be imaged.

5. The photoacoustic imaging system of claim 4, wherein the at least one transducer device is selected from at least one single-element transducer, at least one linear transducer array, at least one 2-D transducer array, and any combination thereof.

6. The photoacoustic imaging system of claim 4, wherein the at least one transducer device comprises at least one single-element transducer coupled acoustically to the ergodic relay prism at an edge formed between the light input face and the angled face of the ergodic relay prism.

7. The photoacoustic imaging system of claim 6, wherein the at least one single-element transducer comprises a needle transducer.

8. The photoacoustic imaging system of claim 4, wherein the object to be imaged is coupled acoustically to the ergodic relay prism using an aqueous ultrasound coupling gel positioned between the object to be imaged and the light output face of the ergodic relay prism.

9. The photoacoustic imaging system of claim 1, wherein the ergodic relay comprises an ergodic relay prism and wherein the at least one transducer device is coupled acoustically to the ergodic relay prism using a polyester resin positioned between the at least one transducer device and a portion of the ergodic relay prism.

10. The photoacoustic imaging system of claim 1, further comprising a focusing element positioned between the light source and the ergodic relay, the focusing element configured to modify a beam diameter of the light pulse produced by the light source.

11. The photoacoustic imaging system of claim 10, wherein the focusing element is selected from at least one of a plane convex lens and a diffuser.

12. The photoacoustic imaging system of claim 10, wherein the focusing element is mounted on a focusing element module configured to selectably position the focusing element to modify the beam diameter of the light pulse from the light source.

13. The photoacoustic imaging system of claim 1, further comprising a 2-axis stage configured to move the ergodic relay in a scanning pattern.

14. A method of imaging a field of view within an object using a photoacoustic imaging system, the method comprising:

providing a photoacoustic imaging system comprising an ergodic relay coupled optically to a light source at a light input face and further coupled acoustically to at least one transducer device;

acoustically and optically coupling the object to be imaged to a light output face of the ergodic relay;

directing a diffuse light pulse produced by the light source into the object to be imaged via the light output face, the diffuse light pulse illuminating a field of view within the object;

receiving, via the light output face a plurality of photoacoustic signals from a plurality of positions within the field of view in response to illumination by the diffuse light pulse;

directing each of the plurality of photoacoustic signals to the at least one transducer device via the ergodic relay, wherein each of the plurality of photoacoustic signals is detected at the at least one transducer device after one of a plurality of corresponding delays after producing the diffuse light pulse, each delay corresponding to one of the plurality of positions at which one of the plurality of photoacoustic signals is produced;

forming a photoacoustic imaging data set comprising the plurality of photoacoustic signals and a corresponding plurality of positions within the field of view, each position corresponding to one of the photoacoustic signals; and reconstructing an image from the photoacoustic imaging data set.

15. The method of claim 14, wherein the object to be imaged is acoustically and optically coupled to the light output face of the ergodic relay by positioning an ultrasound coupling gel between the object to be imaged and the light output face of the ergodic relay.

16. The method of claim 14, wherein a light pulse produced by the light source is directed through a diffuser to expand and homogenize the light pulse to produce the diffuse light pulse directed into the field of view.

17. The method of claim 14, further comprising calibrating the photoacoustic imaging system to determine a correspondence between the plurality of corresponding delays and the plurality of positions within the field of view by:

sequentially directing a plurality of focused light pulses produced by the light source into the object to be imaged via the light output face, each focused light pulse illuminating one of a plurality of calibration points within the field of view of the object, the plurality of calibration points forming a scanning pattern over the field of view of the object:

receiving, via the light output face, a plurality of photoacoustic calibration signals, each photoacoustic calibration signal of the plurality of photoacoustic calibration signals produced at one calibration point of the plurality of calibration points in response to illumination by one focused light pulse of the plurality of focused light pulses, the one focused light pulse directed to the one calibration point within the field of view;

directing each photoacoustic calibration signal to the at least one transducer device via the ergodic relay, wherein each photoacoustic calibration signal is detected at the at least one transducer device after one of a plurality of corresponding delays after producing one of the plurality of focused light pulses, each delay corresponding to one of the plurality of calibration points at which one of the plurality of photoacoustic calibration signals is produced;

forming a calibration data set comprising the plurality of positions of each calibration point within the field of view and the plurality of corresponding delays, each corresponding delay corresponding to the position of one of the plurality of calibration points.

18. The method of claim 17, further comprising moving the ergodic relay in a scanning pattern to position each of the plurality of focused light pulses at each position of each calibration point.

19. The method of claim 14, further comprising estimating changes in blood oxygenation based on changes in a magnitude of the plurality of photoacoustic signals between two or more photoacoustic images obtained using the photoacoustic imaging system.

20. The method of claim 14, further comprising identifying a vascularization pattern of an individual subject using the photoacoustic imaging system.

21. The method of claim 14, further comprising identifying a hemodynamic response within a subject by comparing multiple images obtained using the photoacoustic imaging system.

* * * * *